US011173197B2

(12) United States Patent
Ciotti

(10) Patent No.: US 11,173,197 B2
(45) Date of Patent: Nov. 16, 2021

(54) METHODS AND COMPOSITIONS FOR NANOEMULSION VACCINE FORMULATIONS

(71) Applicant: BlueWillow Biologics, Inc., Ann Arbor, MI (US)

(72) Inventor: Susan Ciotti, Ann Arbor, MI (US)

(73) Assignee: BlueWillow Biologics, Inc., Ann Arbor, MI (US)

(*) Notice: Subject to any disclaimer, the term of this patent is extended or adjusted under 35 U.S.C. 154(b) by 0 days.

(21) Appl. No.: 15/203,358

(22) Filed: Jul. 6, 2016

(65) Prior Publication Data

US 2017/0007689 A1 Jan. 12, 2017

Related U.S. Application Data

(60) Provisional application No. 62/189,595, filed on Jul. 7, 2015, provisional application No. 62/218,395, filed on Sep. 14, 2015.

(51) Int. Cl.
| | | |
|---|---|---|
| *A61K 39/07* | (2006.01) | |
| *A61K 9/107* | (2006.01) | |
| *A61K 9/00* | (2006.01) | |
| *A61K 39/00* | (2006.01) | |

(52) U.S. Cl.
CPC ............ *A61K 39/07* (2013.01); *A61K 9/0043* (2013.01); *A61K 9/1075* (2013.01); *A61K 2039/543* (2013.01); *A61K 2039/55566* (2013.01)

(58) Field of Classification Search
CPC . A61K 9/14; A61K 9/00; A61K 9/107; A61K 39/00; A61K 39/39; A61K 9/19; A01N 25/04; A61P 37/00
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 4,895,452 | A | 1/1990 | Yiournas et al. |
| 5,103,497 | A | 4/1992 | Hicks |
| 5,656,730 | A | 8/1997 | Lee |
| 6,015,832 | A | 1/2000 | Baker, Jr. et al. |
| 6,133,229 | A | 10/2000 | Gibson et al. |
| 6,506,803 | B1 | 1/2003 | Baker, Jr. et al. |
| 6,559,189 | B2 | 5/2003 | Baker, Jr. et al. |

(Continued)

FOREIGN PATENT DOCUMENTS

| | | |
|---|---|---|
| WO | WO 00/48635 A1 | 8/2000 |
| WO | WO 2004/007520 A2 | 1/2004 |
| WO | WO 2007/003936 A1 | 1/2007 |

OTHER PUBLICATIONS

International Search Report and Written Opinion issued in related International Patent Application No. PCT/US2016/041166, dated Nov. 18, 2016.

(Continued)

*Primary Examiner* — Jana A Hines
(74) *Attorney, Agent, or Firm* — Foley & Lardner LLP

(57) ABSTRACT

The present disclosure relates to nanoemulsion vaccine compositions and methods of making and using the same. The disclosed compositions and methods provide a means of treating, preventing, or protecting an individual from anthrax exposure or poisoning.

27 Claims, 51 Drawing Sheets

(56) References Cited

U.S. PATENT DOCUMENTS

| | | | | |
|---|---|---|---|---|
| 6,579,688 | B2 | 6/2003 | Steaffens et al. | |
| 6,635,676 | B2 | 10/2003 | Baker, Jr. et al. | |
| 6,875,432 | B2 * | 4/2005 | Liu | A61K 9/0019 424/130.1 |
| 7,314,624 | B2 | 1/2008 | Baker et al. | |
| 7,655,252 | B2 | 2/2010 | Baker, Jr. et al. | |
| 7,767,216 | B2 | 8/2010 | Baker, Jr. et al. | |
| 8,226,965 | B2 | 7/2012 | Baker, Jr. et al. | |
| 8,232,320 | B2 | 7/2012 | Baker, Jr. et al. | |
| 8,236,335 | B2 | 8/2012 | Baker, Jr. et al. | |
| 8,668,911 | B2 | 3/2014 | Baker, Jr. et al. | |
| 8,703,164 | B2 | 4/2014 | Annis et al. | |
| 8,747,872 | B2 | 6/2014 | Baker et al. | |
| 8,771,731 | B2 | 7/2014 | Baker, Jr. et al. | |
| 8,877,208 | B2 | 11/2014 | Baker, Jr. et al. | |
| 8,962,026 | B2 | 2/2015 | Baker, Jr. et al. | |
| 9,131,680 | B2 | 9/2015 | Annis et al. | |
| 2004/0043041 | A1 | 3/2004 | Baker, Jr. et al. | |
| 2005/0272657 | A1 | 12/2005 | O'Connor et al. | |
| 2006/0257426 | A1 | 11/2006 | Baker et al. | |
| 2008/0181949 | A1 * | 7/2008 | Baker | A01N 25/04 424/484 |
| 2009/0291095 | A1 | 11/2009 | Baker, Jr. et al. | |
| 2009/0304799 | A1 | 12/2009 | Baker et al. | |
| 2010/0183675 | A1 * | 7/2010 | Watkinson | A61K 39/07 424/246.1 |
| 2011/0280911 | A1 * | 11/2011 | Myc | A61K 9/0043 424/277.1 |
| 2013/0183350 | A1 | 7/2013 | Harper et al. | |
| 2013/0309273 | A1 * | 11/2013 | Hassett | A61K 9/19 424/400 |
| 2015/0023998 | A1 | 1/2015 | Kaisheva | |
| 2015/0335752 | A1 | 11/2015 | Look | |

OTHER PUBLICATIONS

Bielinska et al., "Mucosal immunization with a novel nanoemulsion based recombinant anthrax protective antigen vaccine protects against Bacillus anthracis spore challenge," Infection and Immunity, vol. 75, No. 8, pp. 4020-4029 (2007).

Kamerzell, et al., "Protein-excipient interactions: mechanisms and biophysical characterization applied to protein formulation development," *Adv. Drug. Delivery Rev.*, vol. 63, pp. 1118-1159 (2011)[Abstract].

Ohtake et al., "Interactions of formulation excipients with proteins in solution and in the dried State," *Adv Drug Delivery Rev.*, vol. 63, No. 13, pp. 1053-1073 (2011) [Abstract].

Wang, et al., "Decellularized liver scaffolds effectively support the proliferation and differentiation of mouse fetal hepatic progenitors," *J. Biomed. Material Res. A.*, 102(4), pp. 1017-1025 (2014).

Jiang et al., "Anthrax Vaccine Powder Formulations for Nasal Mucosal Delivery," *Journal of Pharmaceutical Sciences*, 95: 80-96 (2006).

Richter et al., "Transgenic Plants as Edible Vaccines," *Curr. Top. Microbiology Immunology*, vol. 240, pp. 159-176 (1999).

Mor et al., "Perspective: edible vaccines—a concept coming of age," *Trends Microbiology*, vol. 6, pp. 449-453 (1998).

Ruedi et al., "Features of Oral Immunization," *Int. Arch. Immunol.*, vol. 108, pp. 334-339 (1995).

Leibly, et al., "Stabilizing Additives Added during Cell Lysis Aid in the Solubilization of Recombinant Proteins," PLOS One, vol. 7, No. 12, e52482 (13 pages).

Kaushik, et al., "Why is trehalose an exceptional protein stabilizer? An Analysis of the Thermal Stability of Proteins in the Presence of the Compatible Osmolyte Trehalose," The Journal of Biological Chemistry, vol. 278, No. 29, pp. 26458-26465 (2003).

International Search Report and Written Opinion issued in related International Patent Application No. PCT/US2016/041170, dated Oct. 14, 2016.

Supplemental Search Report issued in co-pending European Patent Application No. 16821925.1, dated Mar. 8, 2019.

Parkins, et al., "The Formulation of Biopharmaceutical Products," *PSTT*, vol. 3, No. 4, pp. 129-137 (Apr. 2000).

Final Office Action issued in co-pending U.S. Appl. No. 15/260,145, dated Jan. 31, 2019.

Wang, et al., "Instability, stabilization, and formulation of liquid protein pharmaceuticals," International *Journal of Pharmaceutics*, vol. 185, pp. 129-188 (1999).

Wang, et al., "Protein Aggregation-Pathways and Influencing Factors," *International Journal of Pharmaceutics*, vol. 390, pp. 89-99 (2010).

Final Office Action issued in co-pending U.S. Appl. No. 15/203,387, dated Jan. 18, 2019.

Office Action issued in co-pending U.S. Appl. No. 15/203,387, dated Aug. 19, 2019.

Office Action issued in co-pending U.S. Appl. No. 15/260,145, dated Sep. 23, 2019.

Office Action issued in co-pending U.S. Appl. No. 15/203,387, dated Mar. 3, 2020.

Office Action issued in co-pending United Kingdom Application No. 1801566.9, dated Feb. 26, 2020.

Office Action issued in co-pending U.S. Appl. No. 15/260,145, dated Apr. 7, 2020.

Foreign Examination Report on GB Appl. Ser. No. 1801566.9 dated, Jul. 10, 2020 (4 pages).

Advisory Action issued in co-pending U.S. Appl. No. 15/203,387, dated Jul. 21, 2020.

Advisory Action issued in co-pending U.S. Appl. No. 15/260,145, dated Jul. 21, 2020.

Office Action issued in co-pending U.S. Appl. No. 15/203,387, dated Oct. 5, 2020.

Office Action issued in co-pending U.S. Appl. No. 15/203,387, dated Feb. 10, 2021.

International Preliminary Report on Patentability issued in related International Patent Application No. PCT/US2016/041166, dated Jan. 18, 2018.

International Preliminary Report on Patentability issued in related International Patent Application No. PCT/US2016/041170, dated Jan. 18, 2018.

Non-Final Office Action issued in co-pending U.S. Appl. No. 15/203,387, dated Jul. 5, 2018.

Non-Final Office Action issued in co-pending U.S. Appl. No. 15/260,145, dated Jul. 11, 2018.

* cited by examiner

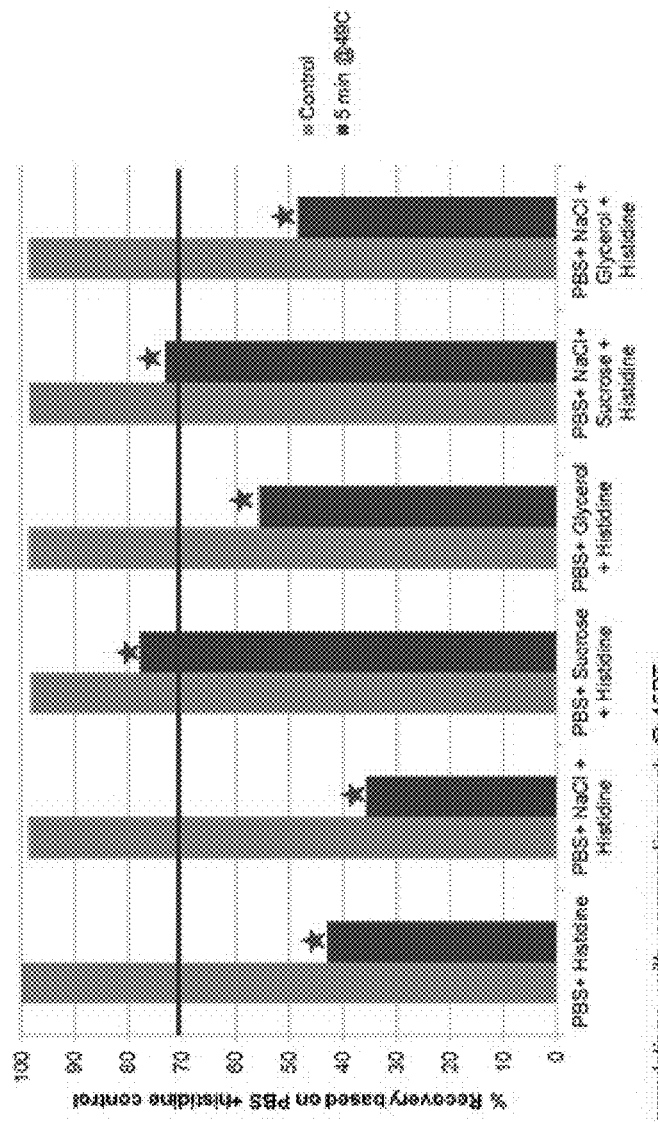
Figure 12 Con't

Figure 21
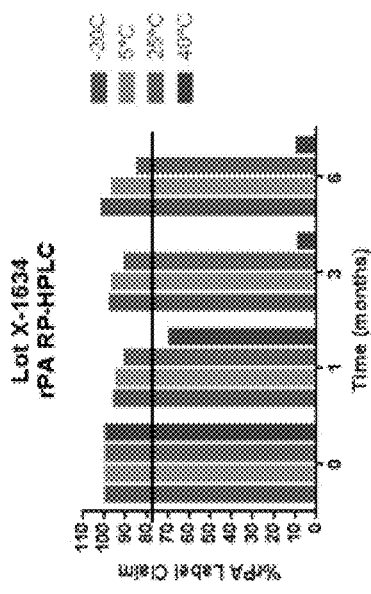
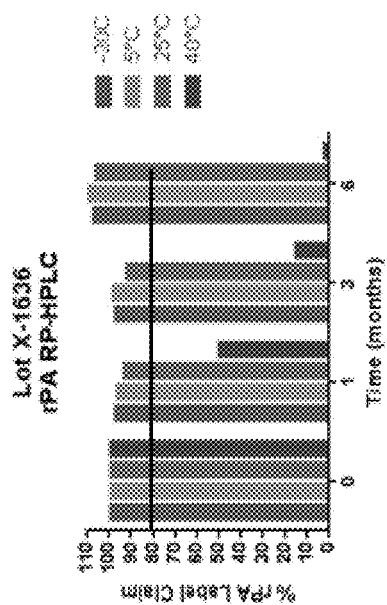

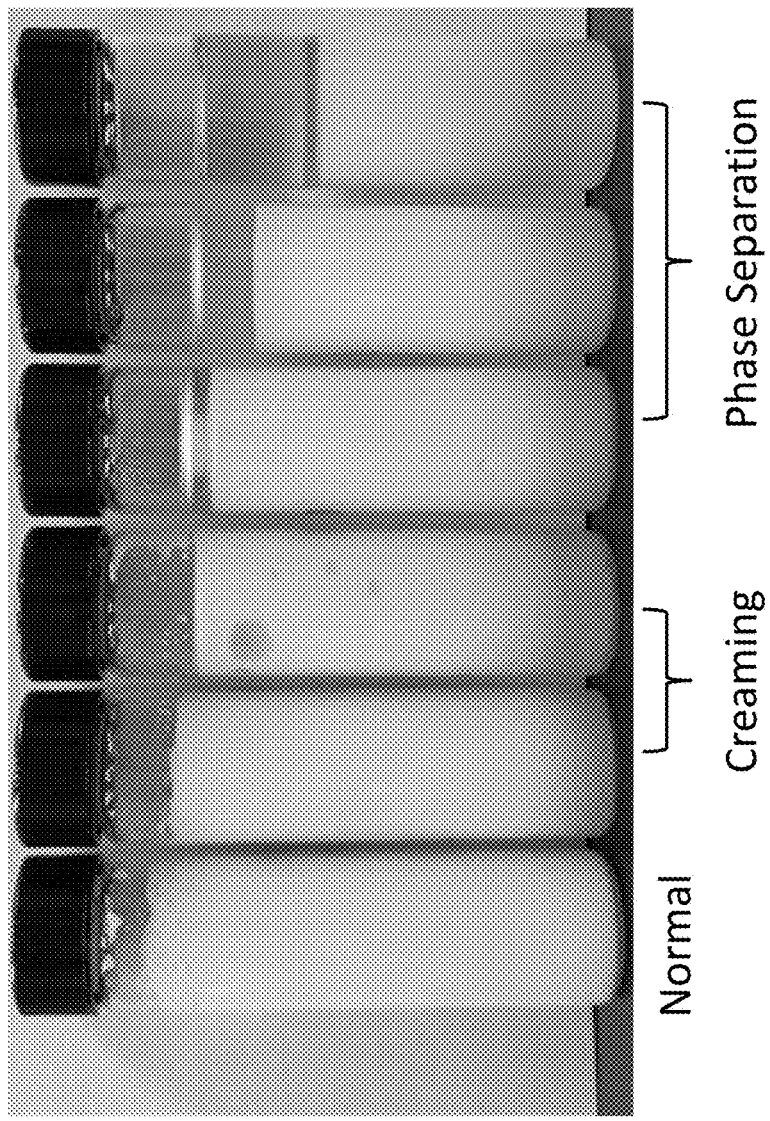
Figure 27 Con't

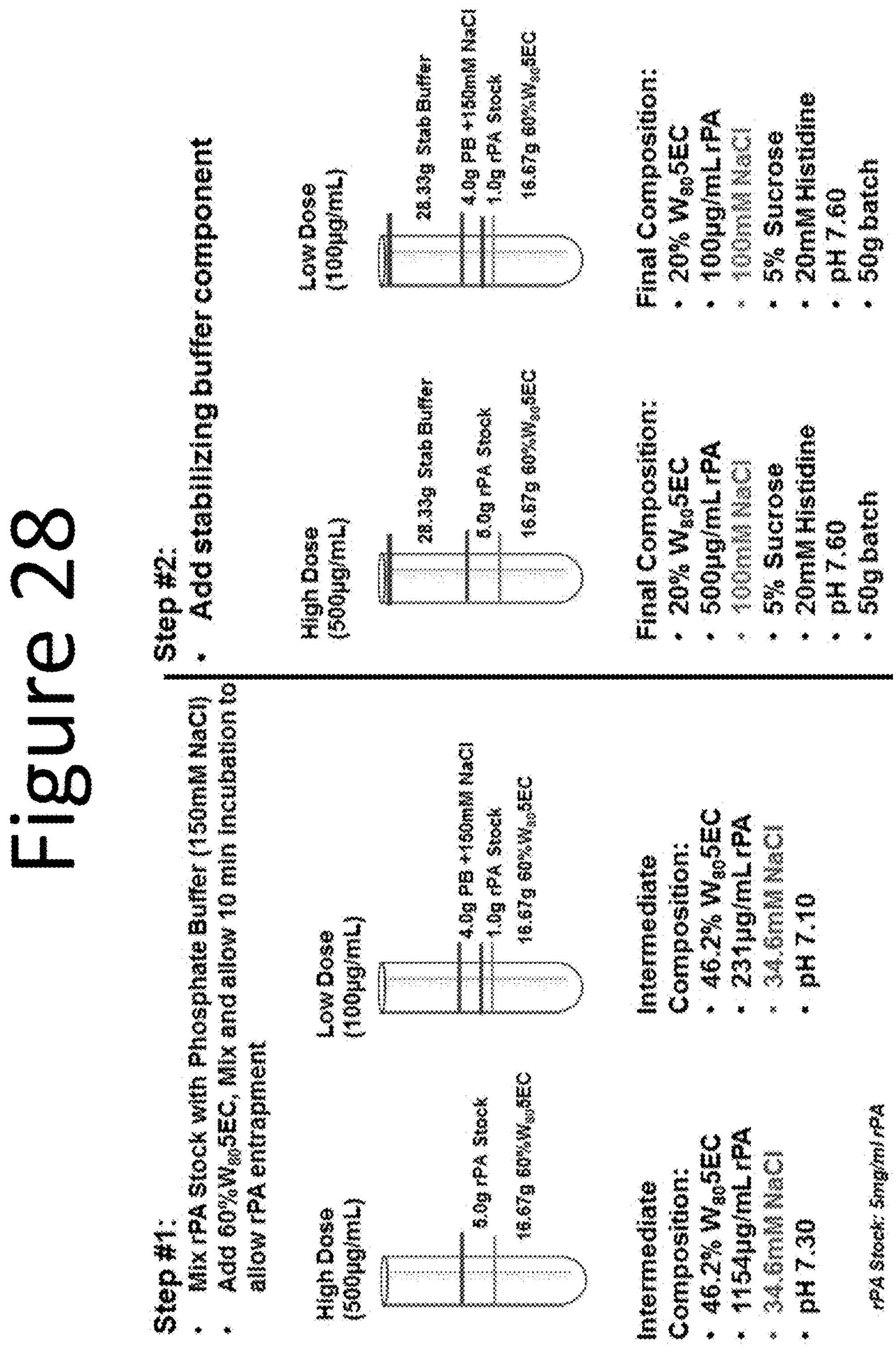

Figure 28

Step #1:
• Mix rPA Stock with Phosphate Buffer (150mM NaCl)
• Add 60% $W_{80}$5EC, Mix and allow 10 min incubation to allow rPA entrapment
High Dose (500µg/mL)
5.0g rPA Stock
16.67g 60% $W_{80}$5EC
Low Dose (100µg/mL)
4.0g PB +150mM NaCl
1.0g rPA Stock
16.67g 60% $W_{80}$5EC
Intermediate Composition:
• 46.2% $W_{80}$5EC
• 1154µg/mL rPA
• 34.6mM NaCl
• pH 7.30
Intermediate Composition:
• 46.2% $W_{80}$5EC
• 231µg/mL rPA
• 34.6mM NaCl
• pH 7.10
rPA Stock: 5mg/ml rPA
Step #2:
• Add stabilizing buffer component
High Dose (500µg/mL)
28.33g Stab Buffer
5.0g rPA Stock
16.67g 60% $W_{80}$5EC
Low Dose (100µg/mL)
28.33g Stab Buffer
4.0g PB +150mM NaCl
1.0g rPA Stock
16.67g 60% $W_{80}$5EC
Final Composition:
• 20% $W_{80}$5EC
• 500µg/mL rPA
• 100mM NaCl
• 5% Sucrose
• 20mM Histidine
• pH 7.60
• 50g batch
Final Composition:
• 20% $W_{80}$5EC
• 100µg/mL rPA
• 100mM NaCl
• 5% Sucrose
• 20mM Histidine
• pH 7.60
• 50g batch

METHODS AND COMPOSITIONS FOR NANOEMULSION VACCINE FORMULATIONS

CROSS-REFERENCE TO RELATED APPLICATIONS

This application claims priority to U.S. Provisional Patent Application No. 62/189,595 filed on Jul. 7, 2015, and U.S. Provisional Patent Application No. 62/218,395 filed on Sep. 14, 2015, the disclosures of which are specifically incorporated by reference in their entirety.

FIELD OF THE APPLICATION

The present application is directed to vaccine formulations comprising a stabilized recombinant protective antigen (rPA) of anthrax and/or carrier proteins and methods of using the same. The disclosed rPA vaccines and methods of using the same may be useful in the treatment and/or prevention of anthrax infection or poisoning in subjects in need thereof.

BACKGROUND OF THE INVENTION

A. Protein Stabilization

To stabilize labile products, some try to immobilize or reduce the water content of stored samples. For example, some biological materials can be stabilized by chilling or freezing. However, maintaining and transporting frozen samples is costly, and freezer breakdown may result in the complete loss of valuable product. Alternatively, bio-products can be freeze-dried to provide a dry, active, shelf-stable, and readily soluble product. However, a protein or biologic drug product can be damaged during the freeze-drying process in numerous ways. Often regarded as a gentle method, freeze drying is in reality a potentially damaging process where the individual process stages should be regarded as a series of interrelated stresses, each of which can damage sensitive bio-products. Damage sustained during one step in the process may be exacerbated at succeeding stages in the process chain, and even apparently trivial changes in the process, such as a change in container, may be sufficient to transform a successful process to one which is unacceptable. Reducing temperature in the presence of ice formation is the first major stress imposed on a biomolecule. Biomolecules in vaccine products are more likely to be damaged by an increase in solute concentration as ice forms. Further, freeze-drying is less appropriate for oily or non-aqueous solutions where the material has a low melting temperature.

B. Proteins in Vaccines

Immunization is a principal feature for improving the health of people. Despite the availability of a variety of successful vaccines against many common illnesses, infectious diseases remain a leading cause of health problems and death. Significant problems inherent in existing vaccines include the need for repeated immunizations, and the ineffectiveness of the current vaccine delivery systems for a broad spectrum of diseases.

One problem present in the art is the frequent denaturation of protein antigens present in vaccine formulations. Many vaccines contain protein antigens to confer protective immunity. This is because antibodies are most likely to be protective if they bind to the surface of the invading pathogen triggering its destruction. Several vaccines employ purified surface molecules. For example, influenza vaccine contains purified hemagglutinins from the viruses currently in circulation around the world. In addition, the gene encoding a protein expressed on the surface of the hepatitis B virus, called hepatitis B surface antigen or HBsAg, can now be expressed in *E. coli* cells and provides the material for an effective vaccine. The genes encoding the capsid proteins of 4 strains of human papilloma virus (HPV) can be expressed in yeast and the resulting recombinant proteins are incorporated in a vaccine (Gardasil®). Because infection with some of these strains of HPV can lead to cervical cancer, the HPV vaccine is useful to prevent certain types of cancer.

Other types of vaccines can utilize a poor (polysaccharide organism) antigen coupled to a carrier protein (preferably from the same microorganism), thereby conferring the immunological attributes of the carrier on the attached antigen. This technique for the creation of an effective immunogen is most often applied to bacterial polysaccharides for the prevention of invasive bacterial disease.

One disadvantage of vaccines comprising protein antigens, or a carrier protein, is that if the protein present in the vaccine formulation can become unstable, resulting in denaturation. Denaturation of a protein antigen can produce loss in effective binding, and thereby a decrease in production of protective antibodies. Similarly, denaturation of a carrier protein present in a conjugate vaccine can also result in loss in effective binding, and thereby a decrease in production of protective antibodies.

Thus, it would be a great advance in the field if vaccine products could be stabilized without the need for freeze-drying or storage conditions at below sub-zero temperatures (−20 to −80° C.). Developing a stabile liquid-based solution that extends the shelf-life of the antigen at simple refrigerated temperatures (2 to 8° C.) or, more importantly, room temperature (25° C.) would greatly reduce the manufacturing costs (e.g. freeze-drying cost prohibitive) and supply chain needs for products that need storage at −20° C. to −80° C.

C. Anthrax Infection

Anthrax is an infectious disease caused by the bacterium *Bacillus anthracis*, and in humans, the infection most often involves the skin, gastrointestinal tract, or the lungs. Aside from human, anthrax also commonly affected animals such as sheep, cattle, and goats.

Cutaneous anthrax occurs when anthrax spores come into contact with a cut or scrape on a subject's skin. Gastrointestinal may occur from someone ingesting tainted meat. Inhalation anthrax develops when anthrax spores enter the lungs through the respiratory tract, and can occur when workers breathe in airborne spores during the processing of animal hides or wool, as well as from weaponized formulations of the spores.

Breathing in anthrax spores exposes an individual to anthrax, but the individual may or may not immediately develop symptoms. The anthrax spores must germinate before the actual disease occurs, which can take anywhere from roughly 1 to 6 days. When the spores germinate, several toxins are released, which can cause bleeding, swelling, necrosis, and, potentially, death.

Given the potential use of anthrax as a biological weapon or for uses in bioterrorism, a vaccine against anthrax would be clearly beneficial.

Thus, there remains a need in the art for effective vaccines against pathogens, such as anthrax, that have been recalcitrant to vaccine development and methods of making and using the same. There is also a need to overcome the failings of commercially available vaccines due to expense, complexity, and underutilization. To accomplish these goals, new methods of antigen presentation must be developed which will allow for fewer immunizations, more efficient usage, and/or fewer side effects to the vaccine. The present invention satisfies these needs.

SUMMARY OF INVENTION

The present disclosure relates primarily to methods and compositions of vaccine formulations comprising stabilized recombinant protective antigen (rPA).

A composition, comprising a recombinant protective antigen (rPA) of anthrax, a nanoemulsion, and a stabilizing system, wherein the stabilizing system comprises a TRIS buffer, a salt, a sugar, and an amino acid.

In some embodiments, the composition can comprise, or alternatively consist essentially of, or yet further consist of, rPA, a nanoemulsion, and a stabilizing system, as disclosed herein.

In some embodiments, the concentration of rPA is 100 µg/ml, while in other embodiments, the concentration is 500 µg/ml.

In some embodiments, the nanoemulsion is $W_{80}5EC$ nanoemulsion adjuvant, and in some embodiments, the $W_{80}5EC$ nanoemulsion adjuvant is present in a concentration of about 20%.

In some embodiments, the TRIS buffer is in a concentration of about 5-about 100 mM. In some embodiments, the TRIS buffer is in a concentration of about 10 mM or about 80 mM.

In some embodiments, the salt is sodium chloride, while in other embodiments, the salt is calcium chloride. In some embodiments, the concentration of the salt is about 50-about 150 mM.

In some embodiments, the sugar is trehalose, and in some embodiments, the concentration of trehalose is about 5-about 15%. In some embodiments, the amino acid is histidine. In some embodiments, the histidine is in a concentration of about 20-about 70 mM, or, more specifically, about 60 mM.

In some embodiments, the invention encompasses a stabilized composition, comprising anthrax recombinant protective antigen (rPA) in a stabilizing system, wherein the stabilizing system comprises TRIS buffer; a salt; a sugar; and an amino acid. In some embodiments, the TRIS buffer is in a concentration of about 5-about 100 mM. In some embodiments, the TRIS buffer is in a concentration of about 10 mM or about 80 mM.

In some embodiments, the salt is sodium chloride, while in other embodiments, the salt is calcium chloride. In some embodiments, the concentration of the salt is about 50-about 150 mM.

In some embodiments, the sugar is trehalose, and in some embodiments, the concentration of trehalose is about 5-about 15%. In some embodiments, the amino acid is histidine. In some embodiments, the histidine is in a concentration of about 20-about 70 mM, or, more specifically, about 60 mM.

In some embodiments, the composition can be formulated into a pharmaceutical composition, for instance, a vaccine.

In another aspect, the disclosure provides methods of treating or preventing anthrax infection, exposure, or poisoning in a subject, comprising administering to an individual in need thereof a composition, comprising a recombinant protective antigen (rPA) of anthrax, a nanoemulsion, and a stabilizing system, wherein the stabilizing system comprises: a TRIS buffer, a salt, a sugar, and an amino acid.

In some embodiments, the individual is at risk of being exposed to anthrax, and in some embodiments, the composition is administered intranasally.

The foregoing general description and following brief description of the drawings and the detailed description are exemplary and explanatory and are intended to provide further explanation of the disclosed as claimed. Other objects, advantages, and novel features will be readily apparent to those skilled in the art from the following detailed description of the disclosed.

BRIEF DESCRIPTION OF DRAWINGS

FIG. 21 shows rPA aqueous (AQ) (P3−GT) formulations by temperature and month.

FIG. 28 shows an optimized mixing procedure for the rPA+Nanoemulsion with stabilizing buffer.

DETAILED DESCRIPTION

I. Overview

Figure 1:
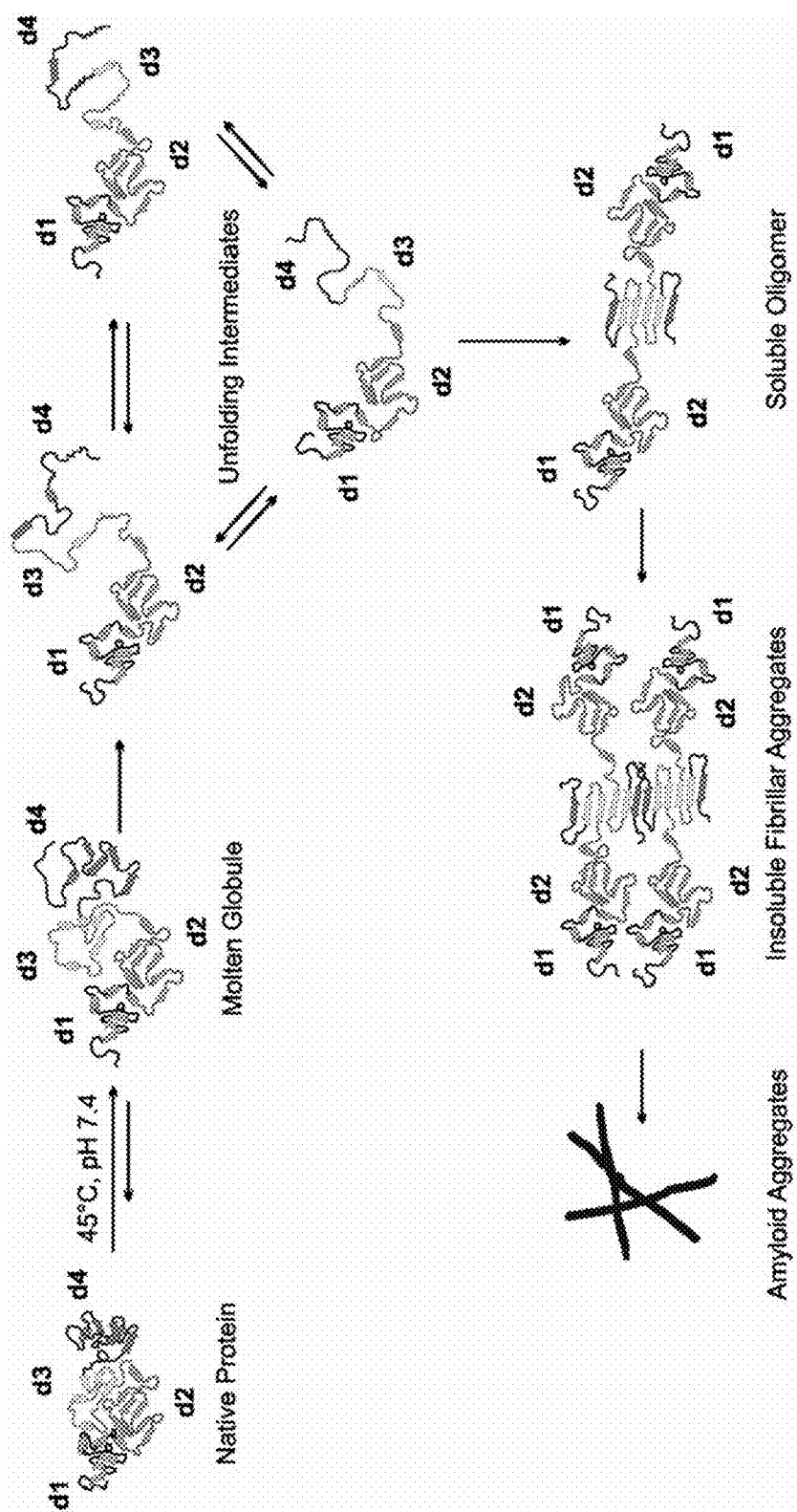
FIG. 1 shows an example of protein denaturation.

The present invention is directed to compositions and methods of stabilizing anthrax recombinant protective antigen (rPA) for use in vaccine formulations. The invention also encompasses vaccine compositions comprising such stabilized protein antigens or carrier proteins, and methods of using such vaccine compositions.

Protein instability, as evidenced by protein aggregation and/or protein denaturation, in a vaccine formulation is highly undesirable as it can significantly affect the therapeutic effectiveness of a vaccine, including failure to produce a therapeutic level of neutralizing antibodies.

Protein aggregation can occur at all steps in the manufacturing process (cell culture, purification, and formulation), storage, distribution and handling of products. It results from various kinds of stress such as agitation and exposure to extremes of pH, temperature, ionic strength, or various interfaces (e.g. air-liquid interface, liquid-container interface, etc).

Understanding protein aggregation and stability is critical for rational protein design and especially relevant to protein therapeutics. The present invention is directed to methods and compositions utilizing the best excipients to stabilize and reduce aggregation of proteins for use in vaccines, such as rPA. To identify a preferred methodology, pre-formulation experiments were conducted to evaluate the physicochemical properties of a vaccine, such as pH, buffer ingredients, thermostabilizers, and antioxidants. The studies used a stability-indicating method to discover novel stabilizing excipient combinations. See e.g., Examples 1-5 below.

It can be difficult to achieve long-term stability of a vaccine product comprising a protein antigen or a protein carrier. It is known that stabilizing agents/excipients can be added to a formulation to increase the shelf-life of a product to a limited extent. See Kamerzell et al., "Protein-excipient interactions; mechanisms and biophysical characterization applied to protein formulation development," Adv. Drug Deliv. Rev., 63: 1118-1159 (2011); and Ohtake et al., "Interactions of formulation excipients with proteins in solution and in the dried state," Adv. Drug Deliv. Rev., 63(13):1053-73 (October, 2011). The present invention is directed to the discovery that combinations of various excipients may be a means to provide additional thermo-stability protection of protein antigens and carrier proteins for use in vaccines.

In the studies described herein, a model protein was used to determine a preferred methodology for identifying optimal stability conditions. The model protein used herein was recombinant anthrax protective antigen (rPA).

The present invention provides vaccine compositions made according to the methods of the invention, and methods of using the same. The vaccine compositions are useful for the stimulation of immune responses in humans or animals. In one embodiment of the invention, the stabilized protein antigen, or protein carrier, can be combined with a nanoemulsion to form a nanoemulsion vaccine, although the invention is not limited to nanoemulsion vaccines. Nanoemulsion vaccines comprise a stabilized protein antigen, or a stabilized carrier protein coupled to an antigen, and a nanoemulsion, which comprises an aqueous phase, at least one oil, at least one surfactant, and at least one solvent. The nanoemulsion vaccine composition can comprise one or more stabilized protein antigens, or stabilized carrier proteins, within an oil phase of the nanoemulsion.

Methods of using non-nanoemulsion vaccines and nanoemulsion vaccines according to the invention for the induction of immune responses, e.g., innate and/or adaptive immune responses (e.g., for generation of host immunity against an environmental pathogen such as anthrax), are also encompassed by the invention. Vaccine compositions and methods of the present invention find use in, among other things, clinical, e.g. therapeutic and preventative medicine, e.g., vaccination, and research applications.

The present invention is not limited to any mechanism of action. Indeed, an understanding of the mechanism is not necessary to practice the present invention. It is contemplated that the vaccine compositions of the invention, comprising a stabilized protein antigen or stabilized carrier protein, elicits a robust immune response against the stabilized protein antigen/stabilized carrier protein+antigen, (ii) stability of the stabilized protein antigen/stabilized carrier protein, and/or (iii) enhanced uptake and delivery of the stabilized protein antigen/stabilized carrier protein to antigen presenting cells (e.g., dendritic cells) facilitated by stabilized protein antigen/stabilized carrier protein.

For the purposes of this disclosure, where rPA is present in a nanoemulsion vaccine, it is contemplated that rPA resides within the internal oil phase of the nanoemulsion, elicits a robust immune response against the rPA due to, among other things, (i) solvation of the oil phase by the organic solvent of the nanoemulsion (e.g., that facilitates location of the stabilized protein antigen/stabilized carrier protein to within the oil phase of the nanoemulsion), (ii) stability of the stabilized protein antigen within the oil phase of the nanoemulsion, and/or (iii) enhanced uptake and delivery of the stabilized protein antigen to antigen presenting cells (e.g., dendritic cells) facilitated by stabilized protein antigen residing within the oil phase of the nanoemulsion.

In particular, nanoemulsion/stabilized protein antigen compositions of the disclosure elicit robust mucosal immune responses. See e.g., Richter and Kipp, Curr. Top. Microbiol. Immunol., 240: 159-76 (1999); Ruedl and Wolf, Int. Arch. Immunol., 108:334 (1995); and Mor et al., Trends Micrbiol., 6:449-53 (1998) for reviews of the mucosal immune system. Mucosal antigens stimulate the Peyer's Patches (PP) of the gastrointestinal tract. The M cells of the PP then transport antigens to the underlying lymph tissue where they encounter B cells and initiate B cell development. IgA is secreted by primed B cells that have been induced to produce IgA by Th2 helper T cells. Primed B cells are transported throughout the lymph system where they populate all secretory tissues. IgAs are then secreted in mucosal tissues where they serve as a first-line defense against many viral and bacterial pathogens.

A. Proteins for the Disclosed Methods and Compositions

Anthrax protective antigen, to which the present disclosure applies, may be generated by biosynthesis using recombinant DNA technology and are referred to herein as "recombinant proteins" or "recombinantly produced proteins." The skilled reader will know how to use recombinant technology to biosynthesize the proteins and precursor proteins of the present disclosure.

Preferred proteins of this disclosure include proteins that are folded globular proteins, although the disclosure is not limited to globular proteins, such as rPA. The novel formulations of the present disclosure retain the physical, chemical, and biological stability of the protein or proteins incorporated therein, and prevent the proteins, which may be intended for administration into a subject, from forming aggregates and/or particulates. The disclosed compositions and methods further prevent protein denaturation and preserve the stabilized protein or proteins in solution for an extended period of time.

There are two general categories of proteins that are commonly recognized: fibrous proteins and globular proteins. Fibrous proteins do not easily denature, such as keratins, collagens and elastins. They are robust, relatively insoluble, quaternary structured proteins that play important roles in the physical structure of organisms. Corresponding to this structural function, they are relatively insoluble in water and unaffected by moderate changes in temperature and pH. The more flexible and elastic keratins of hair have fewer interchain disulfide bridges than the keratins in mammalian fingernails, hooves and claws.

Figure 8:
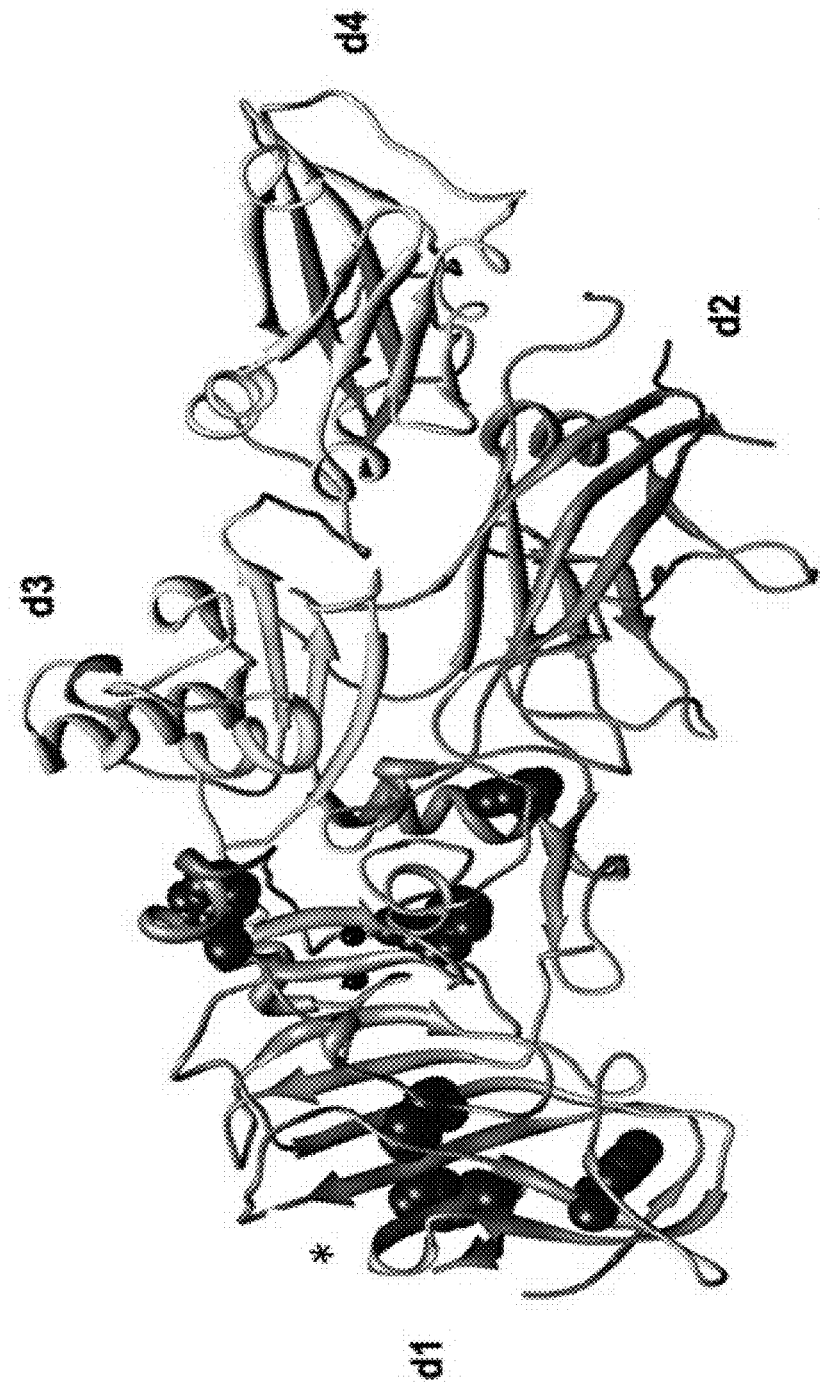
FIG. 8 shows a ribbon diagram of the tertiary structure of rPA showing the domains: d1, d2, d3, and d4, and where * indicates calcium atoms are binding.
Figure 25:
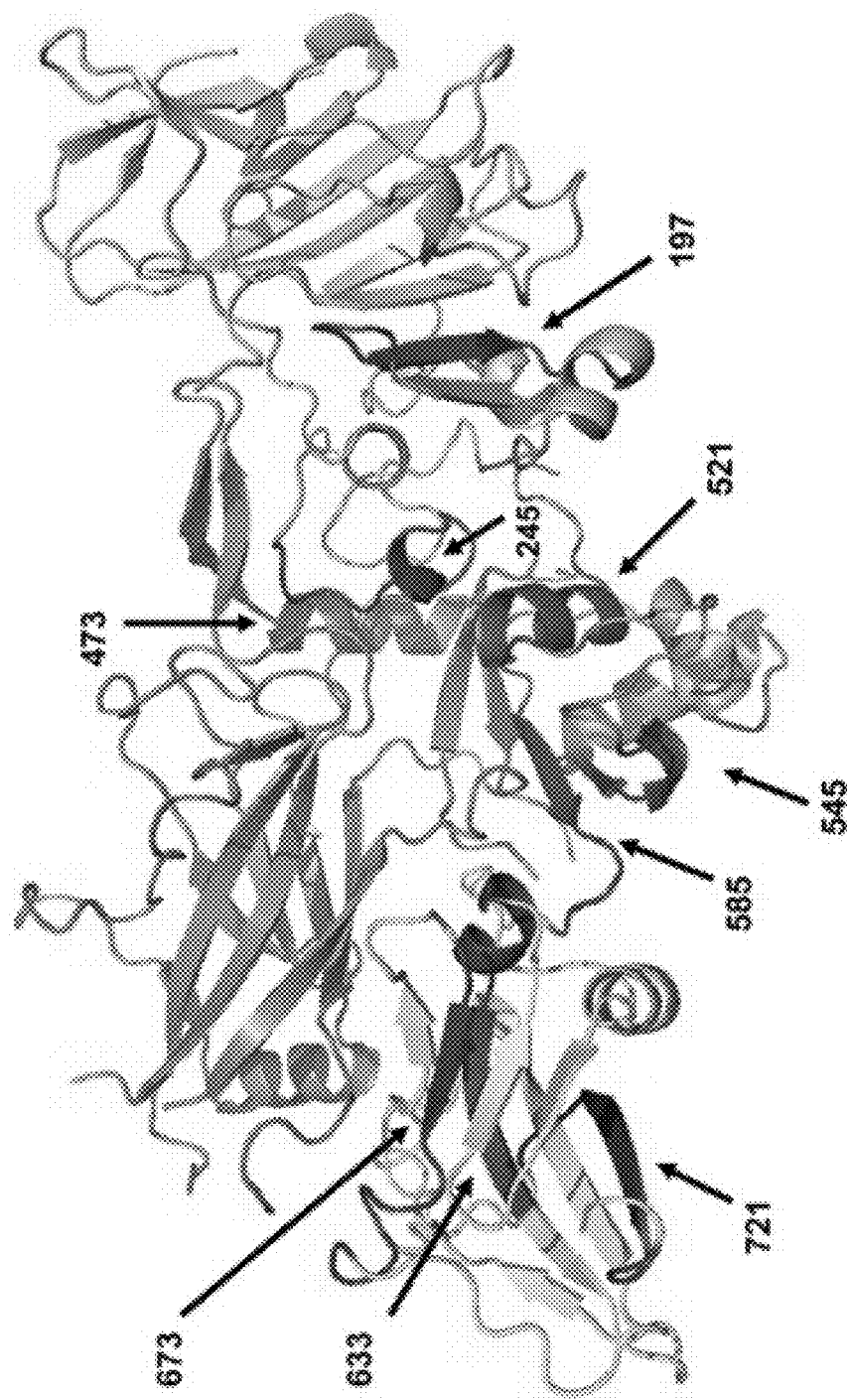
FIG. 25 shows a ribbon diagram of the tertiary structure of rPA showing the nine peptide epitopes that exhibited significantly and reproducibly stronger reactivity to sera from mice immunized with rPA-Alhydrogel formulations stored for 3 weeks at either room temperature (RT) or 37° C. than to sera from mice immunized with freshly prepared formulations. Peptides are numbered with the residue number of the first amino acid of the 12-mer peptide sequence.
Figure 26:
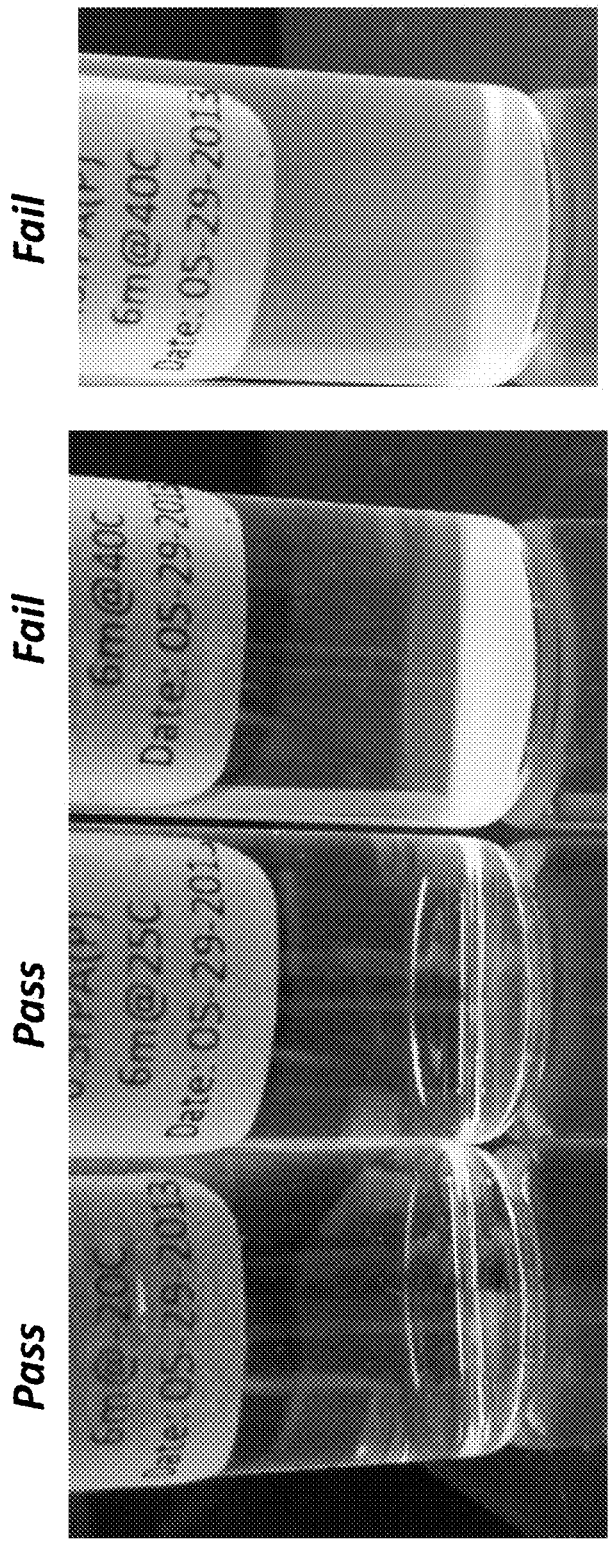
FIG. 26 shows examples of rPA buffered aqueous solutions, with the first two vials being acceptable and the second two failing the stability test.
Figure 27:
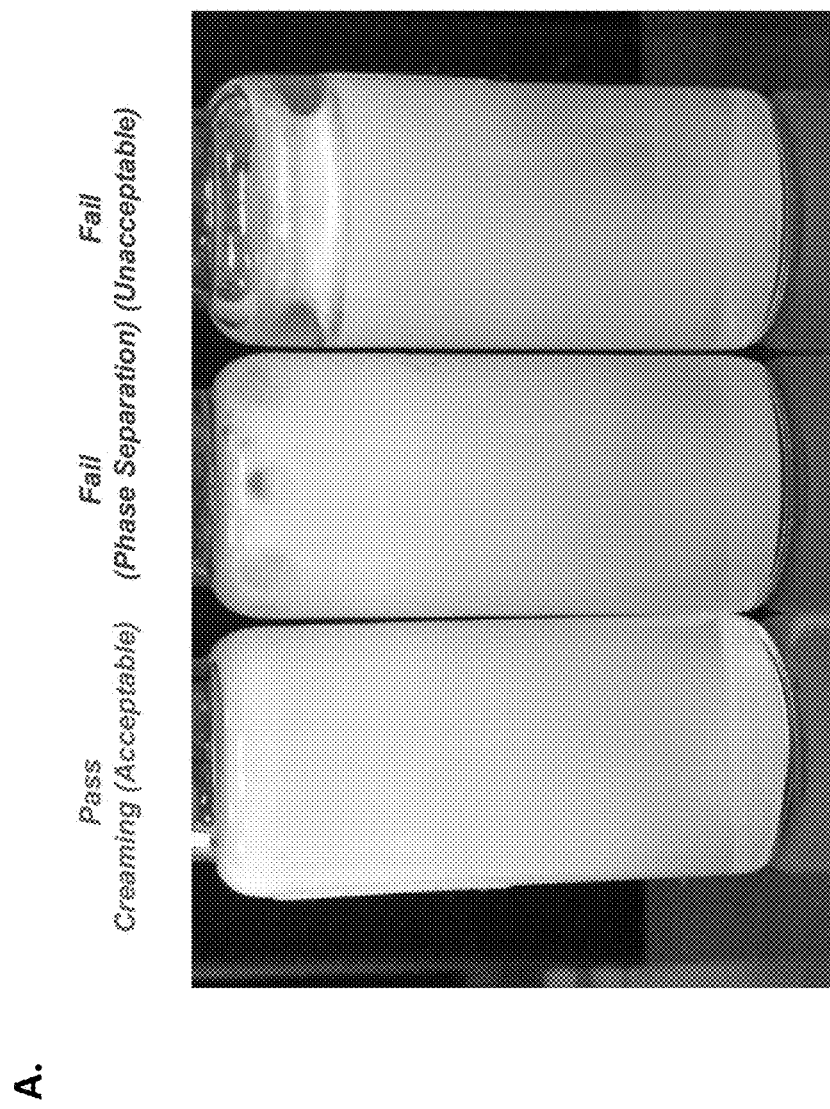
FIG. 27 shows examples of rPA+nanoemulsion buffered aqueous solutions, and what an acceptable (normal) formulation looks like. within Panel (A) the first vial is acceptable and the second two vials fail due to phase separation (demonstrating instability of the formulations). In Panel (B), the first vial is acceptable, while the next two fail due to creaming, and the last three fail due to phase separation.

The term "folded globular protein" refers to a protein in its properly folded, three-dimensional conformation, and includes the designed, desired, or required arrangement of disulfide bonds linking cysteine residues of a protein. Usually, this properly folded disulfide arrangement will be identical to or comparable to that present in its analogous native protein. Preferably, folded proteins stabilized by the process of the present disclosure will have two or more disulfide bonds. rPA is an example of a "folded globular protein," as shown in shown in FIG. 8. Locations of antigenic peptide epitopes within the crystal structure of PA are illustrated. Dark balls are calcium molecules. See also FIG. 25.

Globular proteins are more soluble in aqueous solutions, and are generally more sensitive to temperature and pH change than are their fibrous counterparts; furthermore, they do not have the high glycine content or the repetitious sequences of the fibrous proteins. Globular proteins incorporate a variety of amino acids, many with large side chains and reactive functional groups. The interactions of these substituents, both polar and nonpolar, often cause the protein to fold into spherical conformations which gives this class its name. In contrast to the structural function played by the fibrous proteins, the globular proteins are chemically reactive, serving as enzymes (catalysts), transport agents and regulatory messengers. Such proteins are generally more sensitive to temperature and pH change than their fibrous counterparts.

A 2005 study considered the importance of degree of anthrax antigen (recombinant protective antigen—rPA) adsorption (0, 80% or 100%), adjuvant choice and total antigen content. The vaccines consisted of aluminum hydroxide adjuvant in saline with 100% rPA adsorbed (reminiscent of the only licensed anthrax vaccine approved for use in humans), aluminum phosphate adjuvant in saline with ≥80% rPA adsorbed, and aluminum phosphate adjuvant in sodium phosphate buffer with no rPA adsorbed, only in solution. In the case of this antigen, binding of the protein to adjuvant was not essential for the aluminum-containing adjuvants to boost the anti-rPA response in CDI mice, but instead the mere presence of adjuvant was capable of enhancing anti-PA antibody response, relative to antigen alone in solution. There were differences, however, in the dose-response behavior of the two vaccines containing aluminum phosphate adjuvant.

Specifically, the vaccine with the adsorbed antigen was insensitive to antigen dose, but the vaccine with the soluble antigen yielded a trend of decreasing response with the decreasing antigen concentration. This suggests that at least for rPA, MW ~83 kDa, some degree of adsorption is important in maximizing antibody production when antigen is limited. Interestingly, the only vaccines that elicited neutralizing antibody titers above those elicited by the adjuvant-free rPA solution were those vaccines containing the aluminum phosphate adjuvant, which contained both soluble and adsorbed antigen. The vaccine with 100% of the antigen adsorbed, i.e., that with the aluminum hydroxide adjuvant, did not have a significant effect on the production of neutralizing antibodies. It is suspected that lack of production of neutralizing antibodies is because 100% of the antigen was adsorbed and other factors such as structural changes of the absorbed native protein antigen, particle size, and folding may have played a role.

Heat is one factor that effects protein conformation and structure. The term thermolabile refers to a substance which is subject to destruction/decomposition or change in response to heat. This term is often used to describe biochemical substances, including proteins. A protein or peptide may lose activity due to changes in the three-dimensional structure of the protein during exposure to heat. Many proteins, including the model proteins used in the examples below (i.e. rPA), are thermolabile. Heat denaturation is primarily due to the increased entropic effects of the non-polar residues (that is, the increased entropy gain of the unfolded chain is not much reduced by the small amount of entropy loss caused to the solute).

Proteins that can be stabilized with methods and compositions according of the present disclosure include globular proteins having a tertiary structure. Tertiary structures of globular proteins ("Folded Globular Proteins") involves electrostatic interactions, hydrogen bonding and covalent disulfide bridges. These are areas with barrel shapes known as domains. Each domain is a region within the native tertiary structure that can potentially exist independent of the protein or antigenic peptide epitopes. These include hydrophobic attraction of nonpolar side chains in contact regions of the subunits, electrostatic interactions between ionic groups of opposite charge: hydrogen bonds between polar groups; and disulfide bonds. rPA is an examples of a protein having a tertiary structure.

For the purposed of the disclosed compositions and methods, rPA may be incorporated into vaccine formulations in varying amounts, as necessary for the treatment, prevention, or prophylaxis of anthrax infection or exposure. For instance, a formulation of the disclosed compositions and methods may contain a concentration of rPA in ranges between 1-5000 µg/ml, between 10-1000 µg/ml, between 50-750 µg/ml, or between 100-500 mg/ml. In other words, the concentration of rPA in the disclosed compositions and methods can be about 1, about 2, about 3, about 4, about 5, about 6, about 7, about 8, about 9, about 10, about 20, about 30, about 40, about 50, about 60, about 70, about 80, about 90, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1050, about 1100, about 1150, about 1200, about 1250, about 1300, about 1350, about 1400, about 1450, about 1500, about 1550, about 1600, about 1650, about 1700, about 1750, about 1800, about 1850, about 1900, about 1950, about 2000, about 2050, about 2100, about 2150, about 2200, about 2250, about 2300, about 2350, about 2400, about 2450, about 2500, about 2550, about 2600, about 2650, about 2700, about 2750, about 2800, about 2850, about 2900, about 2950, about 3000, about 3050, about 3100, about 3150, about 3200, about 3250, about 3300, about 3350, about 3400, about 3450, about 3500, about 3550, about 3600, about 3650, about 3700, about 3750, about 3800, about 3850, about 3900, about 3950, about 4000, about 4050, about 4100, about 4150, about 4200, about 4250, about 4300, about 4350, about 4400, about 4450, about 4500, about 4550, about 4600, about 4650, about 4700, about 4750, about 4800, about 4850, about 4900, about 4950, or about 5000 µg/ml.

B. Issues Related to Protein Structure Stabilization

There are four parts to protein stabilization: protein hydration, protein folding, protein crystallization, and protein denaturation.

Protein hydration: When a protein is fully hydrated, the potential energy is reduced and the proteins can attain their minimum-energy conformation. The water molecules can lubricate the movement of the amino acids backbone and the side groups for exchange of hydrogen bonds. Such water promotes both folding rate and stability of the protein.

Protein folding: Protein folding is driven by the aqueous environment, particularly the hydrophobic interactions, due to the unfavorable entropy decrease (mostly translational forming a large surface area of non-polar groups with water). Consider a water molecule next to a surface to which it cannot hydrogen bond. The incompatibility of this surface with the low-density water that forms over such a surface encourages the surface minimization that drives the proteins' tertiary structure formation. Compatible solutes or osmolytes can stabilize the surface low-density water and increase the surface tension, thus to stabilize the protein's structure (Hofmeister effect and the solubility of non-polar gases). Many proteins are glycosylated with increased stability. The role of carbohydrate groups has been debated for many years. It now appears that the increased solubility is mainly as the low intermolecular interaction between surface glycans reduces the tendency for aggregation (and crystallization) rather than the glycan groups increasing interactions with water.

Protein crystallization: Proteins may form crystals when precipitated slowly from an aqueous solution (e.g. of ammonium sulfate). Slow precipitation is required to produce small numbers of larger crystals rather than very large numbers of small crystals. Crystals of un-denatured proteins for structural analysis are best formed with water molecules retained within the crystal lattice. Crystallization of native proteins appears to have a three-step mechanism involving nucleation, in which mesoscopic metastable protein clusters of dense liquid serve as precursors to the ordered crystal nuclei followed by crystal growth. This process seems to involve an aqueous biphasic separation and fits nicely with the two-state structuring in liquid water, where the crystallization takes place within the dense phase.

Protein denaturation: Protein denaturation involves a change in the protein structure (generally an unfolding) with the loss of activity, as shown in FIG. 1. Water is critical, not only for the correct folding of proteins but also for the maintenance of this structure. Heat denaturation and loss of biological activity has been linked to the breakup of the 2-D-spanning water network (see above) around the protein (due to increasing hydrogen bond breakage with temperature), which otherwise acts restrictively on protein vibrational dynamics. The free energy change on folding or unfolding is due to the combined effects of both protein folding/unfolding and hydration changes. These compensate to such a large extent that the free energy of stability of a typical protein is only 40-90 kJ m$^{-1}$ (equivalent to very few hydrogen bonds), whereas the enthalpy change (and temperature times the entropy change) may be greater than ±500 kJ mol$_{-1}$ different. There are both enthalpic and entropic contributions to this free energy that change with temperature and so give rise to heat denaturation and, in some cases, cold denaturation. Protein unfolding at higher temperatures (heat denaturation) is easily understood but the widespread existence of protein unfolding at low temperatures is surprising, particularly as it is unexpectedly accompanied by a decrease in entropy.

The methods and compositions of the present disclosure address the issues of protein stabilization in relation to rPA for use in vaccine formulations by stabilizing the protein in solution such that rPA retains its structure, conformation, and immunological activity. The type of stabilization provided by the disclosure is valuable scientifically, academically, and commercially for the research, development, commercialization, and treatment/administration of rPA-based therapeutics, including vaccines.

II. Novel Methods to Stabilize rPA

The present disclosure is directed to methods of optimizing compositions to stabilize the secondary and tertiary structures of rPA, by proactively screening and addressing all the destabilizing or un-stabilizing factors that would affect the protein structure and lead to aggregation and degradation of the protein.

A. Method for Developing a Buffer Stabilizing System

The present disclosure provides for buffer stabilizing systems that have been shown to unexpectedly preserve protein structure and immunogenicity while preventing aggregation and degradation. The disclosed stabilizing systems may include multiple components including, but not limited to, a buffer, a salt, a sugar, an antioxidant, an amino acid, a reducing agent, and/or any combination thereof. Additional description related to each component is provided below.

1. Carbohydrates or Sugars

Hydrophobic Effect: The major driving force in protein folding is the hydrophobic effect. This is the tendency for hydrophobic molecules to isolate themselves from contact with water. As a consequence during protein folding the hydrophobic side chains become buried in the interior of the protein. The exact physical explanation of the behavior of hydrophobic molecules in water is complex and can best be described in terms of their thermodynamic properties. Much of what is known about the hydrophobic effect has been derived from studying the transfer of hydrocarbons from the liquid phase into water; indeed the thermodynamics of protein folding closely follow the behavior of simple hydrophobic molecules in water. Minimizing the number of hydrophobic side-chains exposed to water is an important driving force behind the folding process. Formation of intramolecular hydrogen bonds provides another important contribution to protein stability. The strength of hydrogen bonds depends on their environment, thus H-bonds enveloped in a hydrophobic core contribute more than H-bonds exposed to the aqueous environment to the stability of the native state.

Important intramolecular bonds can be established in a buffer stabilized system of the present disclosure through the addition of water bonders, such as carbohydrates or sugars. In preferred embodiments, the water bonding sugars of the disclosed methods may include, but are not limited to, trehalose, sucrose, glycerol, mannitol, simple sugars, monosaccharides, disaccharides, oligosaccharides, or sugar alcohols like DMSO, ethylene glycol, propylene glycol, and glycerol, as well as sucrose, lactose, maltose, glucose, and polyethylene glycol, hydroxypropyl-β-cyclodextrin (HPβCD), poly(ethylene glycol) (PEG) of different molecular weights, and polymers like carboxylated poly-L-lysine, polyvinylpyrrolidone (PVP), or low molecular weight polyvinyl alcohol and polyglycerol, called X-1000 and Z-1000. In a particularly preferred embodiment, the sugar is trehalose. The incorporation of sugars into the disclosed methods aids in protection of rPA native conformation, alters tonicity, and alters osmolality.

Sugars may be included in the system in various concentrations that can be determined by one of skill in the art. For instance, in certain embodiments of the disclosed methods, the concentration of a sugar will be about 2.5%, about 5%, about 10%, about 15%, about 20%, or about 25%. Thus, the concentration of a chosen sugar in the disclosed methods may be about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, about 25, about 25.5, about 26.5, about 27, about 27.5, about 28, about 28.5, about 29, about 29.5, about 30, about 30.5, about 31, about 31.5, about 32, about 32.5, about 33, about 33.5, about 34, about 34.5, about 35, about 35.5, about 36, about 36.5, about 37, about 37.5, about 38, about 38.5, about 39, about 39.5, about 40, about 40.5, about 41, about 41.5, about 42, about 42.5, about 43, about 43.5, about 44, about 44.5, about 45, about 45.5, about 46, about 46.5, about 47, about 47.5, about 48, about 48.5, about 49, about 49.5, about 50%, or any amount in-between these values. Alternatively, the sugar can be present in an amount selected from the group consisting of about 2.5% up to about 40%, or any amount in between, such as about 4%, about 5%, about 6%, about 7%, about 8%, about 9%, about 10%, about 12%, about 13%, about 14%, about 15%, about 16%, about 17%, about 18%, about 19%, about 20%, about 25%, about 30%, about 35%, about 40%, about 45% or about 50%%, or any amount in-between these values.

2. Buffers

Figure 2:
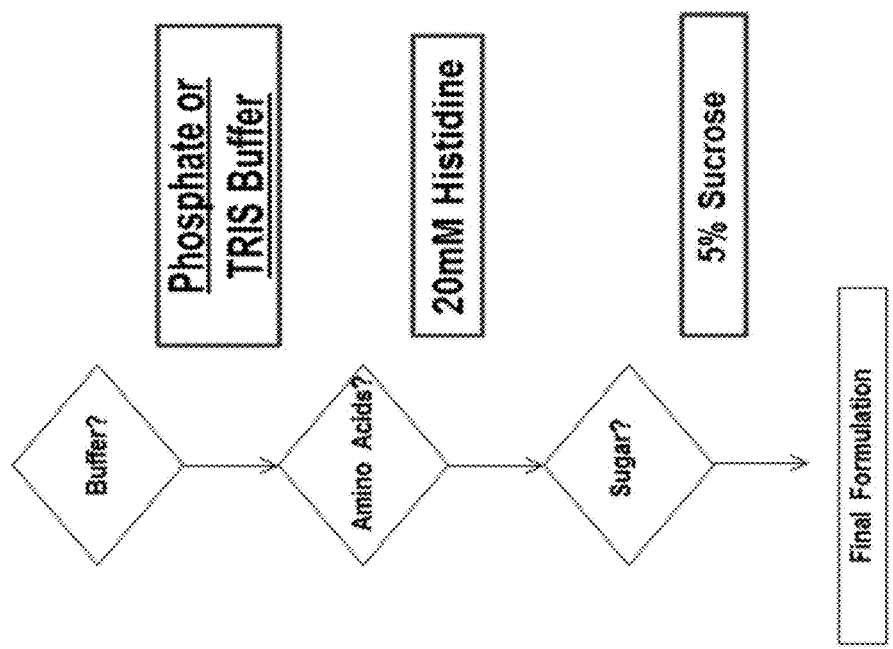
FIG. 2 shows a flowchart of Prototype 1.

Hydrogen Bonds: Hydrogen bonds are primarily electrostatic in nature and involve an interaction between a hydrogen attached to an electronegative atom and another electronegative acceptor atom (A) that carries a lone pair of electrons. In biological systems the electronegative atoms in both cases are usually nitrogen or oxygen. Many of the hydrogen bonds in proteins occur in networks where each donor participates in multiple interactions with acceptors and each acceptor interacts with multiple donors. This is consistent with the ionic nature of hydrogen bonds in proteins. An example of a proposed stabilization flowchart relating to stabilization of hydrogen bonds is shown in FIG. 2.

Protein stability is the difference in free energy between the unfolded state and the folded state. In the unfolded state the polar components are able to form perfectly satisfactory hydrogen bonds to water that are equivalent to those found in the tertiary structure of the protein. Thus, hydrogen bonding is energetically neutral with respect to protein stability, with the caveat that any absences of hydrogen bonding in a folded protein are thermodynamically highly unfavorable.

Optimal hydrogen bonding and a stabilizing balance of free energy can be established in a buffer stabilized system of the present disclosure through the choice of a buffer. In preferred embodiments, the buffers of the disclosed methods may include, but are not limited to, phosphate buffer saline (PBS) and tris(hydroxymethyl)aminomethane (TRIS). Additional buffers suitable for use in the disclosed stabilizing systems include Bis-TRIS (2-bis[2-hydroxyethyl]amino-2-hydroxymethyl-1,3-propanediol), ADA (N-[2-acetamido]-2-iminodiacetic acid), ACES (2-[2-acetamino]-2-aminoethanesulphonic acid), PIPES (1,4-piperazinediethanesulphonic acid), MOPSO (3[N-morpholino]-2-hydroxypropanesulphonic acid), Bis-TRIS PROPANE (1,3 bis[tris(hydroxymethyl)methylaminopropane]), BES (N,N-bis[2-hydroxyethyl]-2-aminoethanesulphonic acid), MOPS (3-[N-morpholino]propanesulphonic acid), TES (2-[2-hydroxy-1,1-bis(hydroxymethyl)ethylamino]ethanesulphonic acid), HEPES (N-[2-hydroxyethyl] piperazine-N'-(2-ethanesulphonic) acid), DIPSO (3-N,N-bis [2-hydroxyethyl]amino-2-hydroxypropanesulphonic) acid), MOBS (4-N-morpholinobutanesulphonic acid), TAPSO (3[N-tris-hydroxymethyl-methylamino]-2-hydroxypropanesulphonic acid), TRIS (2-amino-2-[hydroxymethyl]-1,3-propanediol), HEPPSO (N[2-hydroxyethyl]piperazine-N'-[2-hydroxypropanesulphonic] acid), POPSO (piperazine-N, N'-bis[2-hydroxypropanesulphonic] acid), TEA (triethanolamine), EPPS (N-[2-hydroxyethyl]-piperazine-N-[3-propanesulphonic] acid), TRICINE (N-tris[hydroxymethyl]methylglycine), GLY-GLY (diglycine), BICINE (N,N-bis[2-hydroxyethyl]-glycine), HEPBS (N-[2-hydroxyethyl] piperazine-N'-[4-butanesulphonic] acid), TAPS (N-tris [hydroxymethyl]methyl-3-aminopropanesulphonic] acid), AMPD (2-amino-2-methyl-1,3-propanediol), TABS (N-tris [hydroxymethyl]methyl-4-aminobutanesulphonic acid), AMPSO (3-[(1,1-dimethyl-2-hydroxyethyl)amino]-2-hydroxypropanesulphonic acid), CHES (2-(N-cyclohexylamino)ethanesulphonic acid), CAPSO (3-[cyclohexylamino]-2-hydroxy-1-propanesulphonic acid), AMP (2-amino-2-methyl-1-propanol), CAPS (3-cyclohexylamino-1-propanesulphonic acid) or CABS (4-[cyclohexylamino]-1-butanesulphonic acid), preferably AMPD, TABS, AMPSO, CHES, CAPSO, AMP, CAPS or CABS. The choice of the at least one utilized buffer in the disclosed methods and compositions aids in controlling the pH of the system, optimizing solubility based on the Isoelectric Point (pI) of the protein or peptide of interest, and buffering components to control pH (effects the pI). In particularly preferred embodiments, the buffer is a TRIS buffer. The choice of the utilized buffer in the disclosed methods aids in controlling the pH of the system, optimizing solubility based on the Isoelectric Point (pI) of the protein or peptide of interest, and buffering components to control pH (effects the pI).

Buffers included in the disclosed systems may be in various concentrations that can be determined by one of skill in the art. For instance, in certain embodiments of the disclosed methods, the concentration of a buffer will be about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, or about 150 mM, or any amount in-between these values. For instance, in exemplary embodiments utilizing a PBS buffer system, the concentration may be 10 mM PBS. Alternatively, in exemplary embodiments utilizing a TRIS buffer system, the concentration may be 10 mM TRIS or 80 mM TRIS.

Additionally, pH of the buffer system is important to achieving and maintaining ideal protein stabilization. Buffers included in the disclosed systems may be set at various pH levels that can be determined by one of skill in the art. For instance, in certain embodiments of the disclosed methods, the pH of a buffer will be about 5, about 5.5, about 6, about 6.5, about 7, about 7.5, about 8, or about 8.5, about 9, about 9.5, or about 10. Thus, the pH of a chosen buffer in the disclosed methods may be about 5.0, about 5.1, about 5.2, about 5.3, about 5.4, about 5.5, about 5.6, about 5.7, about 5.8, about 5.9, about 6.0, 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10. For instance, in exemplary embodiments utilizing a PBS buffer system, the pH may be about 7.4. Alternatively, in exemplary embodiments utilizing a TRIS buffer system, the pH may be about 8.0.

3. Reducing Agents

Figure 3:
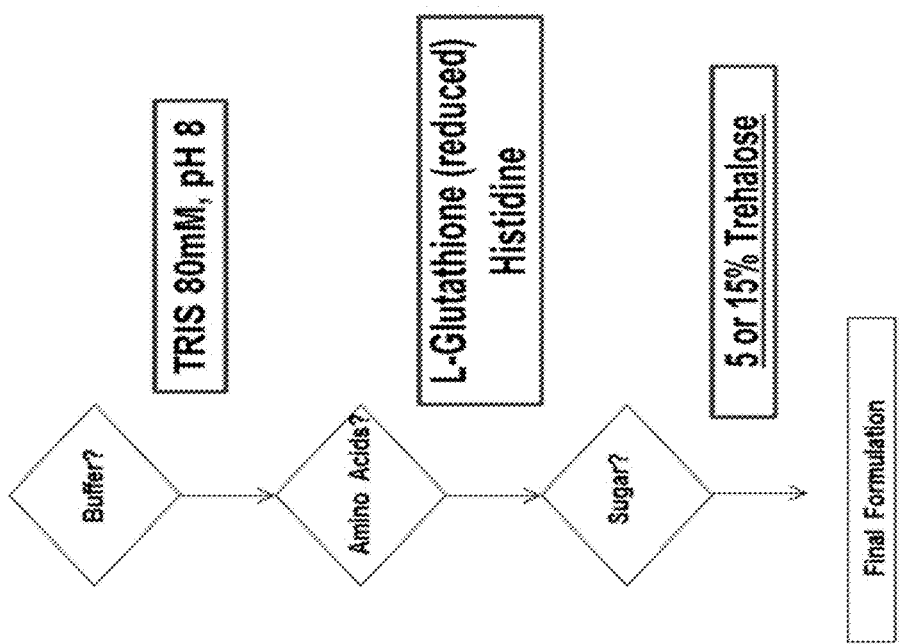
FIG. 3 shows a flowchart of Prototype 2.

Disulfide Bonds: Many extracellular proteins contain disulfide bonds. In these proteins the presence of disulfide bonds adds considerable stability to the folded state where in many cases reduction of the cystine linkages is sufficient to induce unfolding. The source of the stability appears to be entropic rather than enthalpic. The introduction of a disulfide bond reduces the entropy of the unfolded state by reducing the degrees of freedom available to the disordered polypeptide chain. This stabilizes the folded state by decreasing the entropy difference between the folded and unfolded state. An example of a proposed stabilization flowchart relating to stabilization of disulfide bonds is shown in FIG. 3.

Important disulfide bonds can be strengthened or established in a buffer stabilized system of the present disclosure through the addition of reducing. Reducing agents suitable for use in the disclosed stabilizing systems include, but are not limited to, pharmaceutically acceptable reducing agent like cysteine, glutathione, a combination of glutathione and glutathione S-transferase, Dithiothreitol (DTT), cysteamine, thioredoxin, N-acetyl-L-cysteine (NAC), alpha-lipoic acid, 2-mercaptoethanol, 2-mercaptoethanesulfonic acid, mercapto-propionyglycine, tris(2-carboxyethyl)phophine (TCEP) and combinations thereof. EDTA, as a chelating agent, may inhibit the metal-catalyzed oxidation of the sulfhydryl groups, thus reducing the formation of disulfide-linked aggregates. A preferred concentration of EDTA is 0.001-0.5%, more preferably 0.005-0.4%, more preferably 0.0075-0.3%, or even more preferably 0.01-0.2%.

4. Salts

Ionic Interactions: The association of two oppositely charged ionic groups in a protein is known as a salt bridge or ion pair and is a common feature of most proteins. Typically these interactions contribute very little to protein stability since the isolated ionic groups are so effectively solvated by water. As a consequence very few un-solvated salt bridges are found in the interior of proteins.

Important ionic interactions can be strengthened or established in a buffer stabilized system of the present disclosure through the addition of salts. In preferred embodiments, the salts utilized in the disclosed methods may include, but are not limited to, sodium chloride, sodium succinate, sodium sulfate, potassium chloride, magnesium chloride, magnesium sulfate, and calcium chloride. The incorporation of salts into the disclosed methods aids in increasing the surface tension of water ionic strength and optimizing ionic strength, particularly in instances when stabilizing an ion-dependent folding of the protein domain (e.g. rPA has calcium-dependent binding domains).

Salts may function as tonicity modifiers, which contributes to the isotonicity of the formulations, and may be added to the disclosed compositions. The tonicity modifier useful for the present invention include the salts listed above.

One or more salts may be included in the disclosed systems in various concentrations that can be determined by one of skill in the art. For instance, in certain embodiments of the disclosed methods, the concentration of an amino acid will be about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, or any amount in-between these values. For instance, in exemplary embodiments utilizing a sodium chloride, the concentration may be about 100-about 150 mM. In exemplary embodiments utilizing calcium chloride, the concentration may be about 100-about 150 mM. Thus, for example, the concentration of a chosen salt in the disclosed methods may be about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200 mM, or any amount in-between these values. In exemplary embodiments utilizing magnesium chloride, the concentration may be about 1 about 150 mM. Thus, for example, the concentration of a chosen salt in the disclosed methods may be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100 mM, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, or any amount in-between these values.

Preferred salts for this invention include NaCl and $MgCl_2$. A preferred concentration of NaCl is about 75-150 mM. A preferred concentration of $MgCl_2$ is about 1-150 mM.

5. Amino Acids

Figure 4:
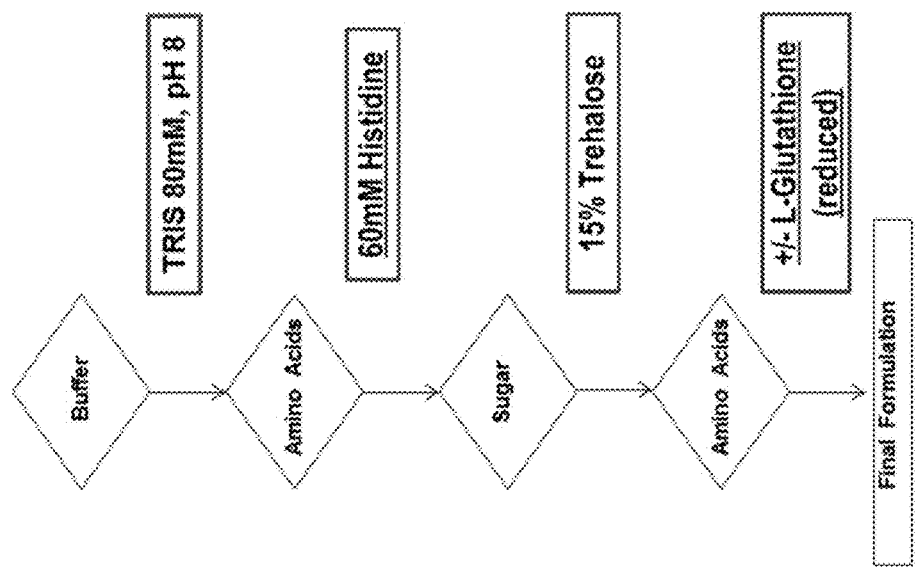
FIG. 4 shows a flowchart of Prototype 3.

Dipole-Dipole Interactions: Dipole-dipole interactions are weak interactions that arise from the close association of permanent or induced dipoles. Collectively these forces are known as Van der Waals interactions. Proteins contain a large number of these interactions, which vary considerably in strength. The strongest interactions are observed between permanent dipoles and are an important feature of the peptide bond. London or dispersion forces are the weakest of all of the dipole-dipole. As a group, the Van der Waals forces are important for stabilizing interactions between proteins and their complementary ligands whether the ligands are proteins or small molecules. An example of a proposed stabilization flowchart relating to stabilization of dipole-dipole interactions is shown in FIG. 4.

Important dipole-dipole interactions can be strengthened or established in a buffer stabilized system of the present disclosure through the addition of amino acids. In preferred embodiments, the amino acids utilized in the disclosed methods may include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. Modified and/or synthetic forms of amino acids can also be utilized in the methods and compositions of the disclosure, for example, non-naturally encoded amino acids include, but are not limited to, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α di-substituted amino acid; a β-amino acid; and a cyclic amino acid other than proline. In particularly preferred embodiments, the amino acid may be histidine, glutathione, or alanine. In an even more preferred embodiment, the amino acid is histidine. The incorporation of amino acids into the disclosed methods aids in directing protein binding, buffering capacity, and antioxidant properties, as well as suppressing the aggregation of folding intermediates, radical attacks by reactive oxygen and nitrogen species, and preventing denaturation.

Like the salts discussed above, amino acids can also be considered tonicity modifiers. Amino acids that are pharmaceutically acceptable and suitable for this purpose include proline, alanine, L-arginine, asparagine, L-aspartic acid, glycine, serine, lysine, and histidine. A preferred amino acid for this invention is histidine. A preferred concentration of histidine is roughly 5-80 mM.

Amino acids may be included in the disclosed systems in various concentrations that can be determined by one of skill in the art. For instance, in certain embodiments of the disclosed methods, the concentration of an amino acid will be about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. For instance, in exemplary embodiments utilizing a glutathione, the concentration may be about 16 mM glutathione. In exemplary embodiments utilizing histidine, the concentration may be about 20 mM or about 60 mM histidine. In exemplary embodiments utilizing an alanine, the concentration may be about 10 mM alanine. Thus, the concentration of a chosen amino acid in the disclosed methods may be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100 mM, or any amount in-between these values.

The methods disclosed herein can be utilized in developing, optimizing, and formulating the vaccine compositions described below.

B. Nanoemulsion Stabilization of the rPA Antigen

One of the most common formulation strategies used in vaccine development is to adsorb an antigen (e.g. protein) onto an aluminum salt adjuvant. Electrostatic interactions and phosphate exchange are two of the most important mechanisms for the adsorption of antigens onto aluminum-containing adjuvants. It is intuitively attractive that adsorption should have effects on protein structure. Although aluminum-containing adjuvants have been in use in vaccine formulations for nearly a century, it has only been recently that investigations into the direct effects of antigen adsorption on antigen conformation and stability have begun. Adsorption of antigens onto an adjuvant has recently been suggested to decrease the thermal stability of some antigens. In another embodiment of the invention, described is a vaccine comprising a nanoemulsion adjuvant and a stabilized protein antigen, or stabilized carrier protein. The nanoemulsion adjuvant can further aid in stabilization of the component protein. Nanoemulsions are known in the art and are described in, for example, U.S. Pat. Nos. 6,506,803; 6,015,832; 6,559,189; 6,635,676; 7,314,624; 7,655,252; 7,767,216; 8,232,320; 8,236,335; 8,226,965; 8,703,164; 8,747,872; 8,771,731; 8,877,208; 8,668,911; 8,962,026; and 9,131,680, all of which are specifically incorporated by reference.

III. Anthrax Vaccine Compositions

The vaccine compositions of the present disclosure comprise rPA combined with a nanoemulsion and a protein-stabilizing buffer system.

The present disclosure is directed, in part, to novel, optimized compositions to stabilize the secondary and tertiary structures of rPA in a buffer stabilizing solution as well as a nanoemulsion adjuvant.

A. Buffer Stabilizing System for rPA Vaccine Compositions

The disclosed buffer stabilized protein compositions comprise at least one protein or peptide of interest, a buffer, a salt, a sugar, an antioxidant, an amino acid, or a combination thereof. Exemplary components (i.e. buffers, salts, sugars, antioxidants, and amino acids) are disclosed throughout the specification and the examples. The disclosed compositions have been demonstrated to unexpected stabilize proteins and peptides in solution over extended periods of time, even when introduced to stressor that can potentially cause denaturation or aggregation, such as heat.

In one embodiment of the disclosed composition, the stabilizing buffer system comprises: (1) a TRIS (tris(hydroxymethyl)aminomethane) buffer or a PBS buffer; (2) at least one salt, such as sodium chloride or calcium chloride; (3) at least one sugar, such as trehalose and sucrose; (4) at least one amino acid, such as histidine, alanine, or glutathione; or (5) any combination thereof.

In some embodiments, the pH of composition is between about 5 to about 10, between about 6 to about 9, or between about 7 to about 8. For instance, the pH of a disclosed buffer stabilized composition may be about 5.0, about 5.1, about 5.2, about 5.3, about 5.4, about 5.5, about 5.6, about 5.7, about 5.8, about 5.9, about 6.0, 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10.

In another embodiment, the disclosed compositions sugar. Preferred sugars include, but are not limited to, trehalose and sucrose. In preferred embodiments, the sugar can be trehalose. The sugar can be present in an amount selected from the group consisting of about 2.5% up to about 40%, or any amount in between, such as about 4%, about 5%, about 6%, about 7%, about 8%, about 9%, about 10%, about 12%, about 13%, about 14%, about 15%, about 16%, about 17%, about 18%, about 19%, about 20%, about 25%, about 30%, about 35%, or about 45%. In other embodiments of the disclosed compositions, the concentration of a sugar will be about 2.5%, about 5%, about 10%, about 15%, or about 20%. Thus, the concentration of a chosen sugar in the disclosed methods may be about 1, about 1.5 about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, about 25%, or any amount in-between these values.

Salts may be included in the disclosed systems in various concentrations that can be determined by one of skill in the art. For instance, in certain embodiments of the disclosed compositions, the concentration of an amino acid will be about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, or about 200 mM. For instance, in exemplary embodiments utilizing a sodium chloride, the concentration may be about 100-150 mM. In exemplary embodiments utilizing calcium chloride, the concentration may be about 100-150 mM. Thus, the concentration of a chosen salt in the disclosed compositions may be about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200 mM, or any amount in-between these values.

Important dipole-dipole interactions can be strengthened or established in a buffer stabilized system of the present disclosure through the addition of amino acids. In preferred embodiments, the amino acids utilized in the disclosed methods may include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. Modified and/or synthetic forms of amino acids can also be utilized in the methods and compositions of the disclosure, for example, non-naturally encoded amino acids include, but are not limited to, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α,α di-substituted amino acid; a β-amino acid; and a cyclic amino acid other than proline. In particularly preferred embodiments, the amino acid may be histidine, glutathione, or alanine. In even more preferred embodiments, the amino acid can be histidine. The incorporation of amino acids into the disclosed compositions aids in directing protein binding, buffering capacity, and antioxidant properties, as well as suppressing the aggregation of folding intermediates, radical attacks by reactive oxygen and nitrogen species, and preventing denaturation.

Amino acids may be included in the disclosed systems in various concentrations that can be determined by one of skill in the art. For instance, in certain embodiments of the disclosed methods, the concentration of an amino acid will be about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. For instance, in exemplary embodiments utilizing a glutathione, the concentration may be about 16 mM glutathione. In exemplary embodiments utilizing histidine, the concentration may be about 20 mM or about 60 mM histidine. In exemplary embodiments utilizing a alanine, the concentration may be about 10 mM alanine. Thus, the concentration of a chosen amino acid in the disclosed compositions may be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100 mM, or any amount in-between these values.

Additional compounds suitable for use in the disclosed compositions include, but are not limited to, one or more solvents, such as an organic phosphate-based solvent, bulking agents, coloring agents, pharmaceutically acceptable excipients, a preservative, pH adjuster, buffer, chelating agent, etc. The additional compounds can be admixed into a previously formulated composition, or the additional compounds can be added to the original mixture to be further formulated. In certain of these embodiments, one or more additional compounds are admixed into an existing disclosed composition immediately prior to its use. Such additional ingredients include, but are not limited to, those listed above in Section C—Novel Methods to Stabilized Proteins.

In some embodiments, the disclosed buffer stabilized compositions will further comprise at least one reducing agent. Reducing agents suitable for use in the disclosed composition are known in the art., and can be important for strengthening or establishing disulfide bonds in a buffer stabilized system. Reducing agents suitable for use in the disclosed stabilizing systems include, but are not limited to, pharmaceutically acceptable reducing agent like cysteine, glutathione, a combination of glutathione and glutathione S-transferase, Dithiothreitol (DTT), cysteamine, thioredoxin, N-acetyl-L-cysteine (NAC), alpha-lipoic acid, 2-mercaptoethanol, 2-mercaptoethanesulfonic acid, mercapto-propionyglycine, tris(2-carboxyethyl)phophine (TCEP) and combinations thereof. EDTA, as a chelating agent, may inhibit the metal-catalyzed oxidation of the sulfhydryl groups, thus reducing the formation of disulfide-linked aggregates. A preferred concentration of EDTA is about 0.001-about 0.5%, more preferably about 0.005-about 0.4%, more preferably about 0.0075-about 0.3%, or even more preferably about 0.01-about 0.2%.

Stability of the protein (i.e. rPA) can be evaluated by one or more of the following factors: (1) evaluating the physical, chemical, and/or biological stability of the protein; (2) determining whether protein aggregates or particulates are present; (3) determining whether the protein is susceptible to or undergoing denaturation; (4) evaluating the thermostability of the protein by exposing the proteins to an elevated temperature and determining whether the protein denatures or changes in concentration by more than about 10%, about 15%, about 20%, about 25%, about 30%, about 35%, about 40%, about 45%, or about 50%; (5) measuring protein concentration to determine if the concentration changes over time, demonstrating protein instability. For example, if the protein concentration changes by more than 10%, about 15%, about 20%, about 25%, about 30%, about 35%, about 40%, about 45%, or about 50% over time, then this is evidence of protein instability; (6) evaluating the color of a disclosed composition comprising a stabilized protein, where a white to off white color is acceptable and a yellow (light to dark), tan, and shades of brown are not acceptable as the indicate protein instability; and/or (7) evaluating a composition comprising a stabilized protein to determine if the particle size changes significantly over time, which is evidence of an unstable composition (e.g., changes by more than about 10%, about 15%, about 20%, about 25%, about 30%, about 35%, about 40%, about 45%, or about 50% time time).

B. Nanoemulsion Adjuvant

As noted above, the stabilized protein antigen (rPA) of the disclosure can be incorporated into a nanoemulsion vaccine adjuvant. A nanoemulsion vaccine adjuvant comprises a stabilized antigen, or stabilized carrier protein coupled to an antigen, and a nanoemulsion. The nanoemulsion can comprise an aqueous phase, at least one oil, at least one surfactant, and at least one solvent. Nanoemulsions of the present disclosure may comprise the following properties and components.

1. Nanoemulsion Droplet Size

The nanoemulsion vaccine of the present disclosure comprises droplets having a mean (z-average) particle size diameter of less than or equal to about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or any combination thereof or any amount in-between these values. In one embodiment, the droplets have a mean (z-average) particle size diameter greater than about 125 nm and less than or equal to about 600 nm. In a different embodiment, the droplets have a mean (z-average) particle size diameter greater than about 50 nm or greater than about 70 nm, and less than or equal to any particle size disclosed herein, or less than or equal to about 180 nm.

2. Aqueous Phase

The aqueous phase can comprise any type of aqueous phase including, but not limited to, water (e.g., $H_2O$, distilled water, purified water, water for injection, de-ionized water, tap water) and solutions (e.g., phosphate buffered saline (PBS) solution). In certain embodiments, the aqueous phase comprises water at a pH of about 4 to about 10, preferably about 6 to about 8. The water can be deionized (hereinafter "$DiH_2O$"). In some embodiments the aqueous phase comprises phosphate buffered saline (PBS). The aqueous phase may further be sterile and pyrogen free.

3. Organic Solvents

Organic solvents in the nanoemulsion vaccines of the disclosed include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the disclosed, the organic solvent is an alcohol chosen from a nonpolar solvent, a polar solvent, a protic solvent, or an aprotic solvent.

Suitable organic solvents for the nanoemulsion RSV vaccine include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

4. Oil Phase

The oil in the nanoemulsion vaccine of the disclosed can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof.

In one aspect of the disclosed, the volatile oil in the silicone component is different than the oil in the oil phase.

5. Surfactants

The surfactant in the nanoemulsion vaccine of the disclosed can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in *Applied Surfactants: Principles and Applications* (Tharwat F. Tadros, Copyright August 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thiglycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isoproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2 CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN®

80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl (tetradecyl)ammonium bromide, 1,3,5-Triazine-1,3,5(2H,4H,6H)-triethanol, 1-Decanaminium, N-decyl-N,N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Alkyl 1 or 3 benzyl-1-(2-hydroxethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% $C_{12}$), Alkyl dimethyl 3,4-dichlorobenzyl ammonium chloride (50% $C_{14}$, 40% $C_{12}$, 10% $C_{16}$), Alkyl dimethyl 3,4-dichlorobenzyl ammonium chloride (55% $C_{14}$, 23% $C_{12}$, 20% $C_{16}$), Alkyl dimethyl benzyl ammonium chloride, Alkyl dimethyl benzyl ammonium chloride (100% $C_{14}$), Alkyl dimethyl benzyl ammonium chloride (100% $C_{16}$), Alkyl dimethyl benzyl ammonium chloride (41% $C_{14}$, 28% $C_{12}$), Alkyl dimethyl benzyl ammonium chloride (47% $C_{12}$, 18% $C_{14}$), Alkyl dimethyl benzyl ammonium chloride (55% C16, 20% $C_{14}$), Alkyl dimethyl benzyl ammonium chloride (58% $C_{14}$, 28% $C_{16}$), Alkyl dimethyl benzyl ammonium chloride (60% $C_{14}$, 25% $C_{12}$), Alkyl dimethyl benzyl ammonium chloride (61% $C_{11}$, 23% $C_{14}$), Alkyl dimethyl benzyl ammonium chloride (61% $C_{12}$, 23% $C_{14}$), Alkyl dimethyl benzyl ammonium chloride (65% $C_{12}$, 25% $C_{14}$), Alkyl dimethyl benzyl ammonium chloride (67% $C_{12}$, 24% $C_{14}$), Alkyl dimethyl benzyl ammonium chloride (67% $C_{12}$, 25% $C_{14}$), Alkyl dimethyl benzyl ammonium chloride (90% $C_{14}$, 5% $C_{12}$), Alkyl dimethyl benzyl ammonium chloride (93% $C_{14}$, 4% $C_{12}$), Alkyl dimethyl benzyl ammonium chloride (95% $C_{16}$, 5% $C_{18}$), Alkyl dimethyl benzyl ammonium chloride, Alkyl didecyl dimethyl ammonium chloride, Alkyl dimethyl benzyl ammonium chloride, Alkyl dimethyl benzyl ammonium chloride ($C_{12-16}$), Alkyl dimethyl benzyl ammonium chloride ($C_{12-18}$), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% $C_{14}$, 5% $C_{16}$, 5% $C_{12}$), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% $C_{14}$), Alkyl dimethyl isopropylbenzyl ammonium chloride (50% $C_{12}$, 30% $C_{14}$, 17% $C_{16}$, 3% $C_{18}$), Alkyl trimethyl ammonium chloride (58% $C_{18}$, 40% $C_{16}$, 1% $C_{14}$, 1% $C_{12}$), Alkyl trimethyl ammonium chloride (90% $C_{18}$, 10% $C_{16}$), Alkyldimethyl (ethylbenzyl) ammonium chloride ($C_{12-18}$), Di-($C_{8-10}$)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present disclosed are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio)propanesulfonate inner salt, 3-(N,N-Dimethylpalmitylammonio)propanesulfonate, semi-synthetic derivatives thereof, and combinations thereof.

In some embodiments, the nanoemulsion vaccine comprises a cationic surfactant, which can be cetylpyridinium chloride. In other embodiments of the disclosed, the nanoemulsion vaccine comprises a cationic surfactant, and the concentration of the cationic surfactant is less than about 5.0% and greater than about 0.001%. In yet another embodiment of the disclosed, the nanoemulsion vaccine comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion vaccine is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion vaccine is less than about 5.0% and greater than about 0.001%.

In another embodiment of the disclosed, the nanoemulsion vaccine comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.01% to about 5.0%, or the non-ionic surfactant is present in a concentration of about 0.1% to about 3%. In yet another embodiment of the disclosed, the nanoemulsion vaccine comprises a cationic surfactant present in a concentration of about 0.01% to about 2%, in combination with a nonionic surfactant.

6. Additional Ingredients

Additional compounds suitable for use in the nanoemulsion vaccines of the disclosed include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion vaccine, or the additional compounds can be added to the original mixture to be emulsified. In certain of these embodiments, one or more additional compounds are admixed into an existing nanoemulsion composition immediately prior to its use.

Suitable preservatives in the nanoemulsion vaccines of the disclosed include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophenol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis (p-chlorophenyldiguanido) hexane), chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion vaccine may further comprise at least one pH adjuster. Suitable pH adjusters in the nanoemulsion vaccine of the disclosed include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion vaccine can comprise a chelating agent. In one embodiment of the disclosed, the chelating agent is present in an amount of about 0.0005% to about 1%. Examples of chelating agents include, but are not limited to, ethylenediamine, ethylenediaminetetraacetic acid (EDTA), phytic acid, polyphosphoric acid, citric acid, gluconic acid, acetic acid, lactic acid, and dimercaprol, and a preferred chelating agent is ethylenediaminetetraacetic acid.

The nanoemulsion vaccine can comprise a buffering agent, such as a pharmaceutically acceptable buffering agent. Examples of buffering agents include, but are not limited to, 2-Amino-2-methyl-1,3-propanediol, ≥99.5% (NT), 2-Amino-2-methyl-1-propanol, ≥99.0% (GC), L-(+)-Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in $H_2O$ (colorless solution at 20° C.), Ammonium tartrate dibasic, ≥99.5% (T), BES buffered saline, for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, >0.1 M $Na_2CO_3$, >0.2 M $NaHCO_3$, Boric acid, ≥99.5% (T), Boric acid, for molecular biology, ≥99.5% (T), CAPS, ≥99.0% (TLC), CHES, ≥99.5% (T), Calcium acetate hydrate, ≥99.0% (calc. on dried material, KT), Calcium carbonate, precipitated, ≥99.0% (KT), Calcium citrate tribasic tetrahydrate, ≥98.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in $H_2O$, Gly-Gly-Gly, ≥99.0% (NT), Gly-Gly, ≥99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, ≥99.5% (T), Imidazole buffer Solution, 1 M in $H_2O$, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS, for molecular biology, ≥99.5% (T), Magnesium acetate solution, for molecular biology, ~1 M in $H_2O$, Magnesium acetate tetrahydrate, ≥99.0% (KT), Magnesium citrate tribasic nonahydrate, ≥98.0% (calc. based on dry substance, KT), Magnesium formate solution, 0.5 M in $H_2O$, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, Piperazine, anhydrous, ≥99.0% (T), Potassium D-tartrate monobasic, ≥99.0% (T), Potassium acetate solution, for molecular biology, Potassium acetate solution, for molecular biology, 5 M in $H_2O$, Potassium acetate solution, for molecular biology, ~1 M in $H_2O$, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in $H_2O$, Potassium formate solution, 14 M in $H_2O$, Potassium formate, ≥99.5% (NT), Potassium oxalate monohydrate, ≥99.0% (RT), Potassium phosphate dibasic, anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in $H_2O$, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in $H_2O$, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in $H_2O$, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in $H_2O$, Sodium oxalate, ≥99.5% (RT), Sodium phosphate dibasic dihydrate, ≥99.0% (T), Sodium phosphate dibasic dihydrate, for luminescence, ≥99.0% (T), Sodium phosphate dibasic dihydrate, for molecular biology, ≥99.0% (T), Sodium phosphate dibasic dodecahydrate, ≥99.0% (T), Sodium phosphate dibasic solution, 0.5 M in $H_2O$, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in $H_2O$, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in $H_2O$ (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate-EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, Tricine, ≥99.5% (NT), Triethanolamine, ≥99.5% (GC), Triethylamine, ≥99.5% (GC), Triethylammonium acetate buffer, volatile buffer, ~1.0 M in H$_2$O, Triethylammonium phosphate solution, volatile buffer, ~1.0 M in H$_2$O, Trimethylammonium acetate solution, volatile buffer, ~1.0 M in H$_2$O, Trimethylammonium phosphate solution, volatile buffer, ~1 M in H$_2$O, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion vaccine can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present disclosure feature nanoemulsion vaccines that may readily be diluted with water or another aqueous phase to a desired concentration without impairing their desired properties.

7. Immune Modulators

As noted above, the vaccine can further comprise one or more immune modulators. Examples of immune modulators include, but are not limited to, chitosan, glucan, enterotoxin, nucleic acid (CpG motifs), MF59, alum, ASO system, etc. It is within the purview of one of ordinary skill in the art to employ suitable immune modulators in the context of the present disclosure.

An immune modulator can be present in the vaccine composition at any pharmaceutically acceptable amount including, but not limited to, from about 0.001% up to about 10%, and any amount in between, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%.

8. Exemplary Nanoemulsions

An exemplary nanoemulsion adjuvant composition according to the invention is designated "W$_{80}$5EC" adjuvant. The composition of W$_{80}$5EC adjuvant is shown in Table 1. The mean droplet size for the W$_{80}$5EC adjuvant is ~400 nm. All of the components of the nanoemulsion are included on the FDA inactive ingredient list for Approved Drug Products.

TABLE 1

| W$_{80}$5EC Formulation | |
| --- | --- |
| Function | W$_{80}$5EC-Adjuvant Mean Droplet Size ≈400 nm |
| Aqueous Diluent | Purified Water, USP |
| Hydrophobic Oil (Core) | Soybean Oil, USP (super refined) |
| Organic Solvent | Dehydrated Alcohol, USP (anhydrous ethanol) |

TABLE 1-continued

| W$_{80}$5EC Formulation | |
| --- | --- |
| Function | W$_{80}$5EC-Adjuvant Mean Droplet Size ≈400 nm |
| Surfactant | Polysorbate 80, NF |
| Emulsifying Agent Preservative | Cetylpyridinium Chloride, USP |

The nanoemulsion vaccine adjuvants are formed by emulsification of an oil, purified water, nonionic detergent, organic solvent and surfactant, such as a cationic surfactant. An exemplary specific nanoemulsion adjuvant is designated as "60% W$_{80}$5EC". The 60% W$_{80}$5EC-vaccine adjuvant is composed of the ingredients shown in Table 2 below: purified water, USP; soybean oil USP; Dehydrated Alcohol, USP [anhydrous ethanol]; Polysorbate 80, NF and cetylpyridinium chloride, USP (CPC). All components of this exemplary nanoemulsion adjuvant are included on the FDA list of approved inactive ingredients for Approved Drug Products.

TABLE 2

| Composition of 60% W$_{80}$5EC-Adjuvant (% (w/w)) | |
| --- | --- |
| Ingredients | 60% W$_{80}$5EC |
| Purified Water, USP | 54.10% |
| Soybean Oil, USP | 37.67% |
| Dehydrated Alcohol, USP (anhydrous ethanol) | 4.04% |
| Polysorbate 80, NF | 3.55% |
| Cetylpyridinium Chloride, USP | 0.64% |

For the purposes of the present disclosure, a nanoemulsion as provided here (e.g. W$_{80}$5EC) can make up between 1-99% (% (w/w)) of a vaccine composition of the disclosure. For instance, the nanoemulsion can be about 0.1, about 0.5, about 1, about 2.5, about 5, about 10, about 15, about 20, about 25, about 30, about 35, about 40, about 45, about 50, about 55, about 60, about 65, about 70, about 75, about 80, about 85, about 90, about 95, or about 99% of a vaccine formulation of the disclosure. Additionally, the percent of nanoemulsion in a vaccine composition may differ depending on the route of administration. For instance, a vaccine for intramuscular (IM) injection may be about 1, about 2.5, about 5, about 10, or about 15% W$_{80}$5EC, or any value in between. Alternatively, a vaccine for intranasal (IN) administration may be about 5, about 10, about 20, about 30, or about 40% W$_{80}$5EC, or any value in between.

IV. Pharmaceutical rPA Compositions

The rPA vaccine compositions of the present disclosure may be formulated into pharmaceutical compositions, such as a vaccine, that are administered in a therapeutically effective amount to a subject and may further comprise suitable, pharmaceutically-acceptable excipients, additives, or preservatives. Suitable excipients, additives, and preservatives are well known in the art.

By the phrase "therapeutically effective amount" it is meant any amount of the composition that is effective in preventing, treating, or ameliorating a disease, pathogen, malignancy, or condition associated with rPA present in the buffer-stabilized composition. By "protective immune response" it is meant that the immune response is associated with prevention, treating, or amelioration of a disease.

Complete prevention is not required, though is encompassed by the present disclosure. The immune response can be evaluated using the methods discussed herein or by any method known by a person of skill in the art.

The rPA pharmaceutical compositions may be formulated for immediate release, sustained release, controlled release, delayed release, or any combinations thereof, into the epidermis or dermis. In some embodiments, the formulations may comprise a penetration-enhancing agent. Suitable penetration-enhancing agents include, but are not limited to, alcohols such as ethanol, triglycerides and aloe compositions. The amount of the penetration-enhancing agent may comprise from about 0.5% to about 40% by weight of the formulation.

In one aspect of the disclosure, the invention relates to a method for vaccination against, or for prophylaxis or therapy (prevention or treatment) of exposure to, infection with, or poisoning by anthrax (*Bacillus anthracis*) via administration of a therapeutically or prophylactically effective amount of (a pharmaceutical composition comprising) a composition of the disclosure as defined above, or obtainable as defined herein, to a subject in need of prophylaxis or therapy. Preferably, the virions are administered intranasally.

However, the rPA compositions of the present disclosure can be administered by any suitable route of administration. It will also be appreciated that the preferred route will vary with the condition and age of the recipient, and the disease being treated.

For instance, the compositions can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. Non-limiting examples of carriers include phosphate buffered saline (PBS), saline or a biocompatible matrix material such as a decellularized liver matrix (DCM as disclosed in Wang et al. (2014) J. Biomed. Mater Res. A. 102(4):1017-1025) for topical or local administration. The compositions can optionally contain a protease inhibitor, glycerol and/or dimethyl sulfoxide (DMSO).

The rPA compositions can be conveniently presented in dosage unit form and can be prepared by any of the methods well known in the art of pharmacy. The compositions can be, for example, prepared by uniformly and intimately bringing the active ingredient into association with a liquid carrier, a finely divided solid carrier or both, and then, if necessary, shaping the product into the desired formulation. In the composition the protein or peptide is included in an amount sufficient to produce the desired therapeutic effect. For example, pharmaceutical compositions of the disclosure may take a form suitable for virtually any mode of administration, including, for example, topical, ocular, oral, buccal, systemic, nasal, injection, transdermal, rectal, and vaginal, or a form suitable for administration by inhalation or insufflation.

Intranasal administration is a particularly preferred mode of administration that includes administration via the nose, either with or without concomitant inhalation during administration. Such administration is typically through contact by the pharmaceutical composition comprising the nanoemulsion composition with the nasal mucosa, nasal turbinates or sinus cavity. Administration by inhalation comprises intranasal administration, or may include oral inhalation. Such administration may also include contact with the oral mucosa, bronchial mucosa, and other epithelia.

However, the disclosure is not limited to intranasal administration and pharmaceutical compositions of the disclosure may be administered by alternative means, like oral or injectable administration, as well. Useful injectable preparations include sterile suspensions, solutions, or emulsions of the active compound(s) in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g., starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and U.S. Pat. No. 4,265,874 to form osmotic therapeutic tablets for control release. The pharmaceutical compositions of the disclosure may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Exemplary dosage forms for pharmaceutical administration are described herein. Examples include but are not limited to liquids, ointments, creams, emulsions, lotions, gels, bioadhesive gels, sprays, aerosols, pastes, foams, sunscreens, capsules, microcapsules, suspensions, pessary, powder, semi-solid dosage form, etc.

The disclosed buffer-stabilized protein compositions can likewise be applied and/or delivered utilizing electrophoretic delivery/electrophoresis. Further, the compositions may be applied by a transdermal delivery system such as a patch or administered by a pressurized or pneumatic device (i.e., "gene gun"). Such methods, which comprise applying an electrical current, are well known in the art.

The rPA pharmaceutical compositions for administration may be applied in a single administration or in multiple administrations.

If applied topically, the rPA compositions may be occluded or semi-occluded. Occlusion or semi-occlusion may be performed by overlaying a bandage, polyoleofin film, article of clothing, impermeable barrier, or semi-impermeable barrier to the topical preparation.

The present disclosure contemplates that many variations of the described rPA compositions will be useful in the methods of the present disclosure. To determine if a candidate composition is suitable for pharmaceutical use, three criteria are analyzed. Using the methods and standards described herein, candidate compositions can be easily tested to determine if they are suitable. First, the desired ingredients are prepared using the methods described herein, to determine if a buffer-stabilized compositions can be formed. If a buffer-stabilized compositions cannot be formed, the candidate is rejected. Second, the candidate buffer-stabilized compositions should be stable. A buffer-stabilized composition is stable if it remains in solution, with the biological activity of a protein or peptide preserved for a sufficient period to allow for its intended use. For example, for pharmaceutical buffer-stabilized compositions that are to be stored, shipped, etc., it may be desired that the buffer-stabilized composition remain in solution form for months to years. Typical buffer-stabilized compositions that are relatively unstable, will lose their form within a day. Third, the candidate pharmaceutical buffer-stabilized compositions should have efficacy for its intended use. For example, the pharmaceutical buffer-stabilized compositions disclosed herein should induce a protective immune response or a therapeutic effect to a detectable level.

The disclosed compositions can be provided in many different types of containers and delivery systems. For example, in some embodiments of the disclosed, the rPA compositions are provided in a cream or other solid or semi-solid form. The disclosed compositions may be incorporated into hydrogel formulations.

The rPA compositions can be delivered (e.g., to a subject or customers) in any suitable container. Suitable containers can be used that provide one or more single use or multi-use dosages of the vaccines for the desired application. In some embodiments of the disclosed, the compositions are provided in a suspension or liquid form. Such compositions can be delivered in any suitable container including spray bottles and any suitable pressurized spray device. Such spray bottles may be suitable for delivering the compositions intranasally or via inhalation. These containers can further be packaged with instructions for use to form kits.

V. Methods of Manufacture

The nanoemulsion adjuvants of the disclosed can be formed using classic emulsion forming techniques. See e.g., U.S. 2004/0043041. In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the disclosed employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods and compositions of the disclosed comprise droplets of an oily discontinuous phase dispersed in an aqueous continuous phase, such as water or PBS. The nanoemulsions of the disclosed are stable, and do not deteriorate even after long storage periods. Certain nanoemulsions of the disclosed are non-toxic and safe when swallowed, inhaled, or contacted to the skin of a subject.

The rPA vaccine compositions of the disclosed can be produced in large quantities and are stable for many months at a broad range of temperatures. The nanoemulsion adjuvants can have textures ranging from that of a semi-solid cream to that of a thin lotion, to that of a liquid and can be applied topically by any pharmaceutically acceptable method as stated above, e.g., by hand, or nasal drops/spray.

At least a portion of the emulsion may be in the form of lipid structures including, but not limited to, unilamellar, multilamellar, and paucliamellar lipid vesicles, micelles, and lamellar phases.

The present disclosure contemplates that many variations of the described rPA vaccines will be useful in the methods of the present disclosure. To determine if a candidate vaccine is suitable for use with the present disclosure, three criteria are analyzed. Using the methods and standards described herein, candidate vaccines can be easily tested to determine if they are suitable. First, the desired ingredients are prepared using the methods described herein, to determine if a vaccine can be formed. If a vaccine cannot be formed, the candidate is rejected. Second, the candidate vaccine should be stable; e.g., if the vaccine is a nanoemulsion vaccine, then the nanoemulsion should be stable. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate vaccines should have efficacy for its intended use. For example, the vaccines of the disclosed should induce a protective immune response to a detectable level.

The rPA vaccines of the disclosed can be provided in many different types of containers and delivery systems. For example, in some embodiments of the disclosed, the vaccines are provided in a cream or other solid or semi-solid form. The vaccines of the disclosed may be incorporated into hydrogel formulations.

The rPA vaccines can be delivered (e.g., to a subject or customers) in any suitable container. Suitable containers can be used that provide one or more single use or multi-use dosages of the vaccines for the desired application. In some embodiments of the disclosed, the vaccines are provided in a suspension or liquid form. Such rPA vaccines can be delivered in any suitable container including spray bottles and any suitable pressurized spray device. Such spray bottles may be suitable for delivering the vaccines intranasally or via inhalation. These containers can further be packaged with instructions for use to form kits.

VI. Definitions

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "adjuvant" refers to an agent that increases the immune response to an antigen (e.g., a pathogen).

As used herein, the term "immune response" refers to a subject's (e.g., a human or another animal) response by the immune system to immunogens (i.e., antigens) which the subject's immune system recognizes as foreign. Immune responses include both cell-mediated immune responses (responses mediated by antigen-specific T cells and non-specific cells of the immune system) and humoral immune responses (responses mediated by antibodies present in the plasma lymph, and tissue fluids). The term "immune response" encompasses both the initial responses to an immunogen (e.g., a pathogen) as well as memory responses that are a result of "acquired immunity."

As used herein, a "subject" includes any animal for which diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

The terms "chelator" or "chelating agent" refer to any materials having more than one atom with a lone pair of electrons that are available to bond to a metal ion.

As used herein, the term "enhanced immunity" refers to an increase in the level of acquired immunity to a given pathogen following administration of a vaccine of the present disclosure relative to the level of acquired immunity when a vaccine of the present disclosure has not been administered.

As used herein, the term "immunogen" refers to an antigen that is capable of eliciting an immune response in a subject. In preferred embodiments, immunogens elicit immunity against the immunogen (e.g., a pathogen or a pathogen product) when administered in combination with a nanoemulsion of the present disclosure.

As used herein, the term "intranasal(ly)" refers to application of the compositions of the present disclosure to the surface of the skin and mucosal cells and tissues of the nasal passages, e.g., nasal mucosa, sinus cavity, nasal turbinates, or other tissues and cells which line the nasal passages.

The term "nanoemulsion," as used herein, includes small oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. The present disclosure contemplates that one skilled in the art will appreciate this distinction when necessary for understanding the specific embodiments herein disclosed.

The terms "pharmaceutically acceptable" or "pharmacologically acceptable," as used herein, refer to compositions that do not substantially produce adverse allergic or adverse immunological reactions when administered to a host (e.g., an animal or a human). Such formulations include any pharmaceutically acceptable dosage form. Examples of such pharmaceutically acceptable dosage forms include, but are not limited to, dips, sprays, seed dressings, stem injections, lyophilized dosage forms, sprays, and mists. As used herein, "pharmaceutically acceptable carrier" includes any and all solvents, dispersion media, coatings, wetting agents (e.g., sodium lauryl sulfate), isotonic and absorption delaying agents, disintegrants (e.g., potato starch or sodium starch glycolate), and the like.

As used herein, the term "topical(ly)" refers to application of the compositions of the present disclosure to the surface of the skin and mucosal cells and tissues (e.g., buccal, lingual, sublingual, masticatory, respiratory or nasal mucosa, nasal turbinates and other tissues and cells which line hollow organs or body cavities).

As used herein, "viral particles" refers to mature virions, partial virions, empty capsids, defective interfering particles, and viral envelopes.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, the disease being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

The disclosed is further described by reference to the following examples, which are provided for illustration only. The disclosed is not limited to the examples, but rather includes all variations that are evident from the teachings provided herein. All publicly available documents referenced herein, including but not limited to U.S. patents, are specifically incorporated by reference.

EXAMPLES

Example 1—Stabilization of rPA

The purpose of this example was to optimize various compositions to stabilize the secondary and tertiary structures of globular proteins by proactively screening and addressing all of the destabilizing and un-stabilizing factors that would affect the structure and lead to aggregation and degradation of the rPA protein.

Selection of Stabilizing Excipients for Vaccine Formulation: A screening study was performed on various formulations shown in the table below. These are screening stability studies that were used to guide formulation development and narrow in on the excipient to be used in the final formulation selection. Various prototype formulations were placed on informal stability studies Table 3 describes the various buffer systems and additional stabilizing excipient that were investigated. Various prototype formulations were placed on informal stability studies and are described in the tables below. In particular, the different buffer systems, either phosphate or TRIS buffer, were evaluated as the base and additional excipients were then added in a matrix type design.

TABLE 3

Stabilizing excipients and function

| Excipients/Systems | Example of Excipients | Function |
| --- | --- | --- |
| Buffer Systems | 10 mM PBS buffer (pH 7.4,) 10, 80 mM TRIS buffer (pH 8.0) | Control the pH of the system; Optimized solubility based on the Isoelectric Point (pI) of the Protein; Buffering components to control pH (effects the pI) |
| Salts | 100-150 mM Sodium Chloride | Increase the surface tension of water ionic strength. Optimize Ionic strength; if there is calcium dependent folding of the protein domain |
| Sugars | 5, 15% Trehalose 5% Sucrose | Protect protein native conformation, alters tonicity and osmolality |
| Amino Acids | 20, 60 mM Histidine | Direct protein binding, buffering capacity, and antioxidant properties, suppressing the aggregation of folding intermediates, radical attacks by reactive oxygen and nitrogen species, prevents denaturation of amino acids. |
| Storage: Inert Gas, Limit Head Space, Protect from Light, Low Agitation | Nitrogen, Argon Glass covered by Foil (Amber glass may have leachables) Fill Volume No vortexing, Simple mixing with low shear. | Hydrogen bonds are broken by increased translational energy, shearing of hydrogen bonds, Inclusion of inert gas to prevent oxidation Protection from light |

Figure 5:
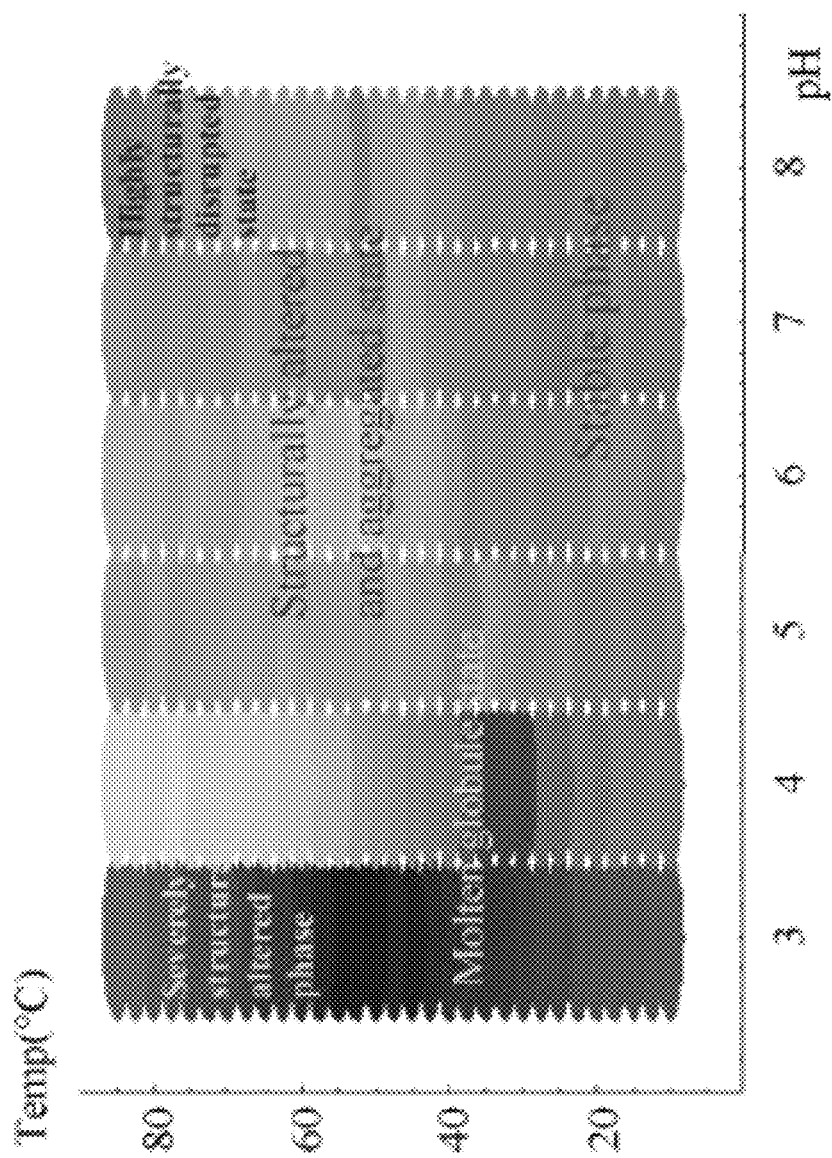
FIG. 5 shows the best pH for protection against aggregation of an exemplary protein, anthrax protective antigen (rPA).
Figure 6:
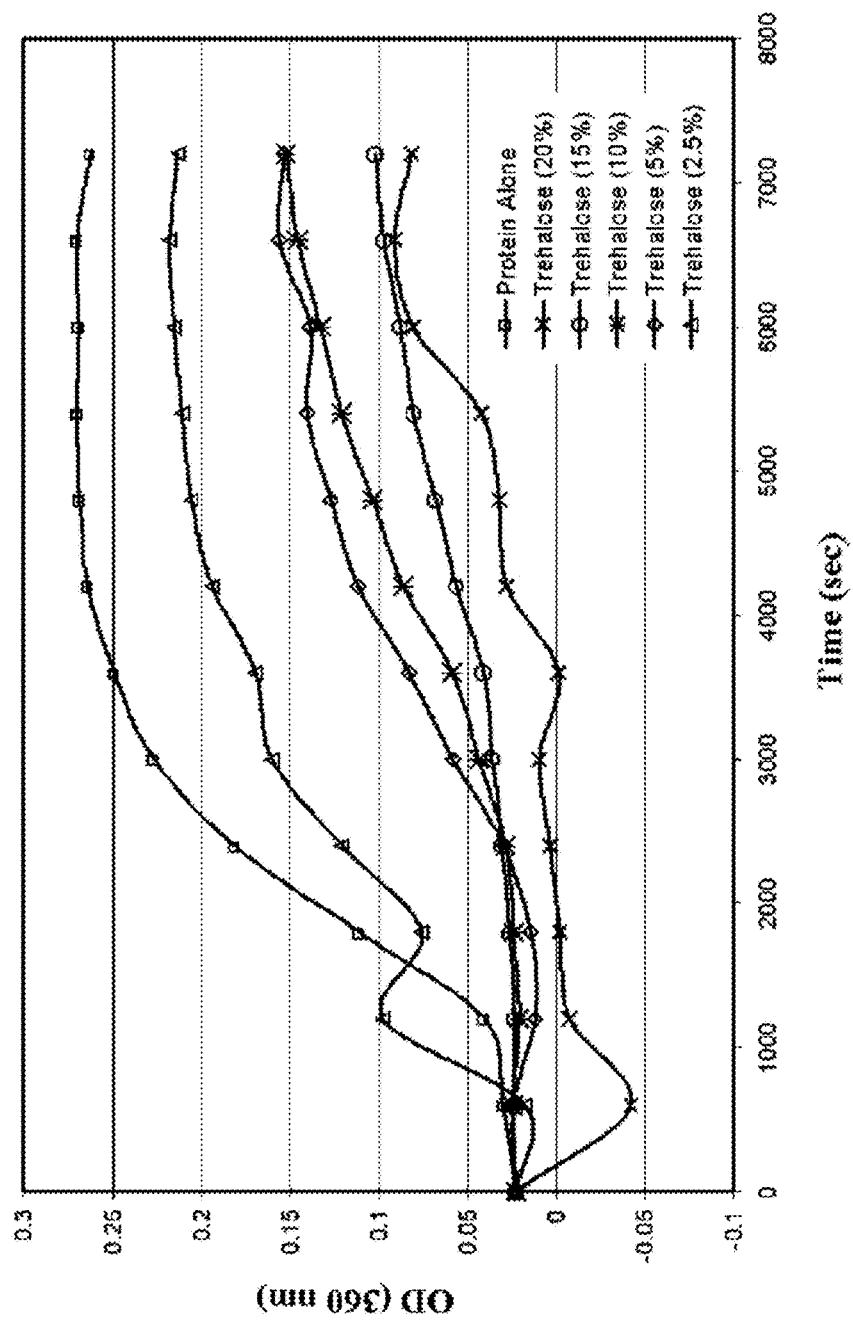
FIG. 6 shows the best concentration of trehelose against an exemplary protein, rPA, aggregation by trehalose (showing six different concentrations of trehalose).

The selection of a stabilizing sugar helps protect the protein antigen rPA at higher temperatures. FIG. 5 shows the best pH and FIG. 6 shows the optimal concentration of trehalose to protect the protein antigen rPA from aggregation. Jiang et al., "Anthrax Vaccine Powder Formulations for Nasal Mucosal Delivery," *Journal of Pharmaceutical Sciences*, 95: 80-96 (2006).

The effect of pH and temperature was evaluated via a phase diagram, and the most stable phase was found to be in the lower right-hand corner of FIG. 5, where the pH was from 7-8. Below this pH, molten globule-like state structures are apparent around pH 3. Thus, pH 7.4-8 was the targeted pH for the prototype protein antigen formulations.

Figure 7:
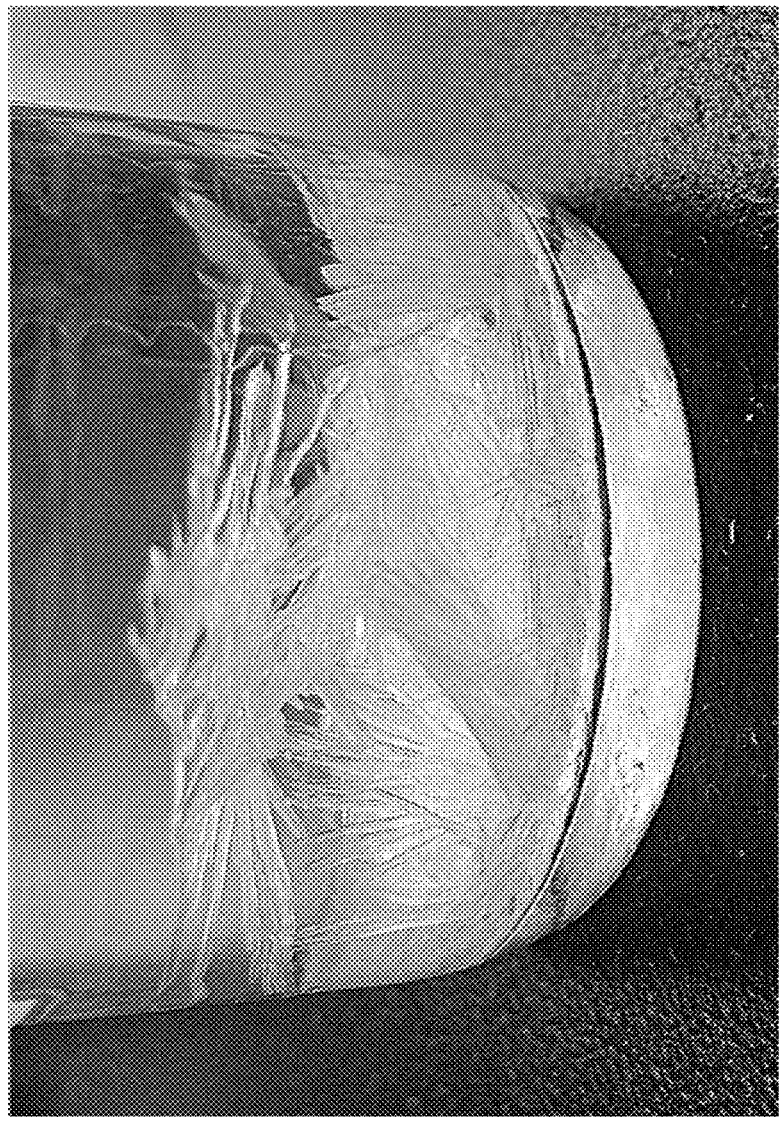
FIG. 7 shows crystallization of mannitol in buffer store at 2-8° C. for four weeks.

A potential stabilizer, trehalose, is also identified in Jiang et al., as several concentrations of protein antigen formulations comprising trehelose were evaluated while heating an rPA solution. The disaccharide trehalose was found to be one of the most effective aggregation inhibitors. The extent of inhibition of rPA aggregation was concentration-dependent, as shown in FIG. 6. In this case, about 5% or higher concentrations of trehalose elicited 50% inhibition of protein aggregation, consisting of a mixture of secondary structure moieties (e.g., a-helix and b-sheet). Thus, 5% and 15% trehalose were the two concentrations further investigated regarding promotion of rPA protein antigen stability. Sucrose and mannitol were selected for further study. However, following this selection it was discovered that mannitol crystalized out of solution on prolonged storage at 2-8° C., as shown in FIG. 7. Hence, mannitol was removed from further formulation consideration.

Example 2—Prototype Formulation Comprising rPA

The purpose of this example was to identify a prototype formulation design for stability of anthrax protective antigen (rPA). Exemplary stabilizing systems are shown in Tables 7-9.

The rPA concentrations used in the studies bracketed at concentrations of 100 µs/mL and 500 µg/mL rPA. The base formulation in a phosphate buffer system was placed on stability at 5° C., 25° C. and 40° C. for 1 and 3 months. The rPA prototype formulations were stored at −20° C., 5° C. and 25° C. for longer stability time points (e.g. 1, 3, 6 and up to 12 months). The rPA prototype formulations were also stored at 40° C. and were analyzed at 1, 3 and 6 months.

The rPA stability assays included physical appearance, pH, particle size, cetylpyridinium chloride potency (CPC potency, % CPC), qualitative Western Blot for rPA (MW=83 kDa), rPA potency (% rPA) was determined by RP-HPLC and SEC-HPLC. CPC is a compound present in the nanoemulsions, and the measurement of CPC can be used as a "marker" to determine if the potency of the nanoemulsion adjuvant decreases over time.

FIGS. 2-4 show schematic diagrams of the decision trees used in the selection of the stabilizing excipients in the methods of the invention. The three series of prototype formulations and the excipient variable that were optimized are highlighted in the figures.

Example 3—Effect of Excipients on the Thermostability of rPA

As another example of the universal applicability of the disclosed methods and compositions for stabilizing a protein or peptide of interest, various systems were tested to confirm that the disclosed rPA compositions and methods could also stabilize and preserve rPA. Table 4 describes the various buffer systems and additional stabilizing excipients that were investigated. These are heat screening stability studies that were used to guide rPA formulation development. Various rPA prototype formulations were placed on informal stability and are described.

Various test formulations with differing amounts/types of excipients, as shown in Table 6, were assessed for stability.

molecule at a given pH. Amino acids that make up proteins may be positive, negative, neutral, or polar in nature, and together give a protein its overall charge. At a pH below their pI, proteins carry a net positive charge; above their pI they carry a net negative charge. The larger the difference between the pI and the pH, the greater net charge is on the protein. The pI of rPA is 5.6. Hence, two pH units above the

TABLE 4

Stabilizing Excipients and Function.

Example 4—Heat Screening Study of rPA

This heat screening study focused on testing rPA formulations comprising two buffers (PBS or TRIS) and excipients, such as sodium chloride (NaCl), sucrose, histidine, and glycerol. The rPA aqueous solutions tested are listed in Table 6. The concentration of rPA was 500 μg/mL.

The following is the procedure and acceptance criteria for the rPA aqueous solution plus excipients screening experiments:

1) Prepare desired rPA buffer formulations (control and test formulations)
2) Heat test formulation in heating block set at 49° C. for 5 minutes.
3) Assess percent area of rPA peak following incubation versus control.
4) Select the buffer formulations that have >70% area and no secondary peak at 15 minutes as assessed by SEC.

Example 5—Development of rPA SEC and RP-HPLC Method

Figure 9:
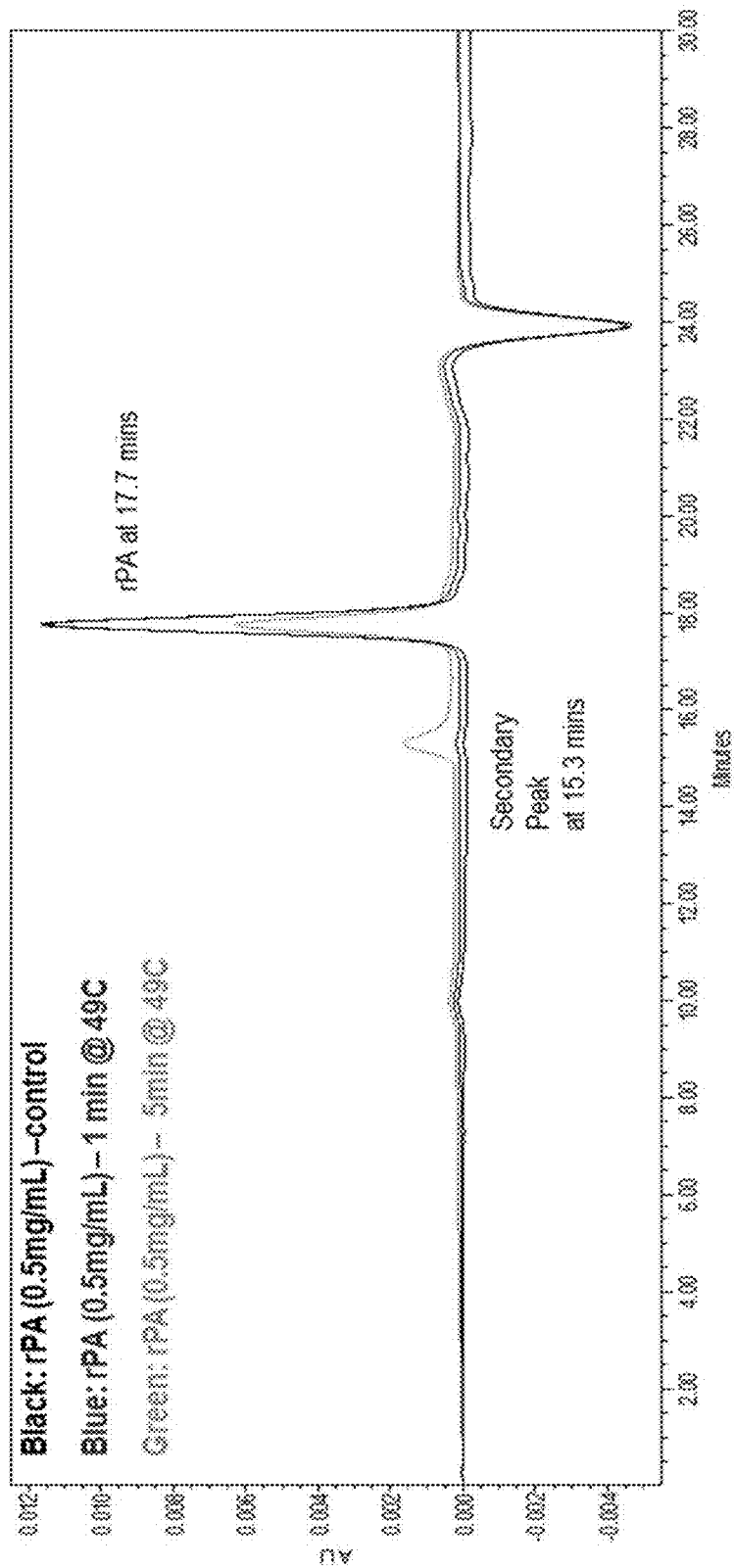
FIG. 9 shows SEC-HPLC chromatograph of rPA solution after incubation at 49° C. for 1 and 5 minutes
Figure 10:
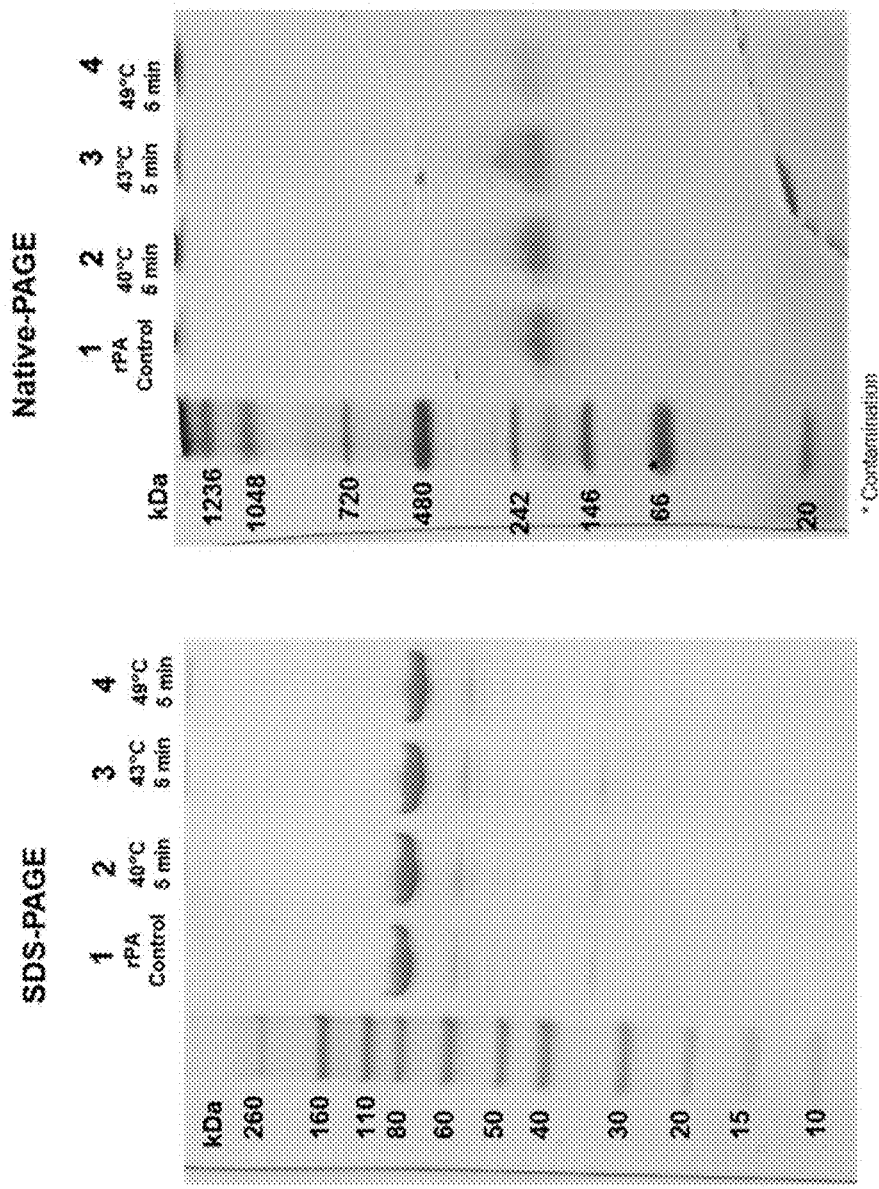
FIG. 10 shows the effect of temperature and time on rPA physical stability using PAGE gels.
Figure 11:
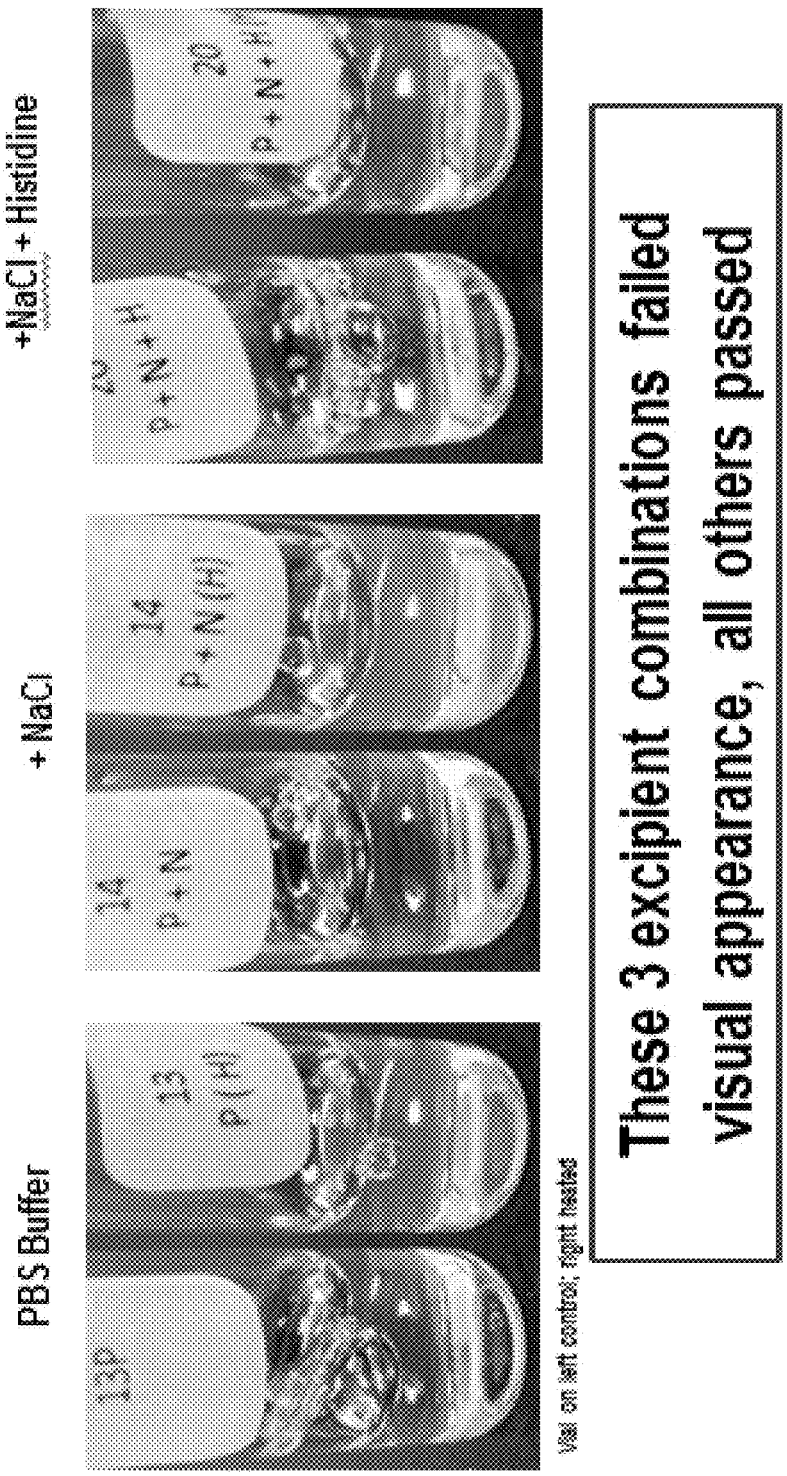
FIG. 11 shows the physical appearance of 500 µg/ml rPA in sodium phosphate systems with different excipients: Non-heated Control (left vial), Heating at 49° C. for 5 minutes (right vial).
Figure 12:
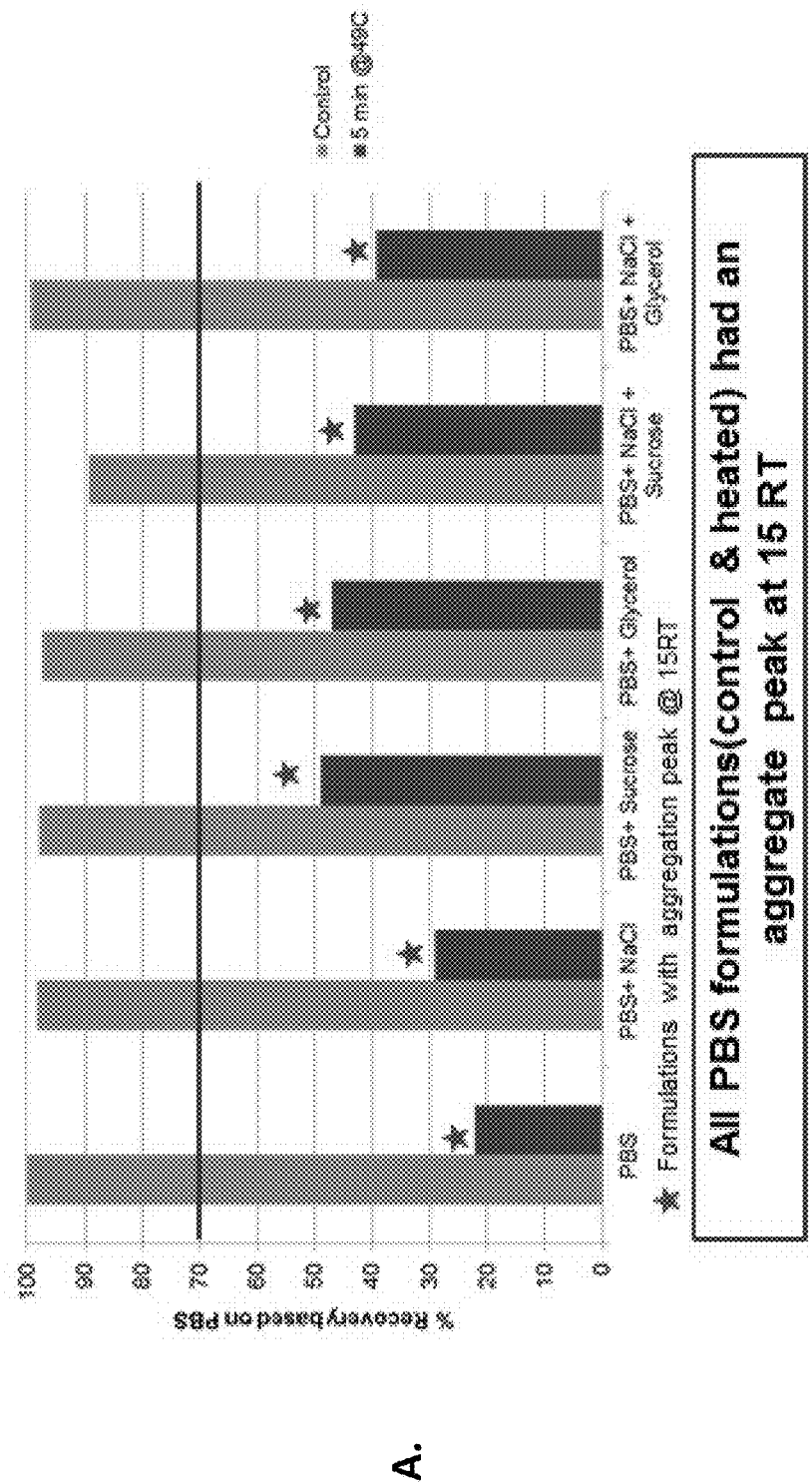
FIG. 12 shows comparisons of rPA peak area as determined by SEC-HPLC of rPA in phosphate buffered solutions (PBS) with additional stabilizing excipients. Panel (A) shows formulations without histidine and panel (B) shows formulations with histidine.
Figure 13:
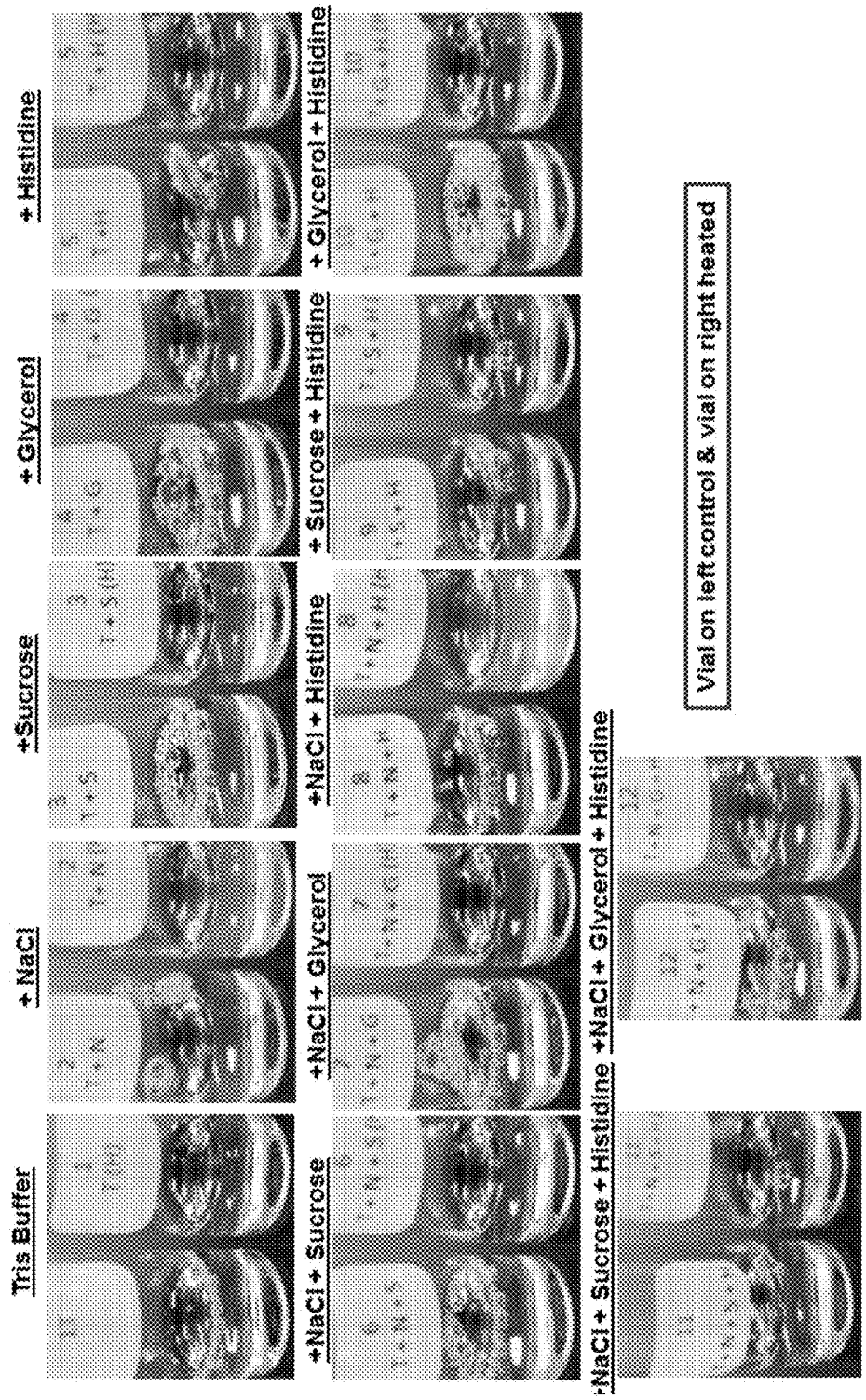
FIG. 13 shows the physical appearance of 500 µg/ml rPA in TRIS buffer with different excipients following heating at 49° C. for 5 Minutes
Figure 14:
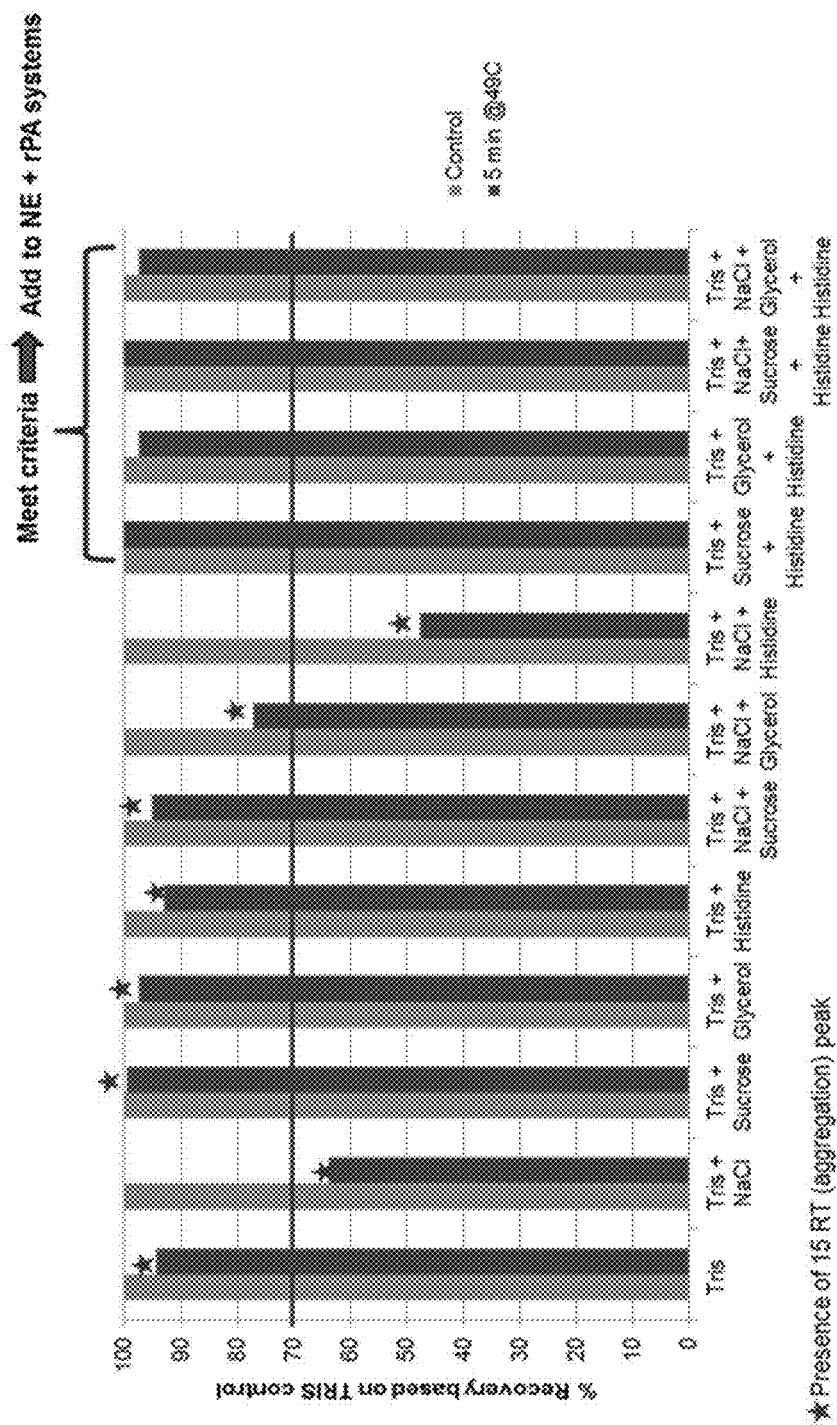
FIG. 14 shows comparison of rPA Peak area as determined by SEC-HPLC of various with TRIS Buffer Formulations. Some peaks include rPA+20% W805EC nanoemulsion.
Figure 15:
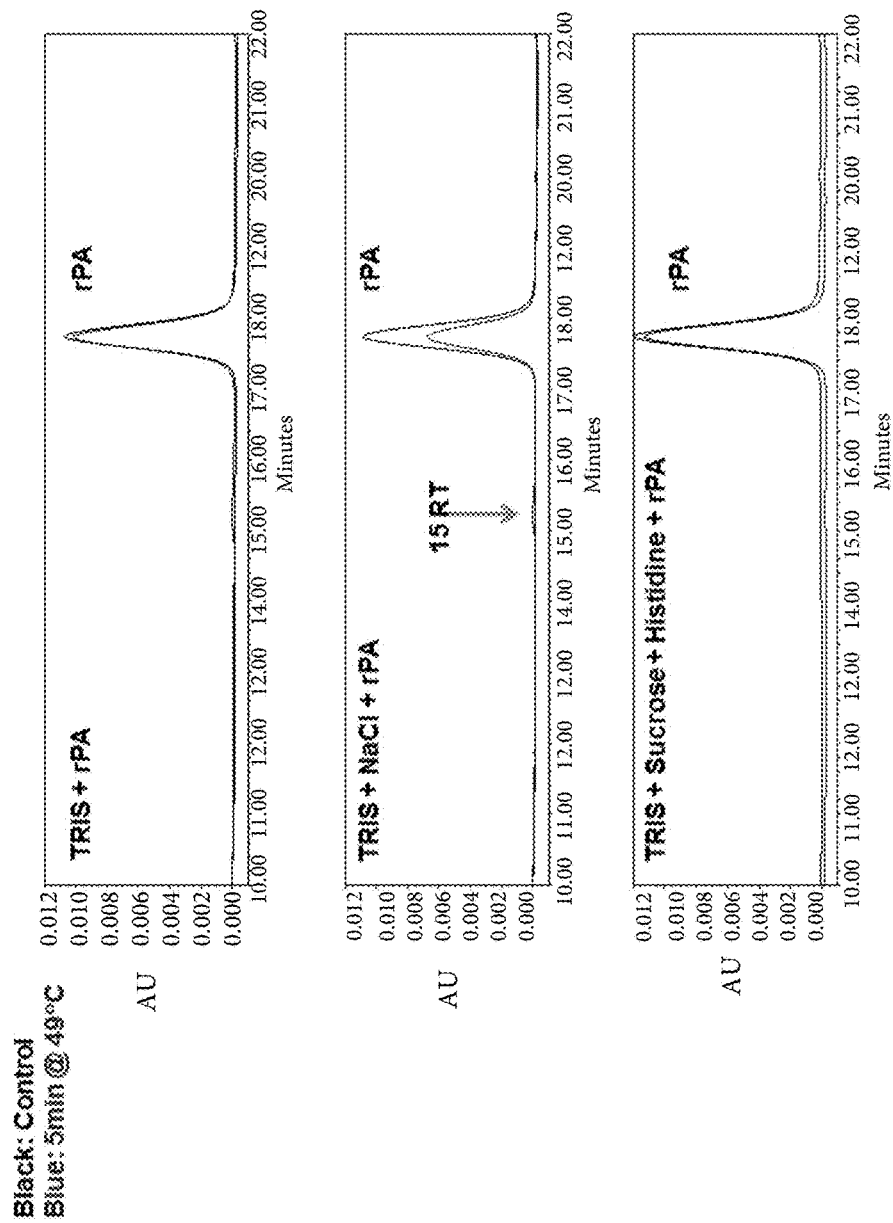
FIG. 15 shows SEC-HPLC chromatographs of rPA in various excipients.

Incubation of the rPA solution at 49° C. for 5 minutes using a heating block caused thermal aggregation of rPA (Table 5 and FIG. 9); whereas at the other conditions the rPA was stable. Thermal aggregation at this condition was also confirmed with native PAGE (FIG. 10). Thus, 49° C. for 5 minutes was the condition selected to rapidly screen various rPA formulations shown in Table 6.

The screening method for the stabilizing excipients consisted of using size exclusion chromatography (SEC-HPLC) to compare the area of the rPA peak in different rPA formulations heated to 49° C. for 5 minutes compared to a non-heated sample. Formulations that had a greater than 80% peak area and no secondary peak at 15 minutes on SEC-HPLC were selected was considered stable.

TABLE 5

Effect of Temperature and Time on rPA Physical Stability using SEC-HPLC.

| Screening (Heating) Condition | % rPA Area SEC-HPLC |
|---|---|
| Control (No heating) | 100.0 |
| 1 min at 40° C. | 108.4 |
| 5 min at 40° C. | 104.2 |
| 1 min at 43° C. | 104.2 |
| 5 min at 43° C. | 104.0 |
| 1 min at 49° C. | 103.8 |
| 5 min at 49° C. | 37.9 |

FIG. 11 shows that when the sodium phosphate system was heated, the rPA solutions turned turbid. When the solution turns turbid, this indicates aggregation and precipitation of the rPA protein. These three compositions in FIG. 11 clearly failed visual appearance. FIG. 12 shows that all of the rPA formulations tested with sodium phosphate and additional excipients when heated lost rPA recovery. All of the rPA formulations, except two, were well below the 70% cut off point. The two rPA formulations above 70%, however, showed a 15 minute retention time rPA aggregation peak, as indicated by a star.

TABLE 6

List of Excipient used in rPA Aqueous Screening Studies.

| Excipients | 10 mM Sodium Phosphate (pH 7.4) | 10 mM TRIS (pH 8) |
|---|---|---|
| Control | X | X |
| 50 mM NaCl | X | X |
| 5% Sucrose | X | X |
| 20 mM Histidine | X | X |
| 5% Glycerol | X | X |
| 50 mM NaCl + 5% Sucrose | X | X |
| 50 mM NaCl + 5% Glycerol | X | X |
| 50 mM NaCl + 20 mM Histidine | X | X |
| 5% sucrose + 20 mM Histidine | X | X |
| 5% Glycerol + 20 mM Histidine | X | X |
| 20 mM Histidine + 50 mM NaCl + 5% Sucrose | X | X |
| 20 mM Histidine + 50 mM NaCl + 5% Glycerol | X | X |

FIG. 13 shows the physical appearance of the TRIS systems with various excipients before and after heating. A couple of turbid solutions (+NaCl, +NaCl+Histidine) developed after heating, which indicates aggregation and precipitation of the rPA protein. FIG. 14 show that four compositions met the acceptance criteria.

In summary, the screening method indicated that the TRIS buffer system, rather than phosphate buffer system was the better buffer with respect to rPA stability (FIGS. 13 and 14). None of the rPA PBS solutions listed in above met the acceptance criteria. The recovery of rPA for all the samples following heating was less than 70%. Only two of these solutions, the histidine, and sucrose with or without NaCl had recovery of rPA greater than 70%. All other formulations had percent rPA recovery less than 60%. Additionally, for all of these formulations the unheated control and the formulations heated for 5 minutes at 49° C. exhibited an aggregate peak at a retention time of 15 minutes as determined by SEC-HPLC. FIG. 15 shows some example chromatographs. Four of the heat-treated TRIS buffer formulations met the acceptance criteria as indicated in FIG. 15.

Example 6—Effect of Excipients on the Long-Term Stability of rPA (Prototype Stabilizing Systems)

The rPA concentrations used bracketed at 100 μg rPA/ml and 500 μg rPA/mL. The prototype formulations were stored at −20° C., +5° C. and +25° C., and stability of the different formulations was determined after 1, 3, 6, 9, and 12 months. Formulations were also stored at 40° C. and analyzed at 1, 3, and 6 months. The stability assays are listed in Appendix 1, 2 and 3 and include: physical appearance, pH, particle size, qualitative Western Blots for rPA, rPA determined by RP-HPLC and SEC-HPLC. The Western blots method for rPA and were probed using the Novus rabbit polyclonal whole sera antibody as the primary antibody.

FIGS. 2-4 show schematics of the decision trees used in the selection of the stabilizing excipients. Between each prototype there was an additional screening step to optimize at least one of the excipients (i.e. the buffer in prototype 1/FIG. 2; Trehalose is prototype 2/FIG. 3; and Glutathione in Prototype 3/FIG. 4).

Tables 7-9 list the formulations for Prototypes 1, 2 and 3 placed on informal stability at −20° C., 5° C., 25° C., and 40° C. at various time points.

TABLE 7

Composition of Prototype 1 Formulations.

Prototype 1 Excipient Compositions

| Lot # | Type | rPA (µg/mL) | % NE | Buffer System | NaCl (mM) | Histidine (mM) | Sucrose (mM) |
|---|---|---|---|---|---|---|---|
| X-1596 | rPA aqueous | 100 | 0 | 10 mM PBS | 100 | 20 | 5 |
| X-1595 | rPA aqueous | 500 | 0 | 10 mM PBS | 100 | 20 | 5 |
| X-1601 | rPA aqueous | 100 | 0 | 10 mM TRIS | 150 | 20 | 5 |
| X-1600 | rPA aqueous | 500 | 0 | 10 mM TRIS | 150 | 20 | 5 |

TABLE 8

Composition of Prototype 2 Formulations.

Prototype 2 Excipient Compositions

| Lot # | Type | rPA (µg/mL) | % NE | Buffer System | NaCl (mM) | Histidine (mM) | Trehalose (%) | Glutathione (mM) | EDTA (mM) |
|---|---|---|---|---|---|---|---|---|---|
| X-1624 | rPA aqueous | 100 | 0 | 80 mM TRIS | 150 | 20 | 5 | 16 | 0.5 |
| X-1626 | rPA aqueous | 500 | 0 | 80 mM TRIS | 150 | 20 | 5 | 16 | 0.5 |
| X-1629 | rPA aqueous | 100 | 0 | 80 mM TRIS | 150 | 20 | 15 | 16 | 0.5 |
| X-1631 | rPA aqueous | 500 | 0 | 80 mM TRIS | 150 | 20 | 15 | 16 | 0.5 |

TABLE 9

Composition of Prototype 3 Formulations.

Prototype 2 Excipient Compositions

| Lot # | Type | rPA (µg/mL) | % NE | Buffer System | NaCl (mM) | Histidine (mM) | Trehalose (%) | Glutathione (mM) |
|---|---|---|---|---|---|---|---|---|
| X-1634 | rPA aqueous | 100 | 0 | 80 mM TRIS | 150 | 60 | 15 | 0 |
| X-1636 | rPA aqueous | 500 | 0 | 80 mM TRIS | 150 | 60 | 15 | 0 |
| X-1639 | rPA aqueous | 100 | 0 | 80 mM TRIS | 150 | 60 | 15 | 16 |
|

TABLE 10-continued

Test Method and Acceptance Criteria
for the Formulations Placed on Informal Stability

| Stability Parameter | Test Method | Acceptance Criteria for Each Formulation Type rPA Buffered Solution (rPA Aqueous) |
|---|---|---|
| rPA % Label Claim* | SEC-HPLC RP-HPLC | ≥80% |

*The % rPA label claim is used to describe the % rPA recovered.

Example 7—Physical Appearance Test Method

Figure 16:
FIG. 16 shows examples of physical acceptance criteria of rPA buffered aqueous solutions.
Figure 17:
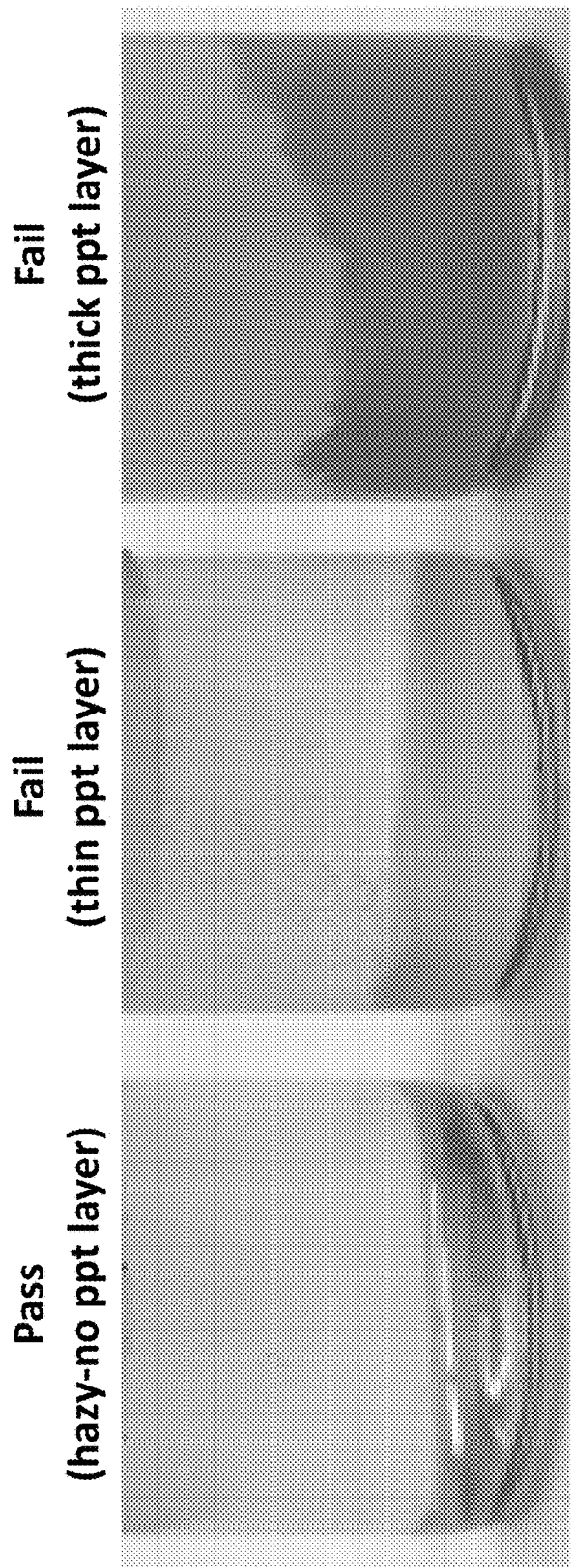
FIG. 17 shows examples of physical acceptance criteria of rPA buffered aqueous solutions.
Figure 18:
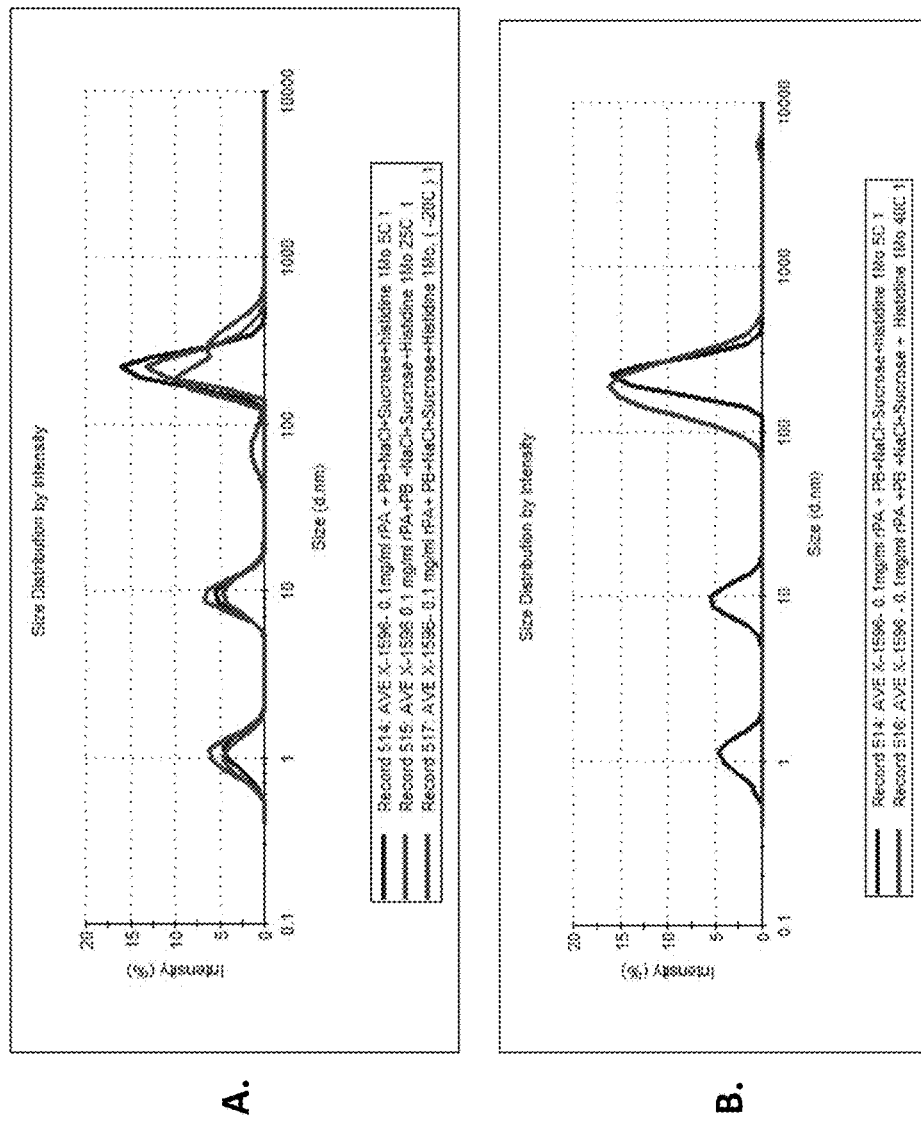
FIG. 18 shows the particle size profile of 100 µg/mL rPA aqueous solution (Prototype 1: X-1596). Panel (A) shows stability data at 1 month at −20° C., 5° C., and 25° C., and panel (B) shows stability data at 1 month at 5° C. and 40° C.

Physical appearance of the formulations was determined at the initial time point and at different time points under various storage conditions. The physical appearance observation was then recorded and evaluated using the acceptance criteria in Table 11. FIGS. 16 and 17 illustrate examples of the acceptance criteria.

TABLE 11

Stability Parameters, Description, and Acceptance Criteria

| Stability Parameter | Description | Acceptance Criteria | |
|---|---|---|---|
| | | Pass: | Fail: |
| Precipitate (ppt) | Precipitation (ppt) of rPA. Remixing will not restore homogeneity. | None Hazy appearance, no ppt layer Mil | Thin/Moderate precipitation layer Thick/Extreme precipitation layer |

Example 8—pH Assessment

The pH was measured using a standard pH meter with the appropriate probe that can be used for both TRIS and PBS buffer systems. The formulations shown in Tables 7-9 are the formulations for which pH was assessed over time while storing the formulations at various temperatures. These results are shown in FIGS. 37-39.

Example 9—Particle Size Analysis and Polydispersity Index (PdI)

The mean particle size (Z-average) and polydispersity index (PdI) were determined for all the tested samples. The particle size and PdI of the sample was measured by dynamic light scattering using photon correlation spectroscopy with a Malvern Zetasizer Nano ZS90 (Malvern Instruments, Worcestershire, UK). All measurements were carried out at 25° C. with no dilution.

FIG. 18 shows the particle size profile of a 100 μg/mL rPA aqueous solution (Prototype 1: X-1596). It is apparent from the profile that the rPA particle size peak appears around 10 nm. The other two peaks are from the external phase buffer. FIG. 18A shows the solution at various one month stability temperatures of −20° C., 5° C., and 25° C. The rPA peak is retained. However, in FIG. 18B the rPA peak disappears at the 40° C., indicative of instability of the rPA at this temperature and time point.

Example 10—Label Claim of rPA by RP-HPLC or SEC-HPLC Test Method

The percent label claim (recovery) of rPA was determined using RP-HPLC and SEC-HPLC. Tables 10 and 11 describe the parameters of the each method.

TABLE 12

| Size Exclusion HPLC Parameters for rPA determination. | |
|---|---|
| Parameter | Setting |
| Separation Mode | SEC |
| Stationary Phase | Tosoh Bioscience TSK-GEL G3000SWxL, 7.8 mm, 10 × 300 mm, L |
| Column Temperature | 25° C. |
| Run Time | 30-45 minutes (range for development purposes) |
| Flow Rate | 0.5 mL/min |
| Gradient/Isocratic | Isocratic |
| Mobile Phase | 0.1M Sodium Phosphate, 0.1M Sodium Sulfate, pH 6.8 |
| Sample Temperature | 4° C. |
| Injection Volume | 10 μL for formulations containing 500 μg/mL rPA<br>50 μL for formulations containing 100 μg/mL rPA |
| Detector Wavelength | 220 nm |
| Retention Time | 19.7 minutes with a guard column<br>17.7 minutes without a guard column |

TABLE 13

| RP-HPLC HPLC Chromatographic Conditions for rPA determination. | |
|---|---|
| Column: | ACE 5 Phenyl-300, 100 × 4.0 mm id, ACE Part Number: ACE-225-1004 |
| Elution Type | Gradient |
| Flow Rate | 0.5 mL/minute |
| Column Temperature: | 45° C. |
| Buffer A | 0.05% Trifluoroacetic Acid (TFA) in Water |
| Buffer B | 0.04% Trifluoroacetic Acid (TFA) in Acetonitrile |
| Auto Sampler Temperature: | 4° C. |
| Injector Volume: | 10 μL or |
| rPA Strengths: | For 10 μL: 2.5 ppm, 5 ppm, 10 ppm, 20 ppm, 25 ppm, 50 ppm, 100 ppm, 150 ppm, 200 ppm<br>For 50 μL: 2.5 ppm, 5 ppm, 10 ppm, 20 ppm, 25 ppm, 50 ppm, 100 ppm |
| Detector Wavelength: | 214 nm |
| Run Time: | 37.5 minutes |
| Retention Time: | 12.5 minutes |

Informal stability studies of rPA formulations without stabilizing excipients were initiated. The compositions of the formulations are presented in Table 14.

TABLE 14

| rPA Formulation in 10 mM Phosphate Buffer Solution with 100 mM NaCl. | | | | | |
|---|---|---|---|---|---|
| | | Pre-Prototype Compositions | | | |
| Lot # | Type | rPA (μg/mL) | % NE | Buffer System | NaCl (mM) |
| X-1668 | rPA aqueous | 100 | 0 | 10 mM PBS | 100 |
| X-1670 | rPA aqueous | 500 | 0 | 10 mM PBS | 100 |

The rPA concentrations tested for stability, bracket at 100 μg rPA/mL and 500 μg rPA/mL. The formulations were stored at −20° C., 5° C., and 25° C., and the stability of the formulation was assessed at 1, 3, and 6 months. Formulations were also placed at 40° C. and analyzed at 1, 3, and 6 months. The stability assays included: physical appearance, pH, particle size, and qualitative Western Blots for rPA, and % rPA label claim. % rPA label claim was determined by RP-HPLC and SEC-HPLC. The Western Blots for this set of formulations are not shown.

The purpose of this experiment was to test rPA in a 10 mM phosphate buffered system with 100 mM NaCl without any stabilizing excipients.

Table 15 shows the stability data of a low dose (100 µg/mL) rPA, aqueous formulation (X-1668) in a phosphate buffer without any stabilizing excipients. It was stable for 3 months at 5° C. and 25° C. However, the high dose (500 µg/mL rPA) rPA aqueous formulation (X-1670) shown in Table 14 showed to be less stable. X-1670 was stable at 3 months at 5° C., but failed at 25° C.

This data indicates that stabilizing excipients are needed to help improve the stability of rPA at higher temperature for a longer duration.

The purpose of this set was to select the best buffer for between PBS and TRIS. It was evident that the TRIS System was superior to PBS in stabilization of rPA in formulations. At low dose 100 µg/mL rPA, the PBS system showed rPA stability at 3 months at 5° C. However, at high dose 500 µg/mL rPA, the PBS system only had 6 months at 5° C., while the TRIS system provided stability of rPA for 12 months at 5° C. for the high dose.

TABLE 15

Overall Summary of 100 µg/mL in 10 mM Phosphate Buffer with 100 mM NaCl.

| Time Point | Storage Condition | Physical Appearance | pH (±0.5) | Particle Size (nm) | PdI | Western Blot (~83 kD Band) | rPA - HPLC RP (SEC) (>80%) |
|---|---|---|---|---|---|---|---|
| 0 | Initial | Pass | 7.49 | 8.26 | — | Band | 98 (98) |
| 1 month | 5° C. | Pass | 7.40 | 8.6 | — | Band | 87 (90) |
|  | 25° C./60% RH | Pass | 7.42 | 8.0 | — | Band | 95 (0) |
|  | 40° C./75% RH | Pass | 7.52 | 10 | — | Lt Band | 29 (0) |
| 3 month | 5° C. | Pass | 7.42 | 8.7 | — | Band | 100 (100) |
|  | 25° C./60% RH | Pass | 7.52 | 7.5 | — | Band | 96 (93) |
|  | 40° C./75% RH | Pass | 7.82 | 0 | — | No Band | 4 (0) |
| 6 months | 5° C. | Pass | 7.38 | 9.78 | — | Band | 86 (89) |
|  | 25° C./60% RH | Pass | 7.37 | 7.94 | — | No Band | 74 (71) |
|  | 40° C./75% RH | Pass | 7.55 | ND | — | ND | 4/0 |

TABLE 16

Overall Summary of 500 µg/mL rPA in 10 mM Phosphate Buffer with 100 mM NaCl

| Time Point | Storage Condition | Physical Appearance | Particle Size (nm) | PdI | Western Blot (~83 kD Band) | rPA - HPLC RP (SEC) (>80%) |
|---|---|---|---|---|---|---|
| 0 | Initial | Pass | 8.45 | — | Band | 95 (98) |
| 1 month | 5° C. | Pass | 8.3 | — | Band | 97 (100) |
|  | 25° C./60% RH | Pass | 7.4 | — | Band | 95 (97) |
|  | 40° C./75% RH | Fail | 0 | — | Lt Band | 5 (3) |
| 3 month | 5° C. | Pass | 8.2 | — | Band | 101 (105) |
|  | 25° C./60% RH | Pass | 0 | — | No Band | 0 (0) |
|  | 40° C./75% RH | Fail | 0 | — | No Band | 0 (0) |
| 6 months | 5° C. | Pass | 8.2 | — | No Band | 93 (92) |
|  | 25° C./60% RH | Pass | 0 | — | No Band | 0/0 |
|  | 40° C./75% RH | Fail | 0 | — | No Band | 0/0 |

Informal stability studies of various rPA aqueous formulations were initiated on the formulations shown in Table 7. The previous screening stability studies helped to guide formulation development and final formulation selection. The first prototype series was two sets of formulations containing either phosphate or TRIS buffer. The test methods and acceptance criteria for the formulations placed on informal stability are shown above. The rPA concentrations shown for stability, bracket at 100 µg rPA/mL and 500 µg rPA/mL. The formulations were stored at −20° C., 5° C. and 25° C. and stability was assessed at 1, 3, 6, 9, and 12 months. Formulations were also placed at 40° C. and were analyzed at 1, 3, and 6 months. The stability assays include: physical appearance, pH, particle size, and qualitative Western Blots. At later time points, rPA recovery was determined by RP-HPLC and SEC-HPLC.

Example 11—Stability Data for Prototype 2 Formulations (TRIS with 5% or 15% Trehalose)

The second prototype was two sets of formulation containing either 5% or 15% trehalose in a TRIS buffered system as shown in Table 8. The test methods and acceptance criteria for the formulations placed on informal stability are shown in Table 7. The rPA concentrations shown for stability bracket at 100 µg rPA/mL and 500 µg rPA/mL. The formulations were stored at −20° C., 5° C., and 25° C. and stability was assessed at 1, 3,6 and 9 months. Formulations were also placed at 40° C. and analyzed at 1, 3 and 6 months. The stability assays include: physical appearance, pH, particle size, and qualitative Western Blots. rPA recovery was determined by RP-HPLC and SEC-HPLC.

The purpose of this set was to select the best concentration of trehalose to be incorporated in a TRIS buffered system. rPA aqueous systems showed equivalent stability profiles except for the low dose rPA aqueous system. The low dose (100 µg/mL rPA aqueous system) was stable for 6 months at 5° C., while all the other systems were stable at 9 months at 5° C. The pH was stable for all the temperatures, except for 40° C. for 6 months. This is an improvement in the pH stability profile as compared to the Prototype 1 formulations. The rPA potency by RP-HPLC/SEC-HPLC best shows the stability differentiation of the formulations. The potency of rPA in the rPA aqueous systems at the 25° C. condition from 1 to 6 months ranges from 40-85%.

Figure 19:
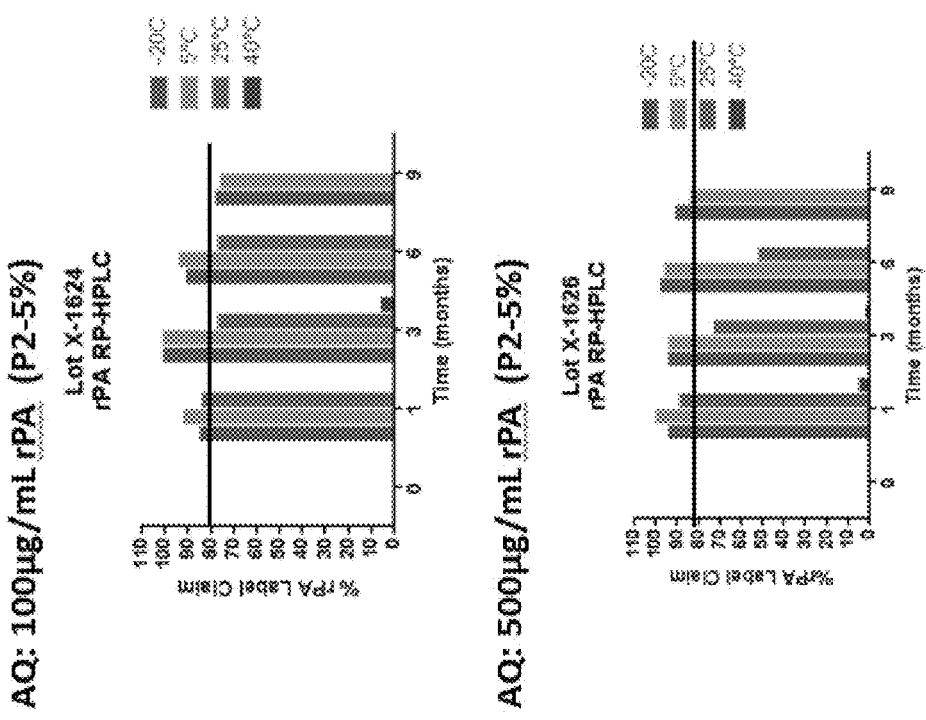
FIG. 19 shows rPA aqueous (AQ) (5% Trehalose) formulations by temperature and month.
Figure 20:
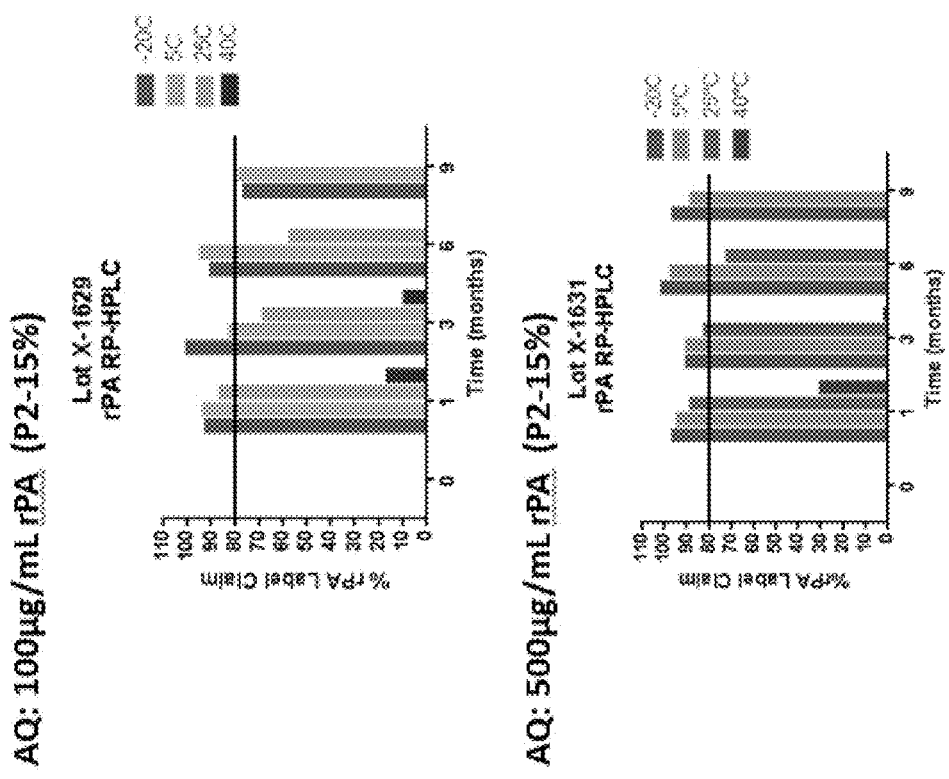
FIG. 20 shows rPA aqueous (AQ) (15% Trehalose) formulations by temperature and month.

With respect to the level of trehalose, the benefit of increasing the trehalose from 5% to 15% is clearly demonstrated in FIGS. 19-20.

This increase in levels of stable rPA indicates that the additional trehalose helps protect rPA at high temperatures over a longer duration of time as compared to 5% trehalose.

Example 12—Stability Data of Prototype 3 (TRIS Buffered System with/without Glutathione) Formulations The third prototype was two sets of formulations with or without 16 mM Glutathione in a TRIS buffered system as shown in Table 9. The rPA concentrations are bracketed at 100 µg rPA/mL and 500 µg rPA/mL. The formulations were stored at −20° C., 5° C., and 25° C., and stability was assessed at 1, 3 and 6 months. Formulations were also placed at 40° C. and analyzed at 1, 3 and 6 months. The stability assays include: physical appearance pH, particle size, and qualitative Western Blots. The Western blots were performed using the harmonized Western Blot method for rPA and the Novus rabbit polyclonal whole sera antibody as the primary antibody. The rPA recovery was determined by RP-HPLC and SEC-HPLC.

The purpose of this set of prototypes was to understand the contribution of glutathione and histidine when incorporated in a TRIS buffered system.

Figure 22:
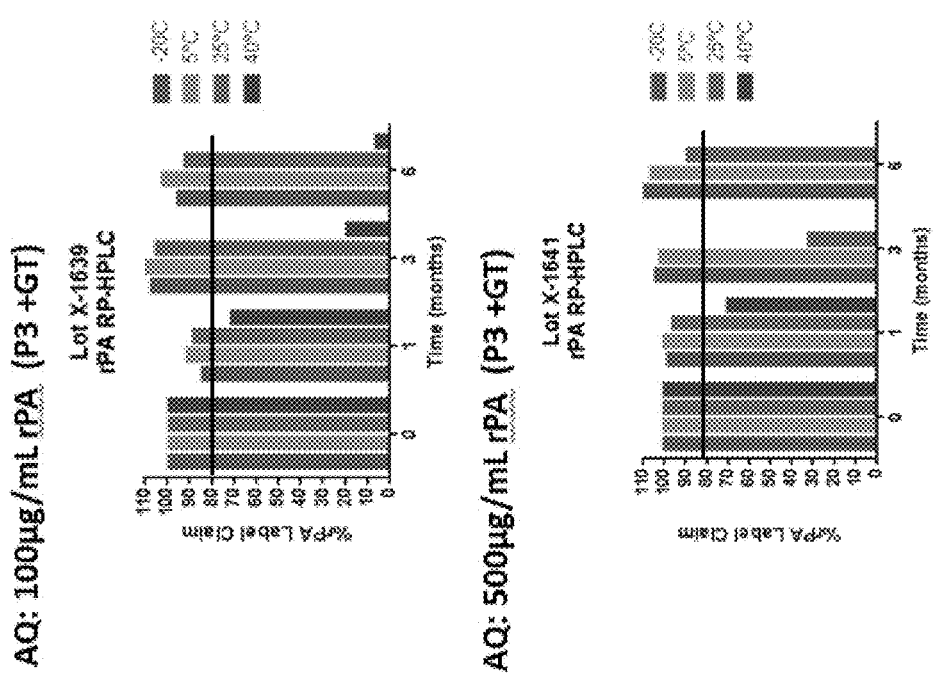
FIG. 22 shows rPA aqueous (AQ) (P3+GT) formulations by temperature and month.
Figure 23:
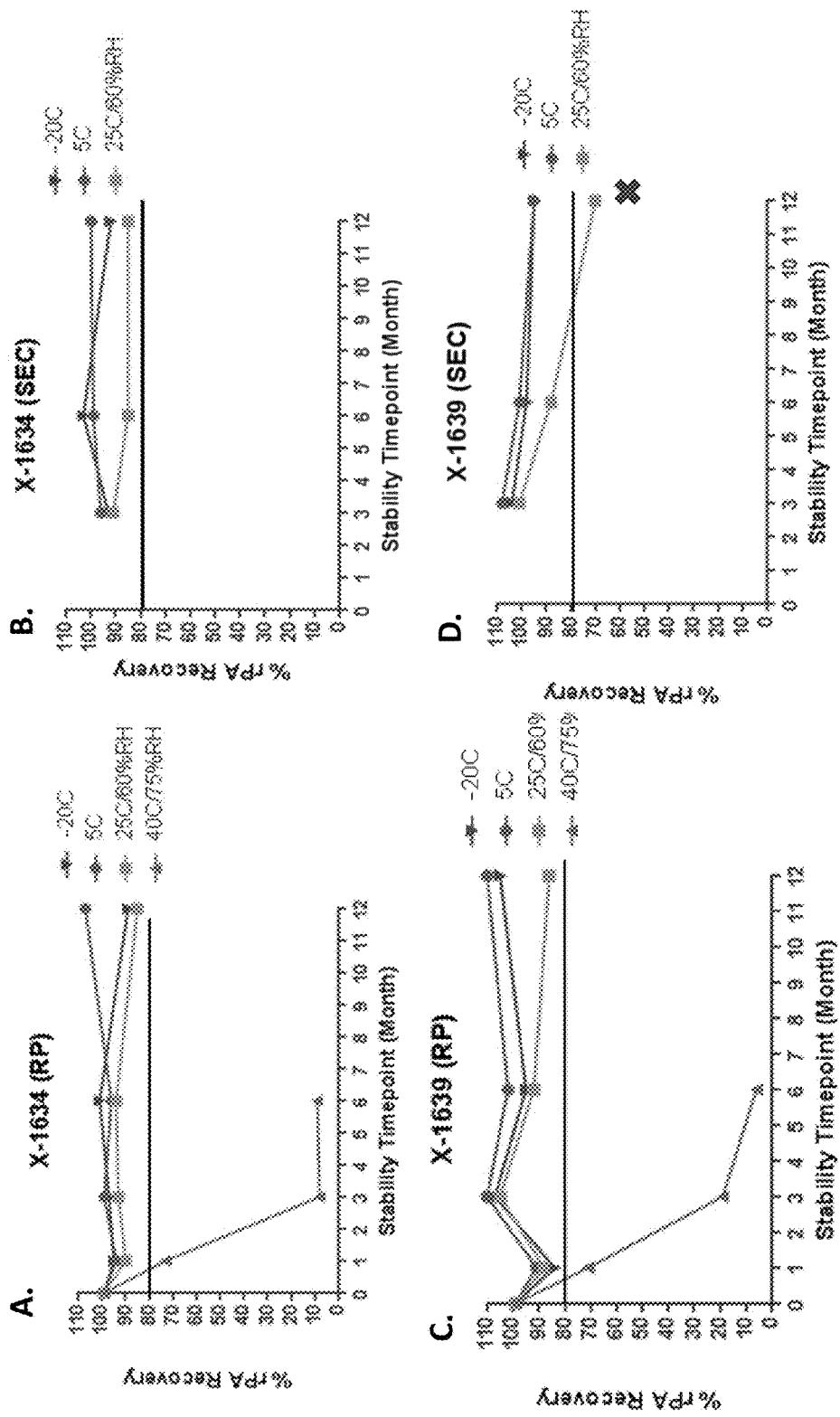
FIG. 23 shows rPA Aqueous solution stability of low dose rPA over 12 months. Panels (A) and (B) show formulations without glutathione and panels (C) and (D) show formulations with glutathione.
Figure 24:
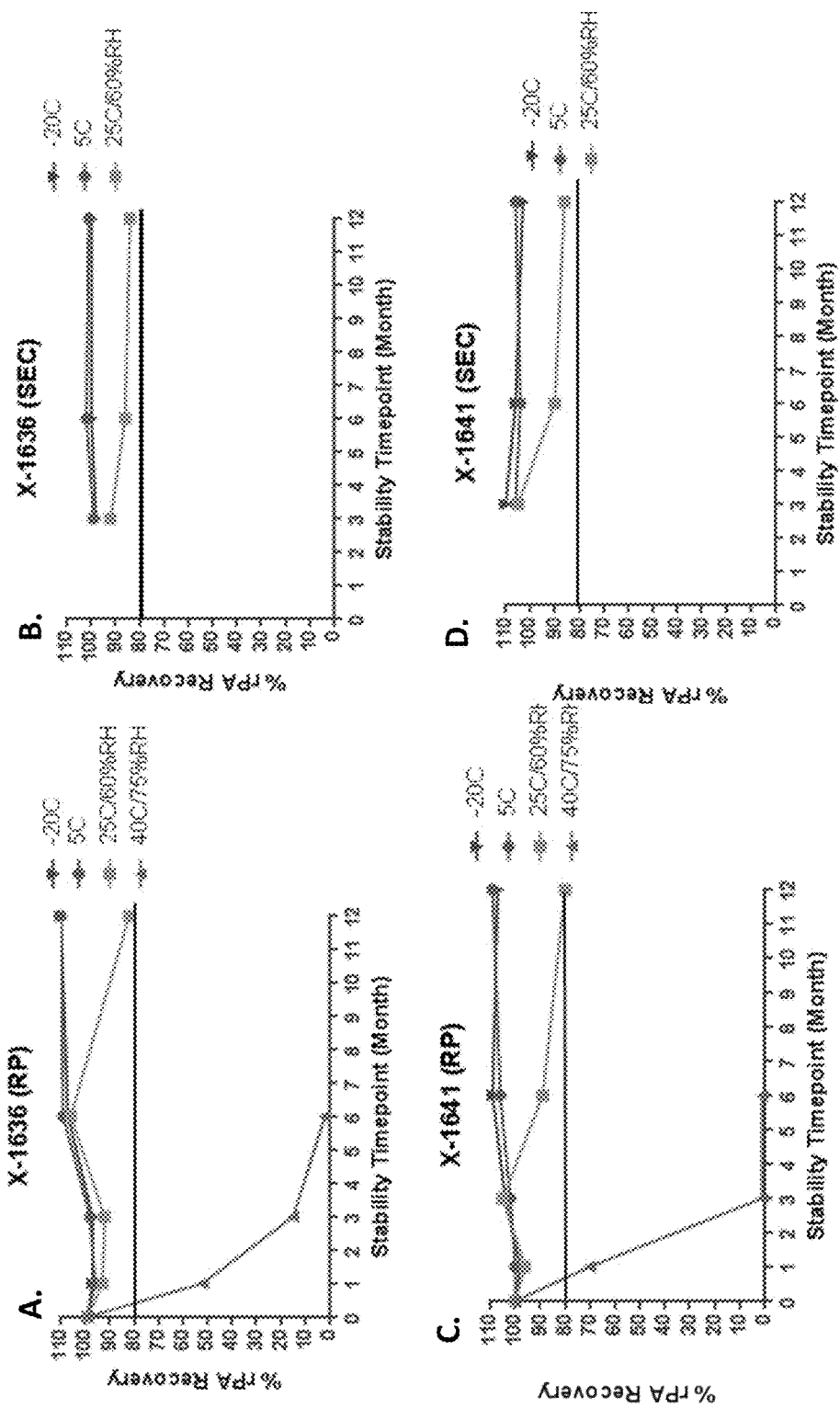
FIG. 24 shows rPA aqueous solution stability of high dose rPA aqueous solutions. 12 months of rPA stability was measured after storage at −20 C, 5 C, 25° C. (RP/SEC, +GT). Panels (A) and (B) show formulations without glutathione and panels (C) and (D) show formulations with glutathione.

FIGS. 21 and 22 show the rPA recovery over time and temperatures for the rPA aqueous systems. The rPA recovery in the rPA aqueous systems at 25° C. was above 80% for every formulation tested. This is an improvement over the rPA aqueous systems from Prototype 2 which ranged from 40% to 80%.

With respect to the addition of glutathione, there does not appear large benefit of this excipient for rPA stability. When rPA potency is compared with and without glutathione, there is little effect on rPA recovery when measured using RP-HP TABLE 19-continued Composition of Prototype 2 Formulations Prototype 2 Excipient Compositions

| Lot # | Type | rPA conc (μg/mL) | % NE | Buffer System | NaCl (mM) | Histidine (mM) | Trehalose (%) | L-Glutathione (mM) | EDTA (mM) |
|---|---|---|---|---|---|---|---|---|---|
| X-1626 | rPA | 500 | 0 | 80 mM TRIS | 150 | 20 | 5 | 16 | 0.5 |
| X-1627 | NE + rPA | 500 | 20 | 80 mM TRIS | 150 | 20 | 5 | 16 | 0.5 |
| X-1628 | NE | 0 | 20 | 80 mM TRIS | 150 | 20 | 5 | 16 | 0.5 |
| X-1629 | rPA Control | 100 | 0 | 80 mM TRIS | 150 | 20 | 15 | 16 | 0.5 |
| X-1630 | NE + rPA | 100 | 20 | 80 mM TRIS | 150 | 20 | 15 | 16 | 0.5 |
| X-1631 | rPA Control | 500 | 0 | 80 mM TRIS | 150 | 20 | 15 | 16 | 0.5 |
| X-1632 | NE + rPA | 500 | 20 | 80 mM TRIS | 150 | 20 | 15 | 16 | 0.5 |
| X-1633 | NE | 0 | 20 | 80 mM TRIS | 150 | 20 | 15 | 16 | 0.5 |

TABLE 20

Composition of Prototype 3 Formulations

Prototype 3 Excipient Compositions

| | Type | rPA conc (μg/mL) | % NE | Buffer System | NaCl (mM) | Histidine (mM) | Trehalose (%) | L-Glutathione (mM) |
|---|---|---|---|---|---|---|---|---|
| X-1634 | Rpa | 100 | 0 | 80 mM TRIS | 150 | 60 | 15 | 0 |
| X-1635 | NE + r TABLE 21-continued Overall Summary of 100 μg/mL rPA Formulations in 10 mM Phosphate buffer with 100 mM NaCl.

| Time Point | Storage Condition | Physical Appearance | pH (±0.5) | CPC (90-110%) | Particle Size (nm) | PdI | Western Blott (~83 kD Band) | rPA - HPLC RP (SEC) (>80%) |
|---|---|---|---|---|---|---|---|---|
| | | 100 μg/ml rPA + 20% W$_{80}$5EC in PBS (X-1669) | | | | | | |
| 0 | Initial | Pass | 7.37 | 94.4 | 437 | 0.137 | Band | 104 (102) |
| 1 month | 5° C. | Pass | 7.28 | 94.3 | 442 | 0.153 | Band | 85 (98) |
| | 25° C./60% RH | Pass | 6.93 | 91.3 | 443 | 0.130 | No Band | 4 (0) |
| | 40° C./75% RH | Fail | 6.35 | 78.8 | 452 | 0.162 | No Band | 0 (0) |
| 3 month | 5° C. | Pass | 7.37 | 93.5 | 455 | 0.211 | Band | 90 (105) |
| | 25° C./60% RH | Pass | 5.69 | 79.6 | 444 | 0.159 | No Band | 3 (0) |
| | 40° C./75% RH | Fail | 3.95 | 65.3 | 470 | 0.192 | No Band | 0 (0) |

TABLE 22

Overall Summary of 500 μg/mL rPA Formulations in 10 mM Phosphate buffer with 100 mM NaCl.

| Time Point | Storage Condition | Physical Appearance | pH (±0.5) | CPC (90-110%) | Particle Size (nm) | PdI | Western Blott (~83 kD Band) | rPA - HPLC RP (SEC) (>80%) |
|---|---|---|---|---|---|---|---|---|
| | | 500 μg/ml rPA in PBS (X-1670) | | | | | | |
| 0 | Initial | Pass | 7.49 | — | 8.45 | — | Band | 95 (98) |
| 1 month | 5° C. | Pass | 7.43 | — | 8.3 | — | Band | 97 (100) |
| | 25° C./60% RH | Pass | 7.46 | — | 7.4 | — | Band | 95 (97) |
| | 40° C./75% RH | Fail | 7.57 | — | 0 | — | Lt Band | 5 (3) |
| 3 month | 5° C. | Pass | 7.52 | — | 8.2 | — | Band | 101 (105) |
| | 25° C./60% RH | Pass | 8.14 | — | 0 | — | No Band | 0 (0) |
| | 40° C./75% RH | Fail | 7.67 | — | 0 | — | No Band | 0 (0) |
| | | 500 μg/ml rPA + 20% W$_{80}$5EC(83083) in PBS (X-1671) | | | | | | |
| 0 | Initial | Pass | 7.50 | 100 | 433 | 0.159 | Band | 100 (103) |
| 1 month | 5° C. | Pass | 7.46 | 91.9 | 463 | 0.131 | Band | 83 (87) |
| | 25° C./60% RH | Fail | 7.36 | 89.4 | 452 | 0.122 | Lt Band | 2 (1) |
| | 40° C./75% RH | Fail | 6.75 | 78.4 | 456 | 0.153 | No Band | 0 (0) |
| 3 month | 5° C. | Pass | 7.45 | 91.7 | 442 | 0.139 | Band | 91 (92) |
| | 25° C./60% RH | Fail | 7.05 | 83.7 | 449 | 0.178 | No Band | 0 (0) |
| | 40° C./75% RH | Fail | 4.24 | 60.6 | 502 | 0.239 | No Band | 0 (0) |

TABLE 23

Overall Summary of 20% W$_{80}$5EC Nanoemulsion Formulation in 10 mM Phosphate buffer with 100 mM NaCl.

| Time Point | Storage Condition | Physical Appearance | pH (±0.5) | CPC (90-110%) | Particle Size (nm) (±200 nm) | PdI (>0.25) |
|---|---|---|---|---|---|---|
| | | 20% W$_{80}$5EC (83083) in PBS (X-1672) | | | | |
| 0 | Initial | Pass | 7.36 | 94.1 | 437 | 0.153 |
| 1 month | 5° C. | Pass | 7.34 | 93.2 | 438 | 0.121 |
| | 25° C./60% RH | Pass | 6.52 | 85.2 | 448 | 0.139 |
| | 40° C./75% RH | Fail | 4.29 | 76.6 | 452 | 0.122 |
| 3 months | 5° C. | Pass | 6.82 | 91.5 | 437 | 0.130 |
| | 25° C./60% RH | Pass | 4.07 | 76.6 | 461 | 0.207 |
| | 40° C./75% RH | Fail | 3.70 | 68.1 | 441 | 0.161 |

Example 15—Analytical Methods Used in the Stability Studies

The various formulations were filled into 1.8 mL or 4 mL Type 1 glass vials with a PTFE-lined screw cap. The stability parameters assessed for these formulations were physical appearance, pH, mean particle size, cetylpyridinium chloride potency (% CPC label claim), non-quantitative Western blot for 83 kDa rPA and rPA by RP-HPLC and SEC-HPLC. Dynamic light scattering using the Malvern Zetasizer was used to determine particle size, particle size distribution profiles and a polydispersity index. Table 24 shows the methods that were developed and the acceptable criteria for each method.

TABLE 24

Test method and acceptance criteria for the formulations placed on informal stability.

| Stability Parameter | Test Method | Acceptance Criteria for Each Formulation Type | | |
|---|---|---|---|---|
| | | rPA Buffered Solution (rPA Aqueous) | rPA + 20% $W_{80}5EC$ in Buffered Solution (FVF) | 20% $W_{80}5EC$ in Buffered Solution(NE) |
| Physical Appearance | Visual | No Precipitation and/or Cloudy Solution | No Phase Separation and Precipitation | No Phase Separation |
| pH | pH Meter | +/−0.5 | +/−0.5 | +/−0.5 |
| Particle Size | Dynamic Light Scattering | Absent Peak 8-20 nm | Z-Ave: +/−200 nm | Z-Ave: +/−200 nm |
| PdI | Dynamic Light Scattering | — | Less than 0.25 | Less than 0.25 |
| Cetylpyridinium Chloride Potency | RP-HPLC | — | +/−10% | +/−10% |
| 83 kD Band | Western Blot | Band Presnt | Band Present | — |
| rPA Potency Label Claim | SEC-HPLC RP-HPLC | Not Less than 80% + No Band | Not Less than 80% + No Band | — |

Example 16—Physical Appearance Test Method

Observations of physical appearance were recorded according to the nanoemulsion stability assessment shown below. Physical appearance of the formulations was determined at the initial time point and upon various storage conditions. The physical appearance observation was then recorded and evaluated using the acceptance criteria in Table 25. FIGS. 26 and 27 illustrate examples of the acceptance criteria for rPA buffered aqueous solutions: FIG. 26 shows examples of rPA buffered aqueous solutions, with the first two vials being acceptable and the second two failing the stability test. FIG. 27 shows examples of rPA+nanoemulsion buffered aqueous solutions, with the first vial being acceptable and the second two vials failing due to phase separation (demonstrating instability of the formulations).

TABLE 25

Stability Parameters, Description and Acceptance Criteria

| Stability Parameter | Description | Acceptance Criteria | |
|---|---|---|---|
| Color | A white to off white liquid | A white to off white liquid acceptable.<br>Yellow (light to dark), tan, and shades of brown not acceptable. | |
| Creaming | A white, creamy layer on top of the emulsion that is more opaque than the rest of the emulsion. Remixing will restore homogeneity. | Presence (+) or absence (−)<br>All stages of creaming are acceptable | |
| Settling | A gradual decrease in opacity of the emulsion from top to bottom. Remixing will restore homogeneity. | Mild-cloudiness gradient from top to bottom (no defining layers)<br>Moderate-clear at bottom of vial with increasing opacity toward the cap<br>Severe-3-4 distinct layers<br>Extreme-only 2 layers<br>All stages of settling are acceptable | |
| Phase Separation | Separation of the oil and water phases of the emulsion. Remixing will not restore homogeneity. | PasPass:<br>None<br>Insignificant-a few droplets are visible at surface<br>Mild-oil layer equals <1% of total height | Fail:<br>Moderate-a film of oil >1% of emulsion height<br>Severe-3 distinct layers<br>Extreme-total separation into 2 phases (oil and water) |

Example 17—pH Assessment

The pH was measured using a standard pH meter with the appropriate probe that can be used for both TRIS and PBS buffer systems.

Example 18—Mean Particle Size Analysis and Polydispersity Index (PdI)

The mean particle size (Z-average) and polydispersity index (PdI) were determined for all the stability samples. The particle size and PdI of the sample was measured by photon correlation spectroscopy using a Malvern Zetasizer Nano ZS90 (Malvern Instruments, Worcestershire, UK), according to the Malvern user's manual for Particle Sizing (Malvern). All measurements were carried out at 25° C. after dilution to 1% nanoemulsion with specific external phase buffer system with stabilizing excipients. The rPA aqueous systems were not diluted.

Example 19—Reverse Phase HPLC for CPC Determination

The RP-HPLC analysis was used for determining the cetylpyridinium chloride (CPC) concentration in 20% $W_{80}5EC$ nanoemulsions (NE) formulations comprising 100 µg/mL or 500 µmg/mL recombinant Protective Antigen (rPA). The chronographic conditions are provided in the tables below to determine the concentration of CPC in accelerated stability samples with 20% $W_{80}5EC$.

Table 26 describes the RP-HPLC conditions. Briefly, 200 µL of the sample was added to about 8 mL of Mobile Phase. The composition was then mechanically shaken about 15 minutes to dissolve the emulsion completely and then diluted to a final volume of 10 mL with mobile phase. The sample preparation was filtered with a 0.45 µm PTFE filter, with discarding the first 3 mL of the filtrate.

TABLE 26

| RP-HPLC Chromatographic Conditions | |
|---|---|
| Flow Rate: | 1.0 mL/minute |
| Column: | Waters Symmetry C-18, 5-µm, 150-mm × 3.9-mm |
| Column Temperature: | 30° C. |
| Autosampler Temperature: | 15° C. |
| Injector Volume: | 100 µL |
| Detector Wavelength: | 260 nm |
| Run Time: | 30 minutes |
| Retention Time: | About 10.5 minutes |

Example 20—Reverse Phase HPLC for rPA Determination

The RP-HPLC analysis was used for determining the recombinant Protective Antigen (rPA) concentration in 20% $W_{80}5EC$ nanoemulsions (NE) formulations comprising 100 µg/mL or 500 µmg/mL recombinant Protective Antigen (rPA) and 100 µg/mL or 500 µg/mL rPA in aqueous buffered solutions systems. The RP-HPLC chromtographic conditions are provided in Tables 27 and 28 below to determine the concentration of rPA in accelerated stability samples with 20% $W_{80}5EC$ or in aqueous buffered solutions.

To assay rPA in the nanoemulsion formulations, the rPA needed to be extracted. Briefly, 0.5 mL of the stability sample (rPA+20% W805EC) and 0.5 mL 2M Sodium Sulphate ($Na_2SO_4$) solution were mixed together for 1 minute. The mixture was then centrifuged at 1000 rpm for 4 minutes. 0.4 mL of the clear layer was removed, placed into a 1.8 mL HPLC vial, and 0.6 mL of PBS (1×) was added. The composition was mixed for 30 seconds and assayed via RP-HPLC.

TABLE 27

| RP-HPLC Chromatographic Conditions | |
|---|---|
| Column: | ACE 5 Phenyl-300, 100 × 4.0 min id, ACE Part Number: ACE-225-1004 |
| Elution Type | Gradient |
| Flow Rate | 0.5 mL/minute |
| Column Temperature: | 45° C. |
| Buffer A | 0.05% Trifluoroacetic Acid (TFA) in Water |
| Buffer B | 0.04% Trifluoroacetic Acid (TFA) in Acetonitrile |
| Auto Sampler Temperature: | 4° C. |
| Injector Volume: | 10 µL (for 0.5 mg/mL rPA strength); 50 µL (for 0.1 mg/mL rPA strength) |
| Detector Wavelength: | 214 nm |
| Run Time: | 37.5 minutes - gradient (See table below Table 13) |
| Retention Time: | 12.5 minutes |

TABLE 28

Gradient Settings

| # Gradient Steps | Time (minutes.) | Flow (mL/ minutes) | % A | % B | % C | % D | Curve |
|---|---|---|---|---|---|---|---|
| 1 | | 0.5 | 70.0 | 30.0 | 0 | 0 | 6 |
| 2 | 5.0 | 0.5 | 70.0 | 30.0 | 0 | 0 | 6 |
| 3 | 27.5 | 0.5 | 25.0 | 75.0 | 0 | 0 | 6 |
| 4 | 29.5 | 0.5 | 0.00 | 100.0 | 0 | 0 | 6 |
| 5 | 33.5 | 0.5 | 90.0 | 10.0 | 0 | 0 | 6 |
| 6 | 34.5 | 0.5 | 70.0 | 30.0 | 0 | 0 | 6 |
| 7 | 37.5 | 0.5 | 70.0 | 30.0 | 0 | 0 | 6 |

Example 21—Size Exclusion HPLC for rPA Determination

The SEC-HPLC analysis was also used for determining the recombinant Protective Antigen (rPA) concentration in 20% $W_{80}5EC$ nanoemulsions formulations comprising 100 µg/mL or 500 µg/mL recombinant Protective Antigen (rPA) and 100 µg/mL or 500 µg/mL rPA in aqueous buffered solutions systems. The chromatographic conditions are provided in Table 29 to determine the concentration of rPA in accelerated stability samples with 20% $W_{80}5EC$ or in aqueous buffered solutions.

To assay rPA in the nanoemulsion formulations, the rPA needs to be extracted. Briefly, 0.5 mL the stability sample (rPA+20% $W_{80}5EC$) and 0.5 mL 2M Sodium Sulphate ($Na_2SO_4$) solution are mixed together for 1 minute. The mixture is then centrifuged at 1000 rpm for 4 minutes. 0.4 mL of the clear layer is removed, and then placed into a 1.8 mL HPLC vial, and 0.6 mL of PBS (1×) is added. The composition is mixed for 30 seconds and assayed via SEC-HPLC.

TABLE 29

SEC-HPLC Chromatographic Conditions

| Parameter | Setting |
|---|---|
| Separation Mode | SEC |
| Stationary Phase | Tosoh Bioscience TSK-GEL G3000SWxL, 7.8 mm, 10 × 300 mm, L |
| Column Temperature | 25° C. |
| Run Time | 30 minutes |
| Flow Rate | 0.5 mL/min |
| Gradient/Isocratic | Isocratic |
| Mobile Phase | 0.1M Sodium Phosphate, 0.1M Sodium Sulfate, pH 6.8 |
| Sample Temperature | 4° C. |
| Injection Volume | 10 µL for formulations containing 0.5 mg/mL rPA 50 µL for formulations containing 0.1 mg/mL rPA |
| Detector Wavelength | 220 nm |
| Retention Time | 17.7 minutes |

Example 22—Western Blot Method for rPA

The Western blot used a Novus Primary Antibody that has been raised against *B. anthracis*. The Western blot was used in a qualitative manner to help screen candidate formulations by analysis for product related aggregates and degradants and the method parameters are shown in Table 30.

TABLE 30

Western Blot Method for rPA

| | |
|---|---|
| Sample Preparation | Treated with SDS, beta-mercaptoethanol Heat at 70° C. for 10 minutes Sample amount = 0.250 µg/lane |
| Instrument | Invitrogen Xcell System, and Power Ease 500 Electrophoresis Power Supply |
| Gel | Novex ™ NuPage 4-12% Bis-Tris Gel |
| Electrophoresis | 125 V for 120 minutes MES SDS running buffer |
| Blot Transfer | Nitrocellulose membrane (iBlot stacks) Semi-dry transfer (iBlot), P3 (20 v for 7 minutes) |
| Blot Blocking | WesternBreeze Blocking Solution Block at RT for 30 minutes |
| Blot Wash | WesternBreeze Antibody Wash solution |
| Primary antibody | Rabbit polyclonal whole sera, NOVUS Cat# NB120-13808 (1:1000) Incubate at RT for 60 minutes or 4 C. overnight |
| Secondary antibody | Western Breeze AP-Anti-Rabbit Secondary Antibody Solution Incubate at RT for 30 minutes |
| Substrate | BCIP/NBT AP substrate |

Figure 42:
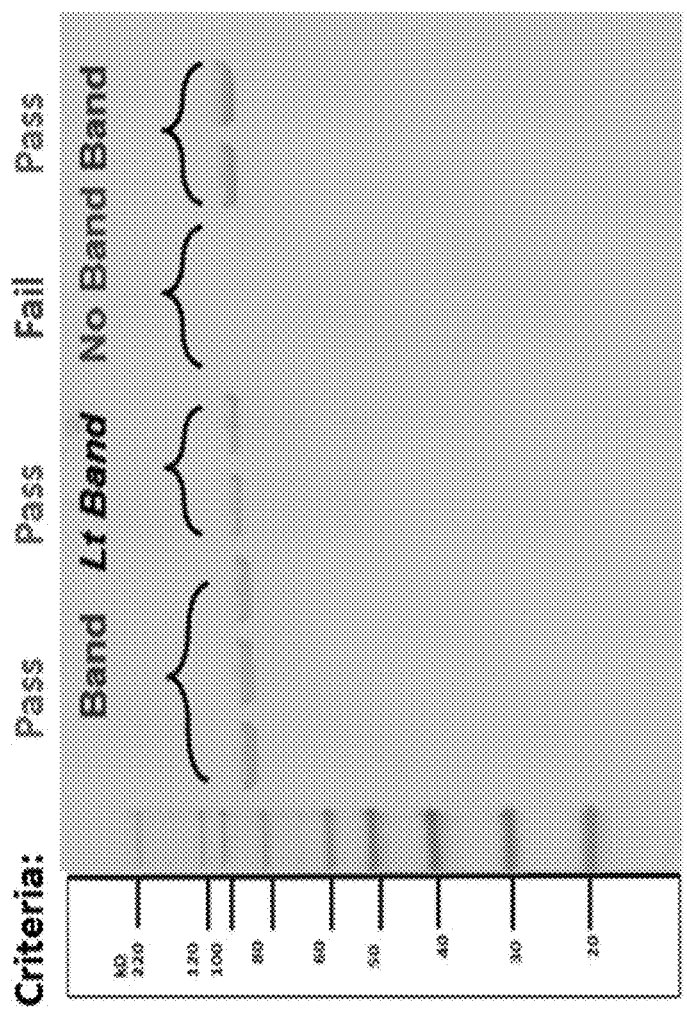
FIG. 42 shows the acceptance criteria for the qualitative Western Blot method.
Figure 43:
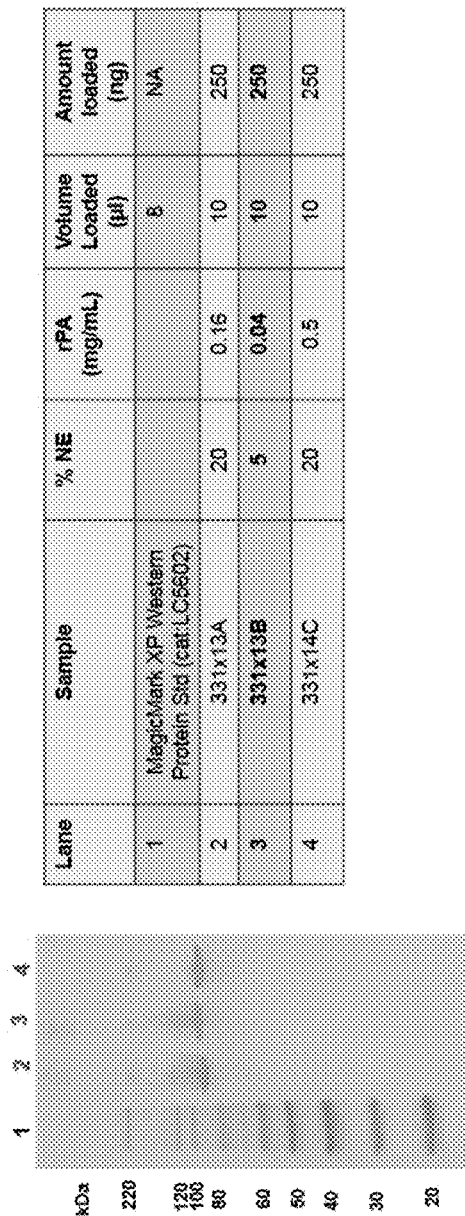
FIG. 43 shows Western blot data for NE-rPA+Phosphate buffer: Aggregate bands seen at 100, 120 and 220 kDa for 2 concentrations (lanes 2 and 3). The 0.5 mg/mL+20% NE (lane 4) shows a light 220 kDA band.
Figure 44:
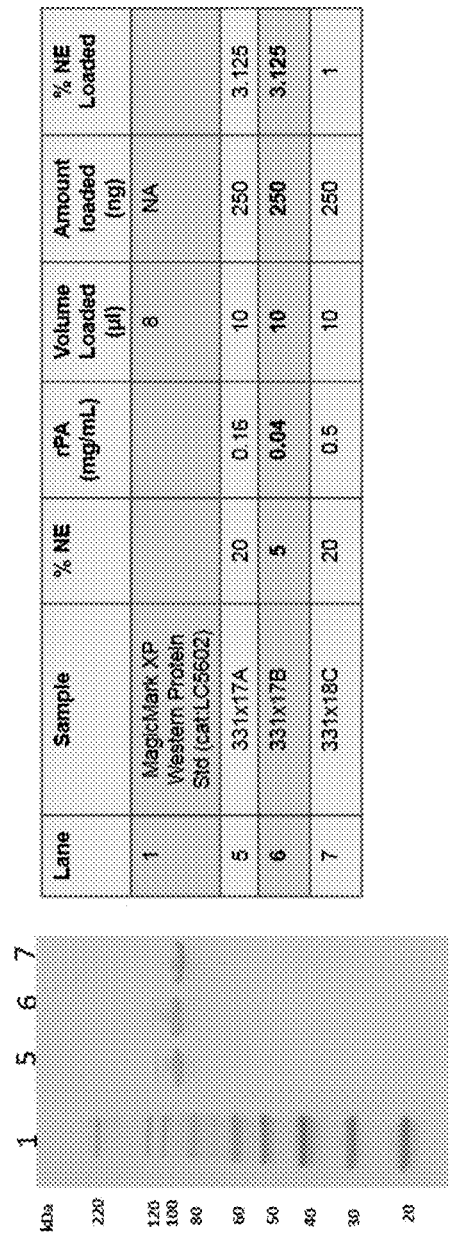
FIG. 44 shows Western blot data for NE-rPA-Phosphate Buffer-100 mM NaCl-Histidine-Sucrose: Aggregate bands seen at ~100 kDa for the 2 low rPA concentrations (lanes 5 and 6), but much reduced as compared to NE-rPA+Phosphate buffer system. The 0.5 mg/mL+20% NE (lane 7) shows no larger molecular wt bands present.
Figure 45:
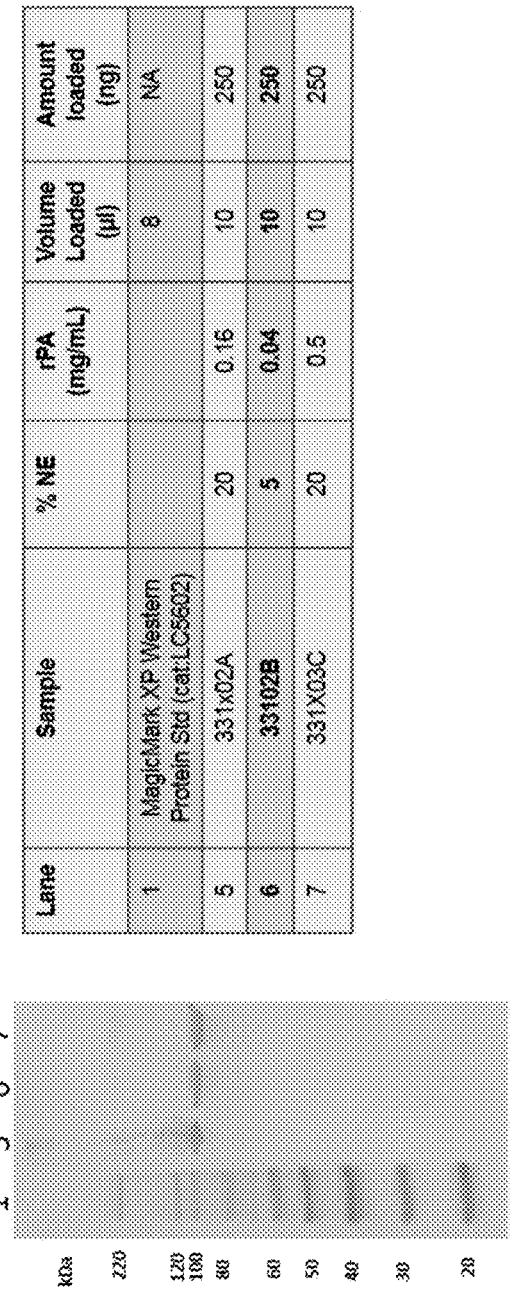
FIG. 45 shows Western blot data for NE-rPA+Tris buffer: 100, 120 and 220 kDa aggregate in Stock (#5) but not in diluted 0.04 mg/mL concentration. The 0.5 mg/mL+20% NE (#7) shows a light 220 kDA band.
Figure 46:
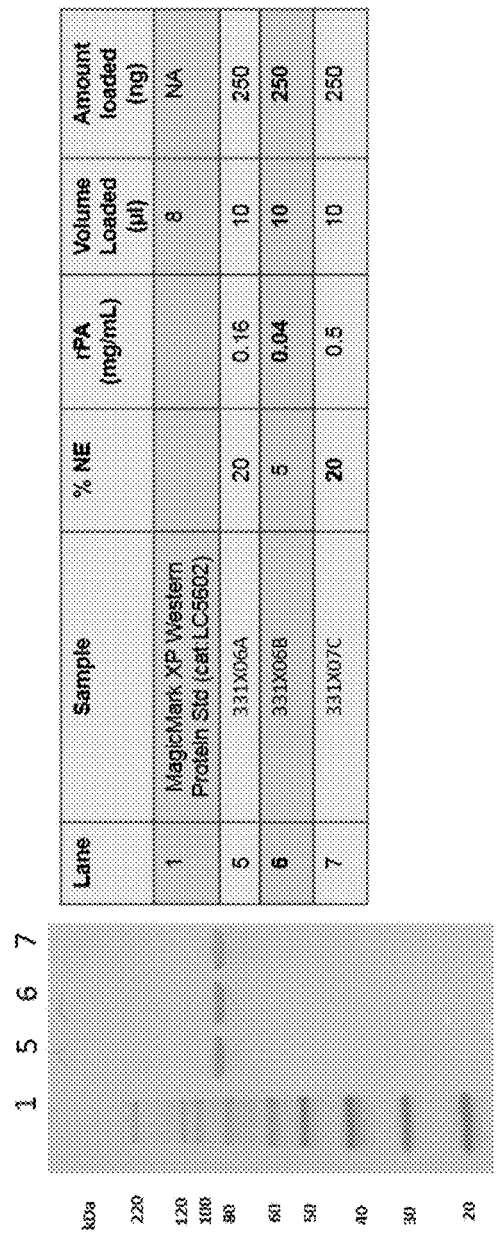
FIG. 46 shows Western blot data for NE-rPA-TRIS Buffer-150 mM NaCl– Histidine-Sucrose: No aggregate bands present at any rPA concentration.

Examples of the acceptance criteria for the qualitative Western Blot method are shown in FIG. 42. If there is an 83 kDA band present or a light band, then it was considered to pass, as shown in lanes 1-5 after the molecular weight ladder. If no band is present, as shown in lanes 7 and 8, that was considered a failure.

Example 23—Mixing Protocol for rPA Nanoemulsion Formulations

The mixing scheme for a 50 gram batch is shown in FIG. 28 (Optimized Mixing procedure for the rPA+Nanoemulsion with stabilizing buffer). The batch size was 50 grams.

For the 500 rPA formulation, 5 g of the rPA stock (concentration of rPA is 5 mg/mL) is mixed with 16.67 g of 60% $W_{80}5EC$ nanoemulsion adjuvant by simple inversion for 30 seconds. The formulation was then allowed to incubate for 10 minutes at room temperature to allow the rPA to migrate into the core of the nanoemulsion droplets. Than 28.33 g of the stabilizing buffer was added and gently mixing by inversion for 30 seconds. The stabilizing buffer is composed of a buffer and other stabilizing excipients. The final formulation contained either 500 µg/mL rPA with 20% $W_{80}5EC$ nanoemulsion adjuvant in a stabilizing buffer system.

For the 100 µg/mL rPA formulation, 1 g of the rPA stock (concentration of rPA is 5 mg/mL) is mixed with 4 g of rPA buffer (25 mM sodium phosphate with 150 mM sodium chloride, pH 8). This mixture of 5 g is than added to 16.67 g of 60% $W_{80}5EC$ nanoemulsion adjuvant by simple inversion for 30 seconds. The formulation was then allowed to incubate for 10 minutes at room temperature to allow the rPA to migrate into the core of the nanoemulsion droplets. Than 28.33 g of the stabilizing buffer was added and gently mixing by inversion for 30 seconds. The stabilizing buffer is composed of a buffer and other stabilizing excipients. The final formulation contained either 100 µg/mL rPA with 20% $W_{80}5EC$ nanoemulsion adjuvant in a stabilizing buffer system.

Example 24—Prototype 1 Formulations

The purpose of this example was to select the best buffer system (e.g. PBS or TRIS) for the rPA formulations since the base formulation (e.g. phosphate buffered system) was unstable. Also, two stabilizing excipients, sucrose and histidine, were added to aid in stabilizing the prototype protein antigen, recombinant anthrax rPA. These formulations were then placed on stability. FIG. 2 shows the formulation design and the formulations are described in Table 18.

Figure 29:
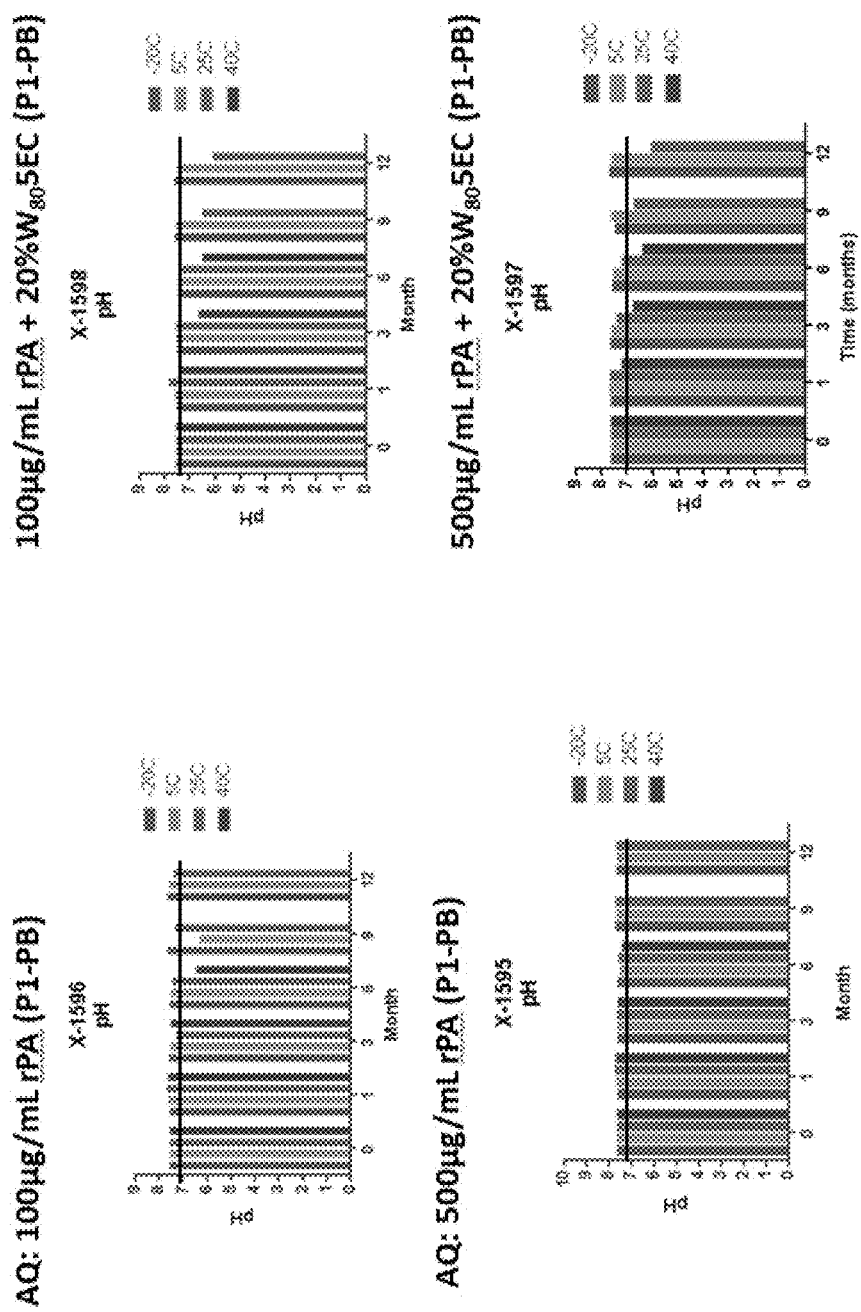
FIG. 29 shows the pH over time at different temperatures of different prototype protein formulations: aqueous rPA, rPA+nanoemulsion (20% $W_{80}5EC$ (PBS)).
Figure 30:
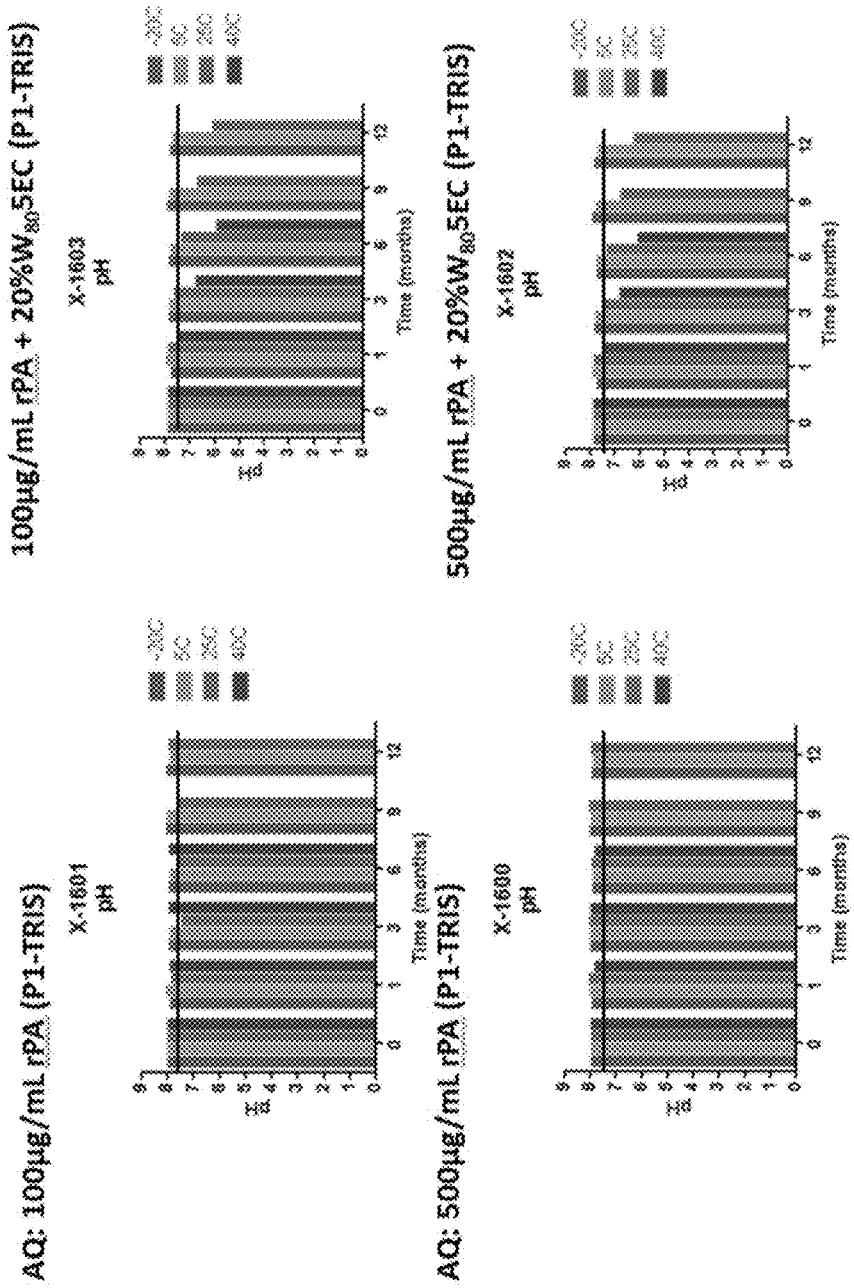
FIG. 30 shows the pH over time at different temperatures of different prototype protein formulations: aqueous rPA, rPA+nanoemulsion (20% $W_{80}5EC$ (TRIS)).

The rPA aqueous systems exhibited a better stability profile than rPA+20% $W_{80}5EC$ with either buffer system. The pH also showed a decrease over time when stored at higher stability temperatures as shown in FIG. 29 (PBS) and FIG. 30 (TRIS).

The low dose rPA solution (X-1596-Table 31) had a longer stability profile (stable at 12 months at 5° C.) as compared to the low dose rPA+20% $W_{80}5EC$ formulation (X-1598) of 3 months at 5° C. However, the low dose X-1598 (rPA+20% $W_{80}5EC$: Prototype 1) had a better stability profile than the low dose rPA in PBS (X-1669), which was only 1 month at 5° C. The high dose rPA solution (X-1595-Table 31) also showed 12 months stability at 5° C.

The high dose rPA+20% $W_{80}5EC$ (X-1597-Table 31) was stable for 6 months at 5° C. compared to the low dose rPA+20% $W_{80}5EC$ (X-1598), which was only 3 month at 5° C.

The 20% $W_{80}5EC$ nanoemulsion adjuvant (X-1599-Table 31 was stable for 12 months at 5° C. The formulation formulated in TRIS buffer showed similar results (Table 32).

It was evident that the formulations comprising both rPA+20% $W_{80}5EC$ that the TRIS System was superior to PBS in stabilization of the prototype antigen rPA. At low dose 100 µg/mL rPA, the PBS system showed rPA stability at 3 months at 5° C. However, at high dose 500 µg/mL rPA, the PBS system only had 6 months at 5° C., while the TRIS system provided stability of rPA for 12 months at 5° C. for the high dose with over 80% rPA being retained (data not shown).

TABLE 31

Overall Summary of Prototype 1: PBS System

| | | Low Dose rPA | | High Dose rPA | | |
| --- | --- | --- | --- | --- | --- | --- |
| Month | Temp | Solution (X-1596) | 100 μg/mL + 20% $W_{80}5EC$ (X-1598) | Solution (X-1595) | 500 μg/mL + 20% $W_{80}5EC$ (X-1597) | $W_{80}5EC$ + Buffer 20% $W_{80}5EC$ (X-1599) |
| 1 | −20 | Pass | Pass | Pass | Pass | Pass |
|   | 5 | Pass | Pass | Pass | Pass | Pass |
|   | 25 | Pass | Fail | Pass | Pass | Pass |
|   | 40 | Fail | Fail | Fail | Fail | Pass |
| 3 | −20 | Pass | Pass | Pass | Pass | Pass |
|   | 5 | Pass | Pass | Pass | Pass | Pass |
|   | 25 | Fail | Fail | Pass | Pass | Pass |
|   | 40 | Fail | Fail | Fail | Fail | Fail |
| 6 | −20 | Pass | Pass | Pass | Pass | Pass |
|   | 5 | Pass | Fail | Pass | Pass | Pass |
|   | 25 | Fail | Fail | Fail | Fail | Pass |
|   | 40 | Fail | Fail | Fail | Fail | Fail |
| 9 | −20 | Pass | Fail | Pass | Fail | Pass |
|   | 5 | Fail | Fail | Pass | Fail | Pass |
|   | 25 | Fail | Fail | Fail | Fail | Fail |
| 12 | −20 | Pass | X | Pass | X | Pass |
|   | 5 | Pass | X | Pass | X | Pass |
|   | 25 | Fail | X | X | X | Fail |

TABLE 32

Overall Summary of Prototype 1: TRIS System

| | | Low Dose rPA | | High Dose rPA | | |
| --- | --- | --- | --- | --- | --- | --- |
| Month | Temp | Solution (X-1601) | 100 μg/mL + 20% $W_{80}5EC$ (X-1603) | Solution (X-1600) | 500 μg/mL + 20% $W_{80}5EC$ (X-1602) | $W_{80}5EC$ + Buffer 20% $W_{80}5EC$ (X-1604) |
| 1 | −20 | Pass | Pass | Pass | Pass | Pass |
|   | 5 | Pass | Pass | Pass | Pass | Pass |
|   | 25 | Pass/Fail | Pass | Pass | Pass | Pass |
|   | 40 | Fail | Pass | Fail | Fail | Pass |
|   | −20 | Pass | Pass | Pass | Pass | Pass |
| 3 | 5 | Pass | Pass | Pass | Pass | Pass |
|   | 25 | Pass/Fail | Fail | Pass | Pass | Pass |
|   | 40 | Fail | Fail | Fail | Fail | Fail |
| 6 | −20 | Pass | Pass | Pass | Pass | Pass |
|   | 5 | Pass | Fail | Pass | Pass | Pass |
|   | 25 | Pass/Fail | Fail | Pass | Fail | Pass |
|   | 40 | Fail | Fail | Fail | Fail | Fail |
| 9 | −20 | Pass | Fail | Pass | Pass | Pass |
|   | 5 | Pass | Fail | Pass | Fail | Pass |
|   | 25 | Fail | Fail | Fail | Fail | Fail |
| 12 | −20 | Pass | Fail | Pass | Fail | Pass |
|   | 5 | Pass | Fail | Pass | Pass | Pass |
|   | 25 | Fail | X | X | X | Fail |

Example 25—Prototype 2 Formulations: TRIS with 5 or 15% Trehalose

Figure 31:
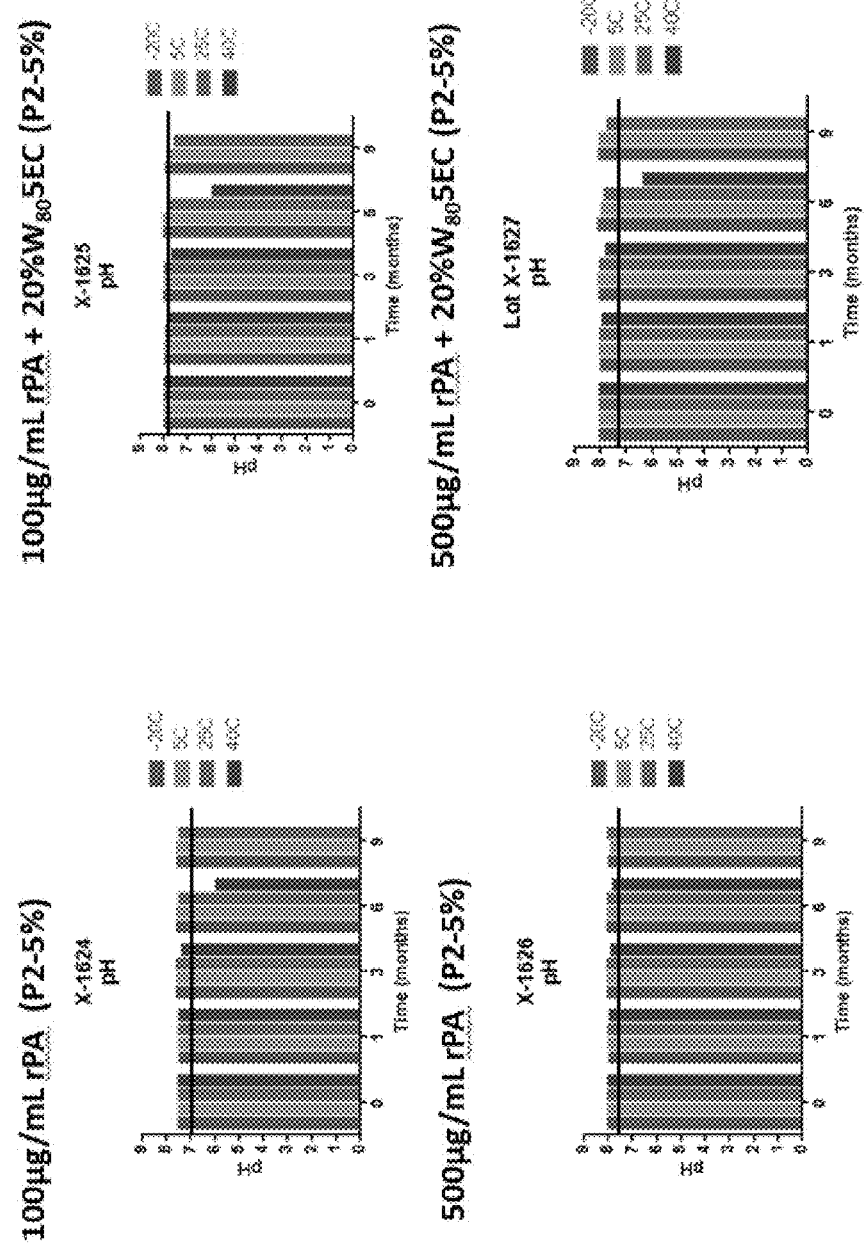
FIG. 31 shows the pH over time at different temperatures of different prototype protein formulations: aqueous rPA, rPA+nanoemulsion (20% $W_{80}5EC$ (5% Trehelose)).
Figure 32:
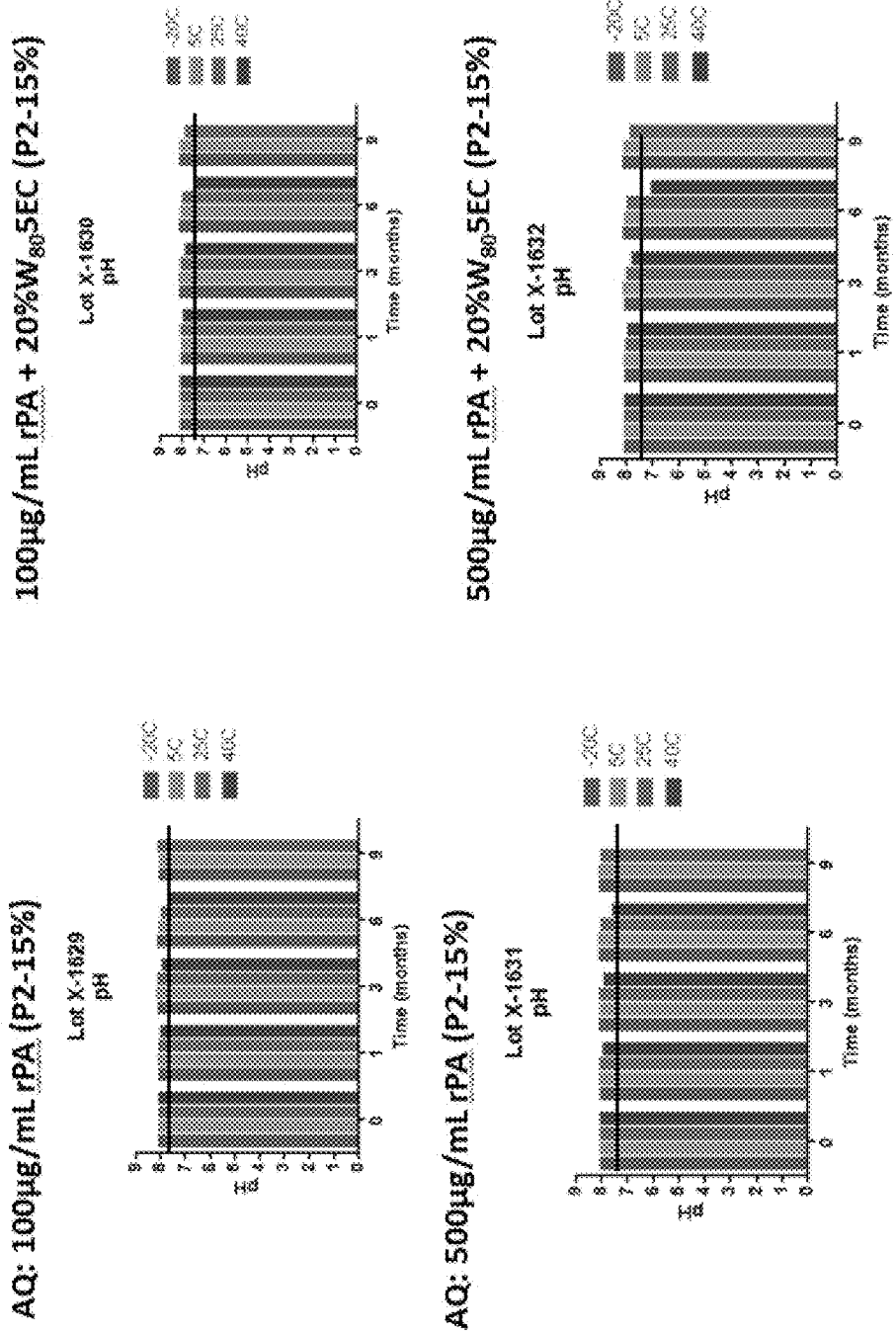
FIG. 32 shows the pH over time at different temperatures of different prototype protein formulations: aqueous rPA, rPA+nanoemulsion (20% $W_{80}5EC$ (15% Trehelose)).

The second prototype series was two sets of formulation comprising either 5% or 15% trehalase, instead of sucrose, in a TRIS buffered system. Since the pH drifted in the prototype 1 formulations, the molarity of the TRIS buffer was increased from 10 mM to 80 mM. Also, an antioxidant, L-glutathione, was added to the composition, as well as EDTA. The exact compositions are presented in Table 19 and illustrated in FIG. 3. FIGS. 31 and 32 show the pH over time of rPA aqueous formulations and rPA+nanoemulsion formulations with either 5% or 15% trehelose.

The rPA+20% $W_{80}5EC$ formulations in both the low and high dose of rPA achieved stability at 5° C. for 12 months with either 5% or 15% trehaolse. The main advantage of having 15% trehalose verse 5% can be seen in the results. Table 33 shows the overall summary of Prototype 2: TRIS system+5% trehelose, and Table 34 shows the overall summary of Prototype 2: TRIS system+15% trehelose. Moreover, at 6 months at 25° C., the rPA+20% $W_{80}$5EC containing 15% trehalose retained approximately intact 20% rPA, while the 5% systems contained less than 5%. This is an important point, as at higher storage temperatures over a longer period of time, a higher concentration of trehalose can help stabilize rPA in its native form than a lower concentration of trehalose. The pH is stabilized with the 15% trehalose as shown in FIG. 32.

TABLE 33

Overall Summary of Prototype 2: TRIS System + 5% Trehaolse

| | | Low Dose rPA | | High Dose rPA | | |
|---|---|---|---|---|---|---|
| Month | Temp | Solution (X-1624) | 100 μg/mL + 20% $W_{80}5EC$ (X-1625) | Solution (X-1626) | 500 μg/mL + 20% $W_{80}5EC$ (X-1627) | $W_{80}5EC$ + Buffer 20% $W_{80}5EC$ (X-1628) |
| 1 | −20 | Pass | Pass | Pass | Pass | Pass |
| | 5 | Pass | Pass | Pass | Pass | Pass |
| | 25 | Pass | Fail | Pass | Fail | Pass |
| | 40 | Fail | Fail | Fail | Fail | Pass |
| 3 | −20 | Pass | Pass | Pass | Pass | Pass |
| | 5 | Pass | Pass | Pass | Pass | Pass |
| | 25 | Fail | Fail | Fail | Fail | Pass |
| | 40 | Fail | Fail | Fail | Fail | Fail |
| 6 | −20 | Pass | Pass | Pass | Pass | Pass |
| | 5 | Pass | Pass/Fail | Pass | Pass | Pass |
| | 25 | Fail | Fail | Fail | Fail | Pass |
| | 40 | Fail | Fail | Fail | Fail | Fail |
| 9 | −20 | Fail | Pass | Pass | Pass | Pass |
| | 5 | Fail | Pass | Pass | Pass | Pass |
| | 25 | X | X | X | X | Fail |

TABLE 34

Overall Summary of Prototype 2: TRIS System + 15% Trehalose

| | | Low Dose rPA | | High Dose rPA | | |
|---|---|---|---|---|---|---|
| Month | Temp | Solution (X-1629) | 100 μg/mL + 20% $W_{80}5EC$ (X-1630) | Solution (X-1631) | 500 μg/mL + 20% $W_{80}5EC$ (X-1632) | $W_{80}5EC$ + Buffer 20% $W_{80}5E$ C(X-1633) |
| 1 | −20 | Pass | Pass | Pass | Pass | Pass |
| | 5 | Pass | Pass | Pass | Pass | Pass |
| | 25 | Pass | Fail | Pass | Pass | Pass |
| | 40 | Fail | Fail | Fail | Fail | Pass |
| 3 | −20 | Pass | Pass | Pass | Pass | Pass |
| | 5 | Pass | Pass | Pass | Pass | Pass |
| | 25 | Fail | Fail | Pass | Fail | Pass |
| | 40 | Fail | Fail | Fail | Fail | Pass |
| 6 | −20 | Pass | Pass | Pass | Pass | Pass |
| | 5 | Pass | Pass/Fail | Pass | Pass | Pass |
| | 25 | Fail | Fail | Fail | Fail | Pass |
| | 40 | Fail | Fail | Fail | Fail | Fail |
| 9 | −20 | Pass | Pass | Pass | Fail | Pass |
| | 5 | Pass | Pass | Pass | Pass | Pass |
| | 25 | X | X | X | X | Fail |

Example 26—Prototype 3: TRIS Buffered System: Effect of Glutathione

The third prototype series was investigating L-Glutathione in a TRIS buffered system. The exact compositions of the formulations are presented in Table 20 and illustrated in FIG. 4. The purpose of this example was to understand the contribution of glutathione and histidine when incorporated in a TRIS buffered system. The histidine was increased from 20 mM to 60 mM in this study.

Figure 33:
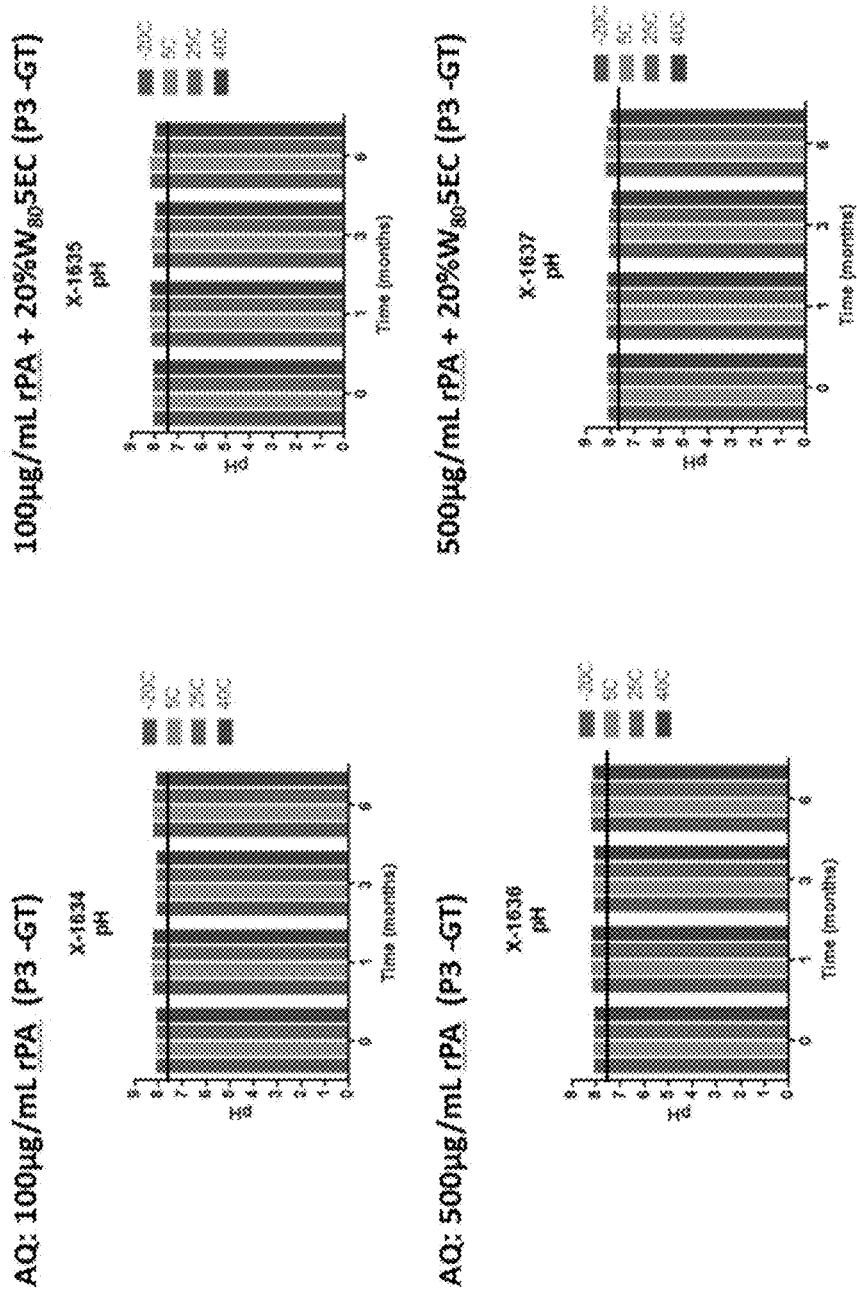
FIG. 33 shows the pH over time at different temperatures of different prototype protein formulations: aqueous rPA, rPA+nanoemulsion (20% $W_{80}5EC$ (TRIS with no glutathione)).
Figure 34:
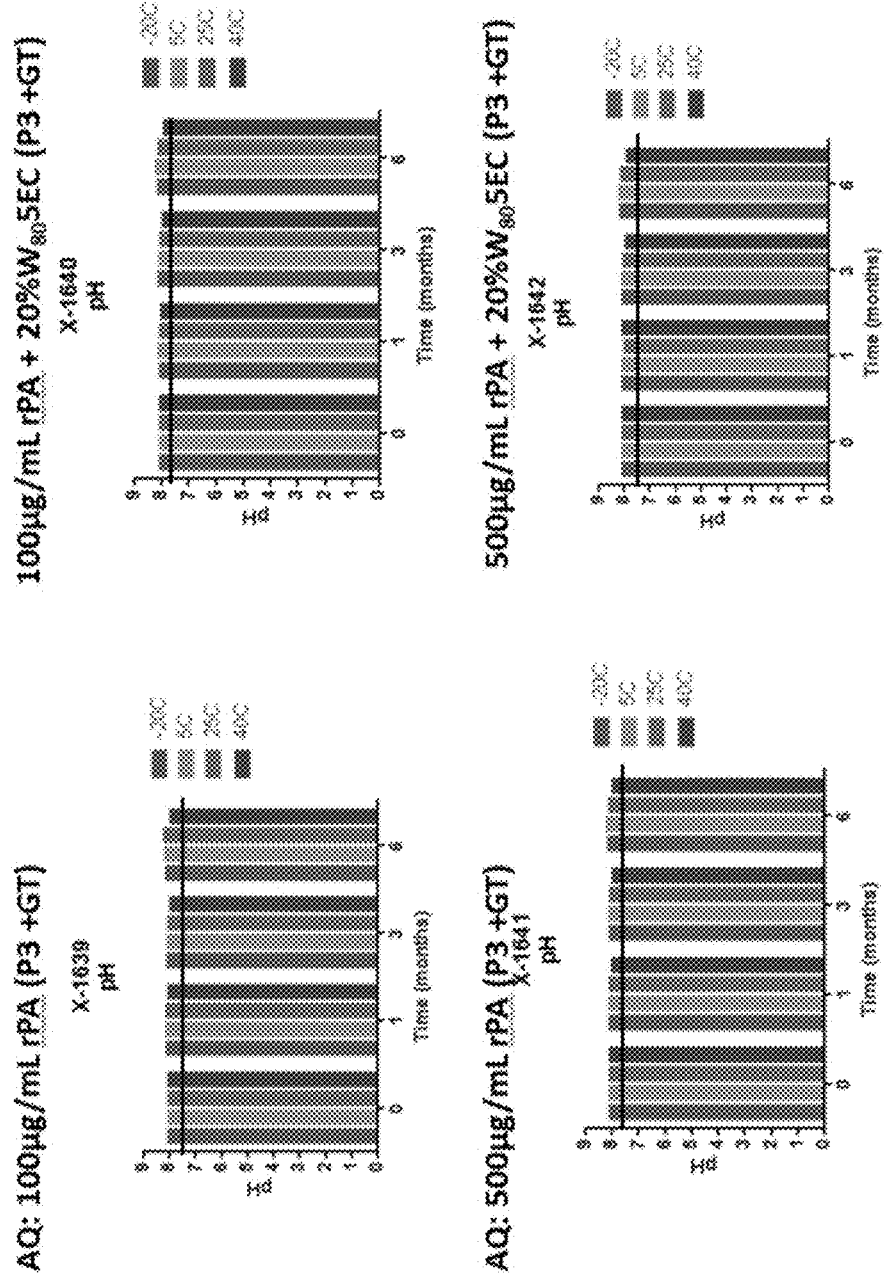
FIG. 34 shows the pH over time at different temperatures of different prototype protein formulations: aqueous rPA, rPA+nanoemulsion (20% $W_{80}5EC$ (TRIS+glutathione)).
Figure 35:
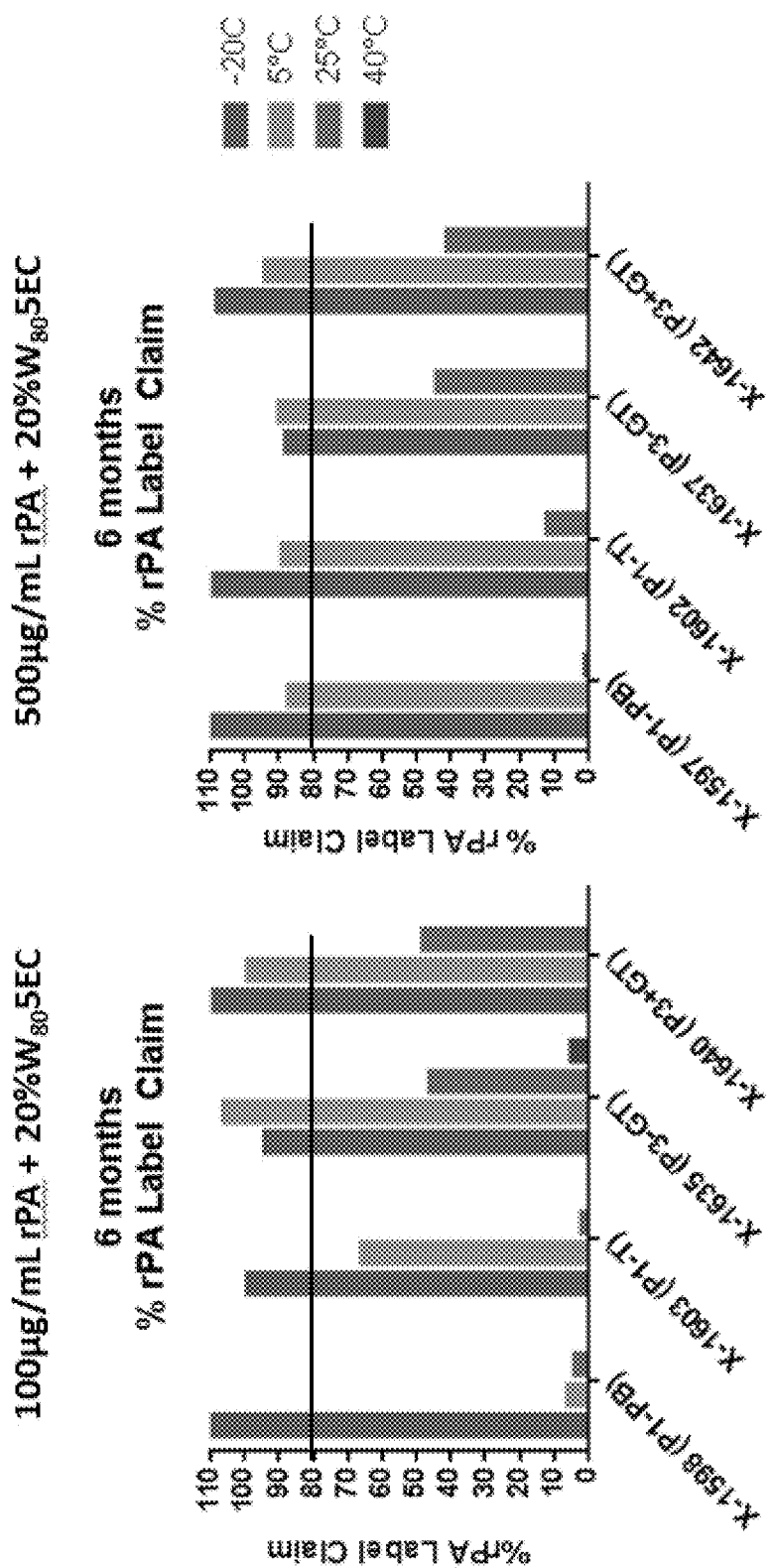
FIG. 35 shows a comparison of rPA+20% $W_{80}5EC$: Prototypes 1 vs. 3 at 6 months.
Figure 36:
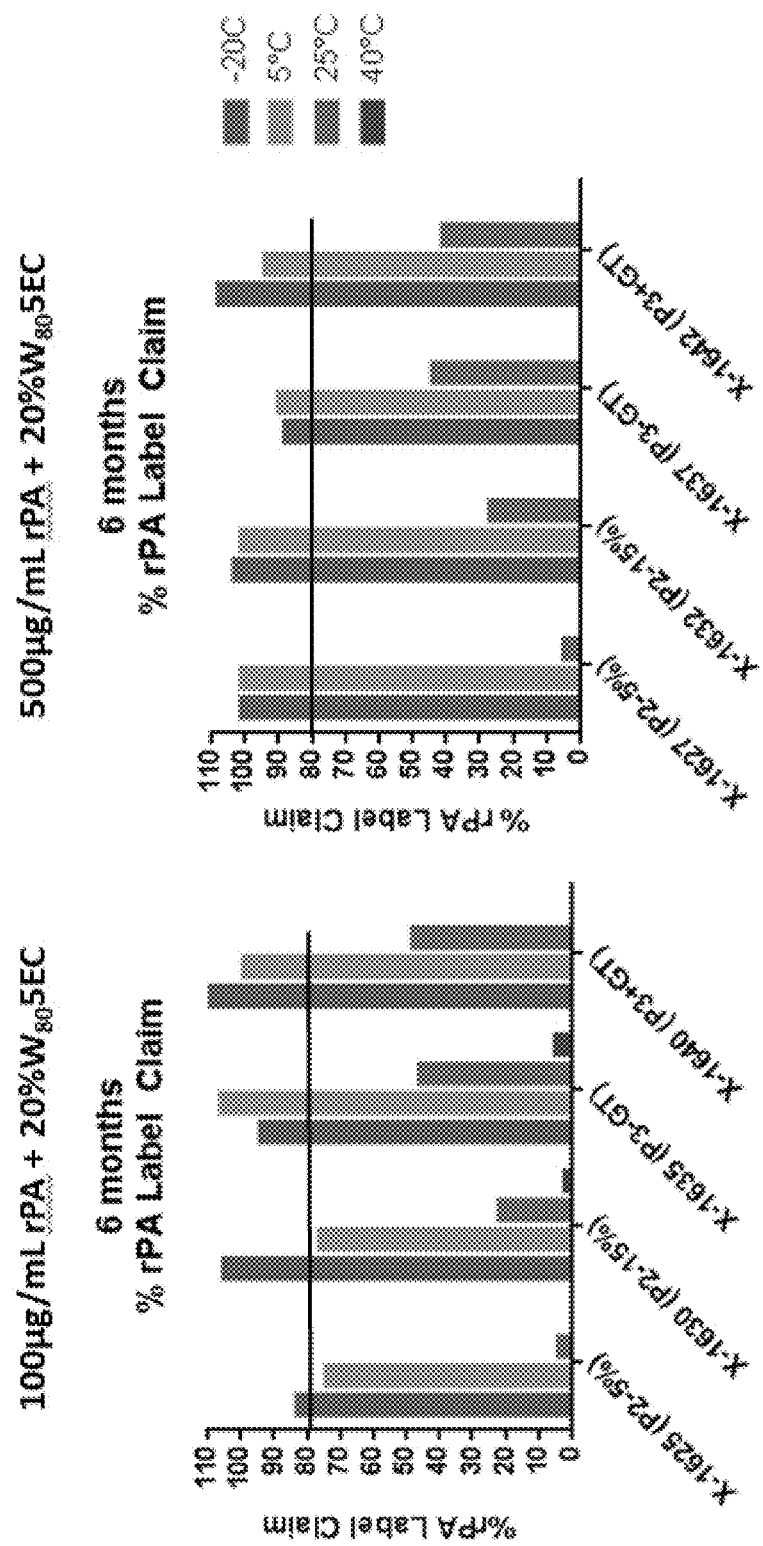
FIG. 36 shows a comparison of rPA+20% $W_{80}5EC$: Prototypes 2 vs. 3 (6 months).
Figure 37:
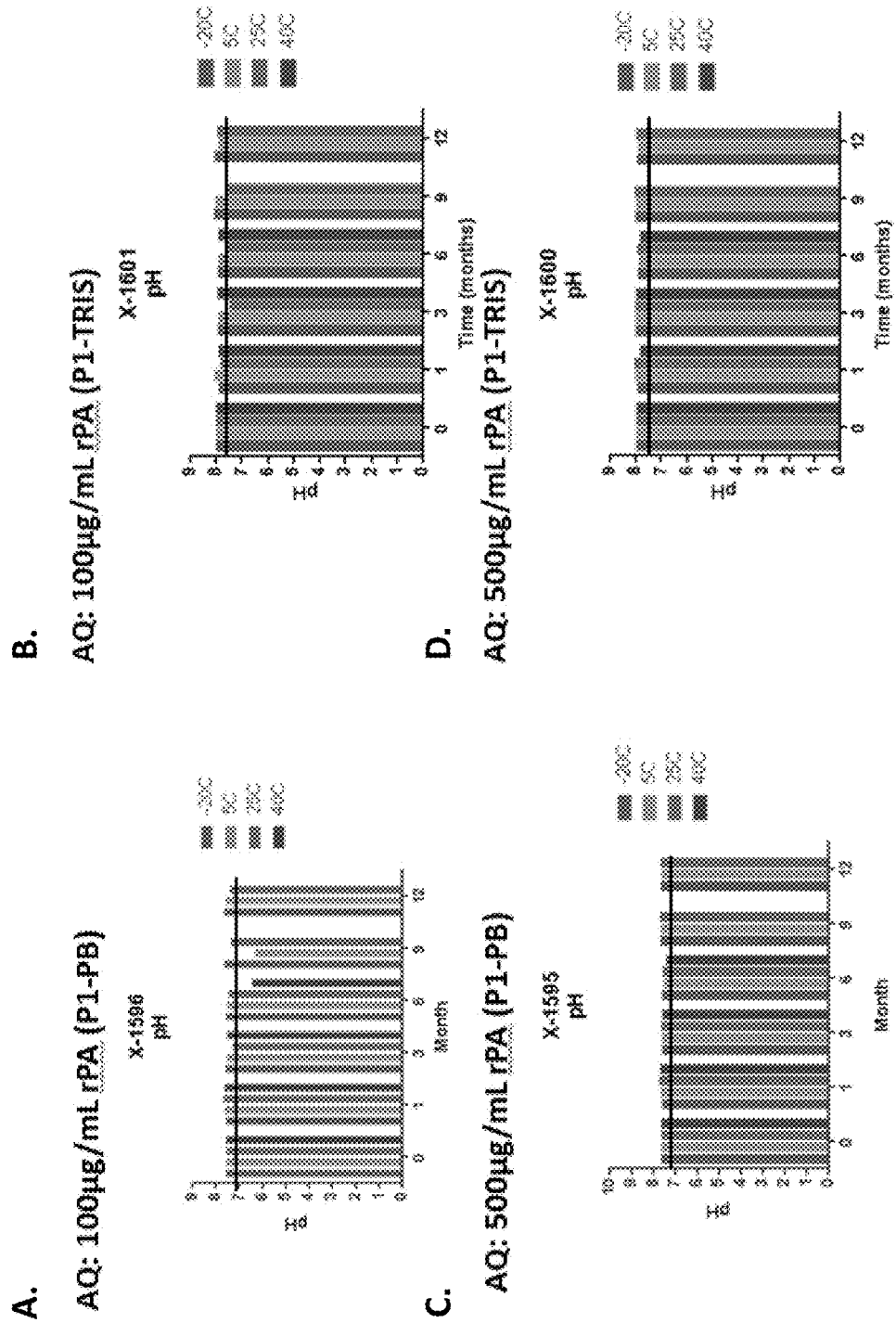
FIG. 37 shows pH assessment of Prototype 1 rPA formulations over time. (A) and (B) show formulations with 100 μg of rPA and panels (C) and (D) show formulations with 500 μg of rPA.
Figure 38:
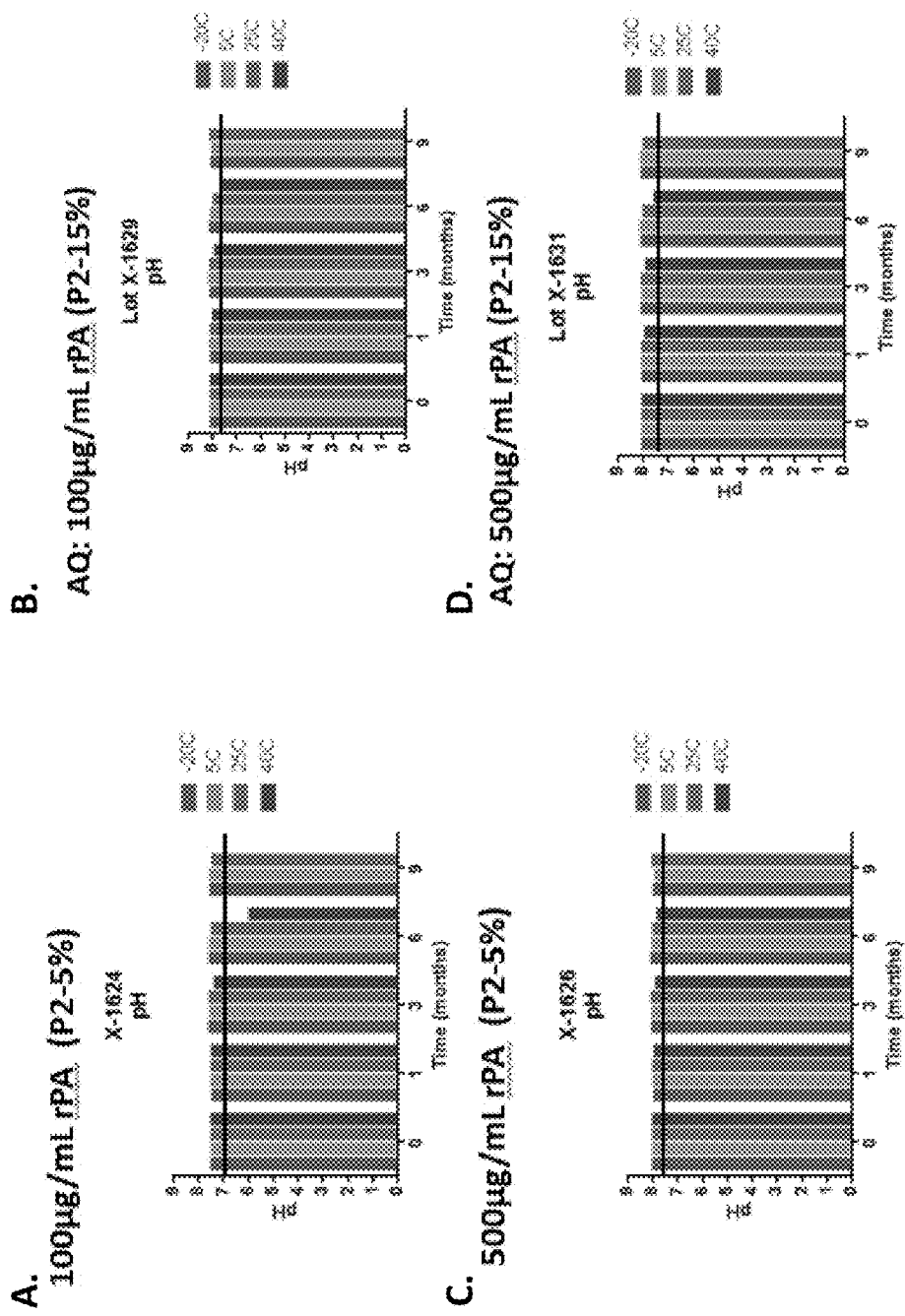
FIG. 38 shows pH assessment of Prototype 2 rPA formulations over time. (A) and (B) show formulations with 100 μg of rPA and panels (C) and (D) show formulations with 500 μg of rPA.
Figure 39:
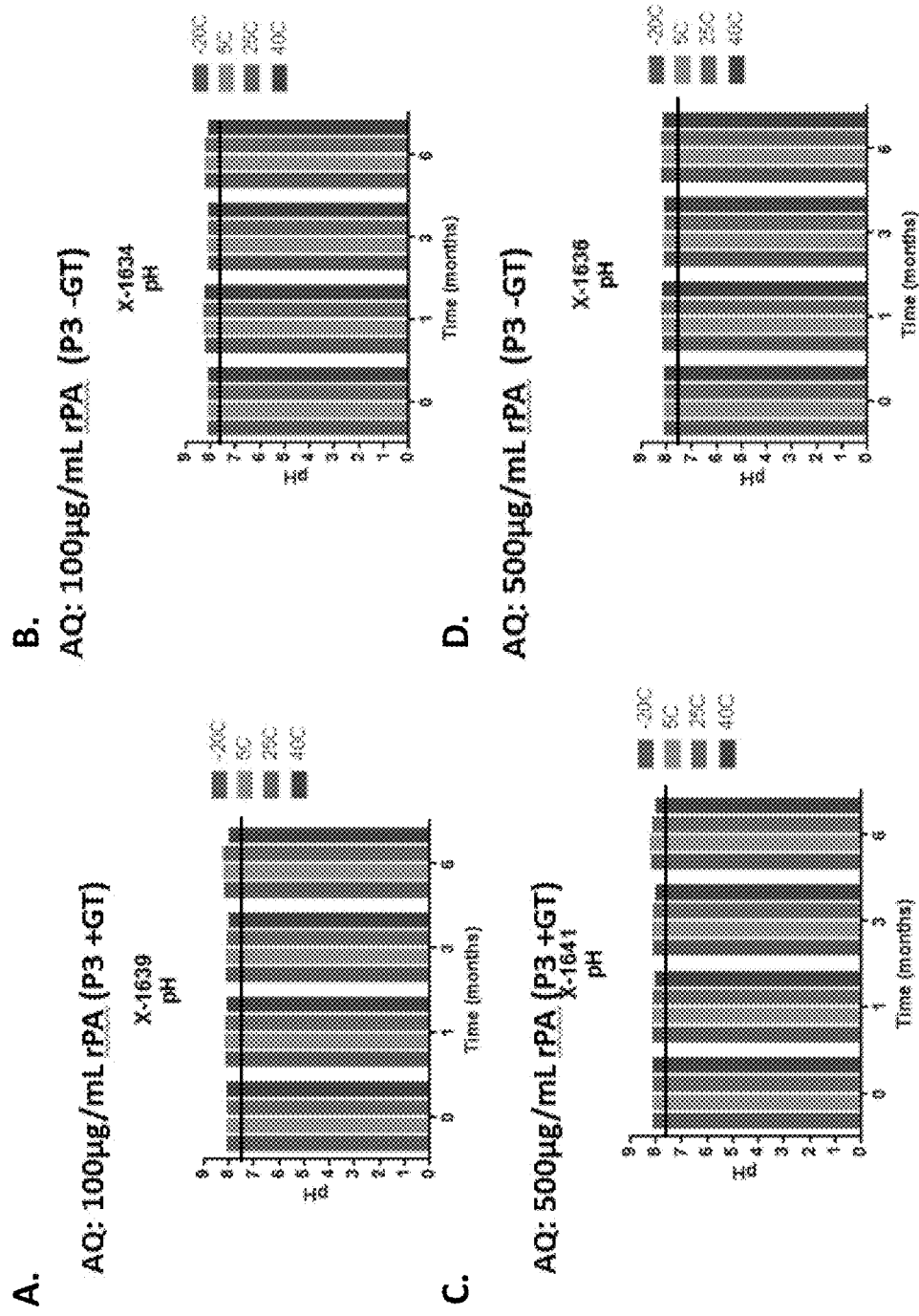
FIG. 39 shows pH assessment of Prototype 3 rPA formulations over time. (A) and (B) show formulations with 100 μg of rPA and panels (C) and (D) show formulations with 500 μg of rPA.
Figure 40:
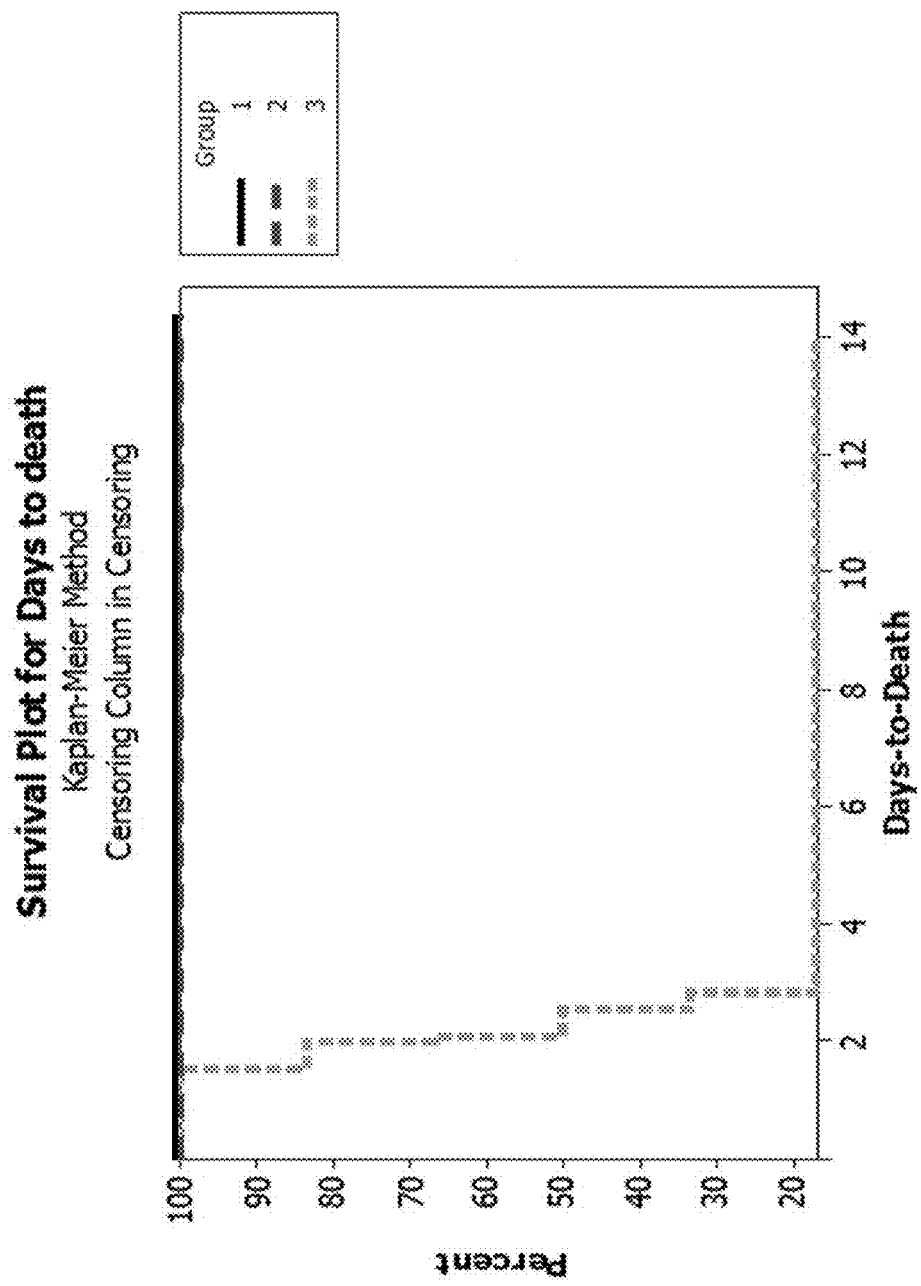
FIG. 40 shows a survival plot of rabbits challenged with anthrax following immunization with nanoemulsion vaccinations of the disclosure. Group 1 received a vaccine comprising NE+100 μg rPA, Group 1 received a vaccine comprising NE+20 μg rPA, and Group 3 received saline.

The pH of the rPA aqueous systems was very stable over time at the low and high dose of rPA (FIGS. 33 and 34). This was also apparent in the rPA+20% $W_{80}5EC$ system. Table 35 shows the overall summary of Prototype 3: TRIS system with Glutathione, and Table 36 shows the overall summary of Prototype 3: TRIS system in the absence of Glutathione.

The results show that there was no a great effect with the addition of glutathione. The effect seems to be attributed to increasing the histidine from 20 mM to 60 mM when comparing prototypes 2 that has 20 mM histidine with 15% trehaolse, and glutathione to the Prototype 3 formulation.

TABLE 35

Overall Summary of Prototype 3: TRIS System with Glutathione

| | | Low Dose rPA | | High Dose rPA | | |
|---|---|---|---|---|---|---|
| Month | Temp | Solution (X-1634) | 100 µg/mL + 20% W$_{80}$5EC (X-1635) | Solution (X-1636) | 500 µg/mL + 20% W$_{80}$5EC (X-1637) | W$_{80}$5EC + Buffer 20% W$_{80}$5EC (X-1638) |
| 1 | −20 | Pass | Pass | Pass | Pass | Pass |
|   | 5   | Pass | Pass | Pass | Pass | Pass |
|   | 25  | Pass | Pass | Pass | Pass | Pass |
|   | 40  | Fail | Fail | Fail | Fail | Pass |
| 3 | −20 | Pass | Pass | Pass | Pass | Pass |
|   | 5   | Pass | Pass | Pass | Pass | Pass |
|   | 25  | Pass | Fail | Pass | Fail | Pass |
|   | 40  | Fail | Fail | Fail | Fail | Fail (% CPC) |
| 6 | −20 | Pass | Pass | Pass | Pass | Pass |
|   | 5   | Pass | Pass | Pass | Pass | Pass |
|   | 25  | Pass | Fail | Pass | Fail | Pass |
|   | 40  | Fail | Fail | Fail | Fail | Fail (% CPC) |

TABLE 36

Overall Summary of Prototype 3: TRIS System without Glutathione

| | | Low Dose rPA | | High Dose rPA | | |
|---|---|---|---|---|---|---|
| Month | Temp | Solution (X-1639) | 100 µg/mL + 20% W$_{80}$5EC (X-1640) | Solution (X-1641) | 500 µg/mL + 20% W$_{80}$5EC (X-1642) | W$_{80}$5EC + Buffer 20% W$_{80}$5EC (X-1643) |
| 1 | −20 | Pass | Pass | Pass | Pass | Pass |
|   | 5   | Pass | Pass | Pass | Pass | Pass |
|   | 25  | Pass | Pass | Pass | Pass | Pass |
|   | 40  | Fail | Fail | Fail | Fail | Pass |
| 3 | −20 | Pass | Pass | Pass | Pass | Pass |
|   | 5   | Pass | Pass | Pass | Pass | Pass |
|   | 25  | Pass | Fail | Pass | Fail | Pass |
|   | 40  | Fail | Fail | Fail | Fail | Pass |
| 6 | −20 | Pass | Pass | Pass | Pass | Pass |
|   | 5   | Pass | Pass | Pass | Pass | Pass |
|   | 25  | Pass | Fail | Pass | Fail | Pass |
|   | 40  | Fail | Fail | Fail | Fail | Pass |

Example 27—Comparision of Prototypes Summary

FIG. 35 shows a comparison of Prototype 1 and 3. It is apparent that Prototype 3 formulations that contain rPA+ 20% $W_{80}$5EC were more stable at higher temperature than Prototype 1 at the same stability timepoint of 6 months. The rPA label claim of X-1635, X-1640, X1637 and X-1642 at 25° C. was about 40%. The prototype 1 formulations was between 2-10% stable rPA recovered by RP-HPLC or SEC-HPLC. This indicates longer stability at higher temperatures.

FIG. 36 shows a comparison of Prototype 2 and 3 stability of rPA at the same stability time point of 6 months. It is apparent that Prototype 3 formulations that contain rPA+ 20% $W_{80}$5EC were more stable at higher temperatures than Prototype 2. The rPA label claim of X-1625, X-1630, X-1627, and X-1632 were between roughly 5-20%. Prototype 3 formulations retained 40% or more rPA in formulations of X-1635, X-1640, X-1637, and X-1642. This indicates longer stability at higher temperature for this prototype series.

Example 28—Intranasal Administration of Vaccine in an Animal Model

An intranasal rabbit immunogenicity study was completed using a prototype rPA vaccine formulation. The primary aim was to show that immunization with the vaccine would result in the generation of toxin neutralizing antibodies. There were 6 rabbits in each treatment group (Group 1. NE+rPA 100 μg; Group 2. NE+rPA 20 μg; and Group 3. Saline). Rabbits were vaccinated on Day 0, 28, and 56. Rabbits were challenged after 12 weeks with 100±75 $LD_{50}$ of anthrax, and follow up, including survival studies and measuring of antibodies was performed for two weeks thereafter. Samples were taken prior to administration of each vaccine dose and two weeks after the fourth dose. There were no adverse incidents reported in all vaccinated rabbits. Tables 37 and 38 below show the survival data, which is also depicted in a Kaplan-Meier plot in FIG. 40.

TABLE 37

| Percent Survival | | | | |
|---|---|---|---|---|
| Group | Item | # Exposed | # Lived | % Survival |
| 1 | IN NE-rPA; (100 μg) | 6 | 6 | 100% |
| 2 | IN NE-rPA; (20 μg) | 6 | 6 | 100% |
| 3 | Saline | 6 | 1 | 17% |

TABLE 38

| | | Days Until Death | | |
|---|---|---|---|---|
| Group | Item | d2 | d3 | d4 |
| 1 | IN NE-rPA (100 µg) | — | — | — |
| 2 | IN NE-rPA (20 µg) | — | — | — |
| 3 | Saline | — | 3 | 2 |

Additional, total bacterium counts (CFU/ml blood) were determined for the challenged animals in the study. Table 39 shows that there were no detectable bacterium in the blood of the rabbits in Groups 1 or 2 (those that were immunized), while there were detectable levels in the majority of the animals tested in the control group (Group 3).

TABLE 39

| | | Total Bacterium Count (CFU/ml Blood) | | | | | |
|---|---|---|---|---|---|---|---|
| Group | Item | Rabbit #1 | Rabbit #2 | Rabbit #3 | Rabbit #4 | Rabbit #5 | Rabbit #6 |
| 1 | IN NE-rPA (100 µg) | 0 | 0 | 0 | 0 | 0 | 0 |
| 2 | IN NE-rPA (20 µg) | 0 | 0 | 0 | 0 | 0 | 0 |
| 3 | Saline | N/A* | 3.0E+01 | 1.91E+07 | 0** | 7.30E+02 | N/A* |

Figure 41:
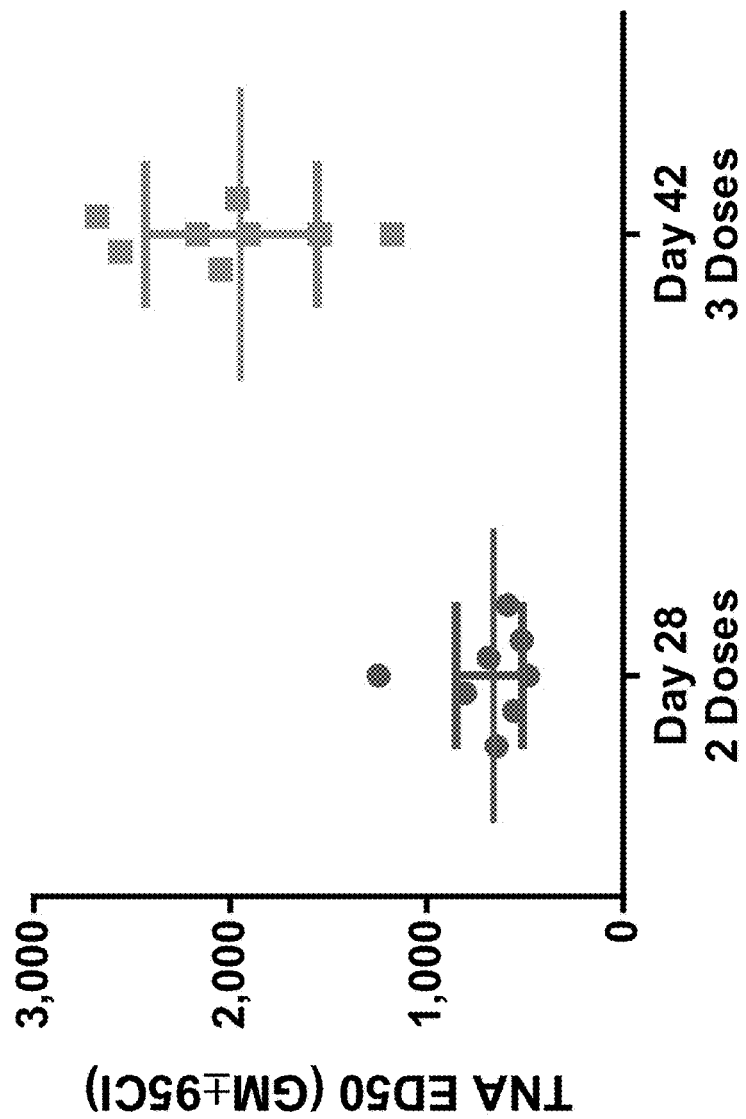
FIG. 41 shows toxin neutralizing antibody (TNA) responses following intranasal administration of a nanoemulsion vaccine.

Results indicated that functional immune response was detected in rabbit sera using a toxin neutralizing assay (TNA) and an anti-rPA IgG ELISA. Lethal Toxin neutralizing ability in the TNA was detected at Day 28 (after 2 doses) in all of the rabbits. This neutralisation response peaked at Day 42, two weeks after the 3rd vaccination and declined two weeks after the final vaccination (4th) at Day 56. These results are shown in FIG. 41. There was also good serum anti-rPA IgG response observed. The response was generally very consistent for all of the rabbits. This response mirrored the observed trend for the rabbit TNA. A positive correlation was observed between rTNA and rabbit anti-rPA IgG ELISA response. The successful detection of antibodies to rPA suggests that the developed rPA Nanoemulsion vaccine will be able to elicit a protective effect against *B. anthracis* in humans.

These results indicate that the disclosed vaccines offer improved protection by eliciting both systemic and mucosal immunity, improved safety through intranasal administration and incorporation of rPA, and improved stability via separate storage capabilities of the NE and the antigen (rPA can be stored in a stabilizing buffer at 5-25° C. for up to 12 months, while the NE is stable at 25° C. for up to 3 years). Finally, the stability, safety, and easy administration of the disclosed vaccines will enable self-administration in the event of an emergency.

Example 29—Intramuscular Administration of Vaccine in an Animal Model

In the current literature, it is accepted that protein aggregation is the most important parameter to increase the immune response in protein products (Hermeling et al., 2004). The current theory is that the reduction of protein aggregation has been linked to reduced immunogenicity (Sauerborn et al., 2010) and that protein aggregation (soluble or insoluble) leads to a more immunogenic response than monomeric proteins.

The data herein shows the opposite trend. The formulations that contained 100, 120 or 220 kDa aggregates were not as immunogenic as those that contained less aggregates (only 100 kDA) or no aggregates at all. This is a novel finding, since the current literature suggests that the monomeric proteins are less immunogenic that aggregates or those proteins.

Figure 47:
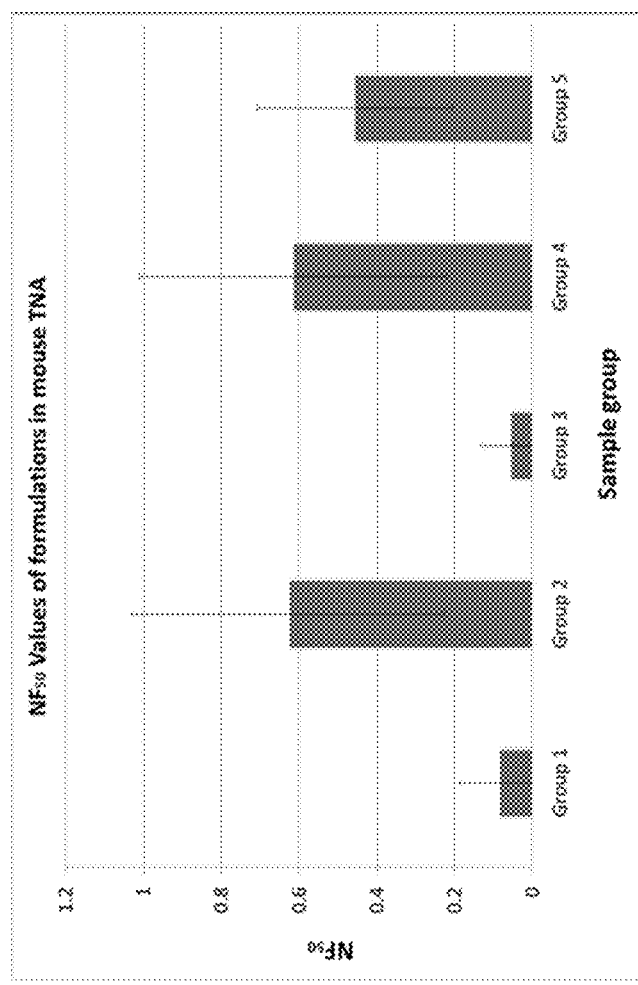
FIG. 47 shows NF50 Values Day 28 Terminal Bleed (Averages) for mice receiving IM injections of NE formulation vaccines.
Figure 48:
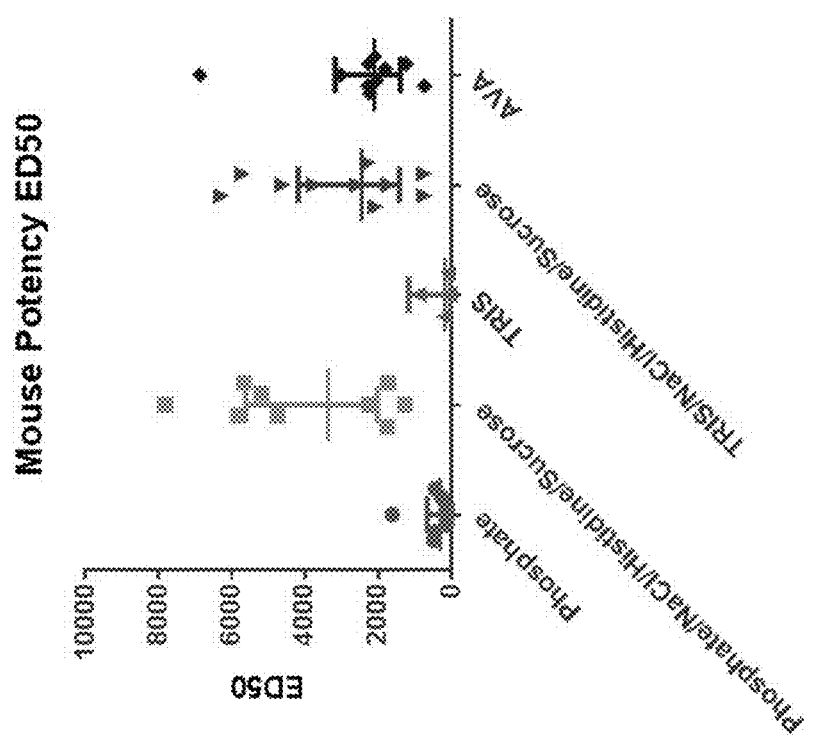
FIG. 48 shows Mouse Potency Assay ED50 (All data points, plus geomean).
Figure 49:
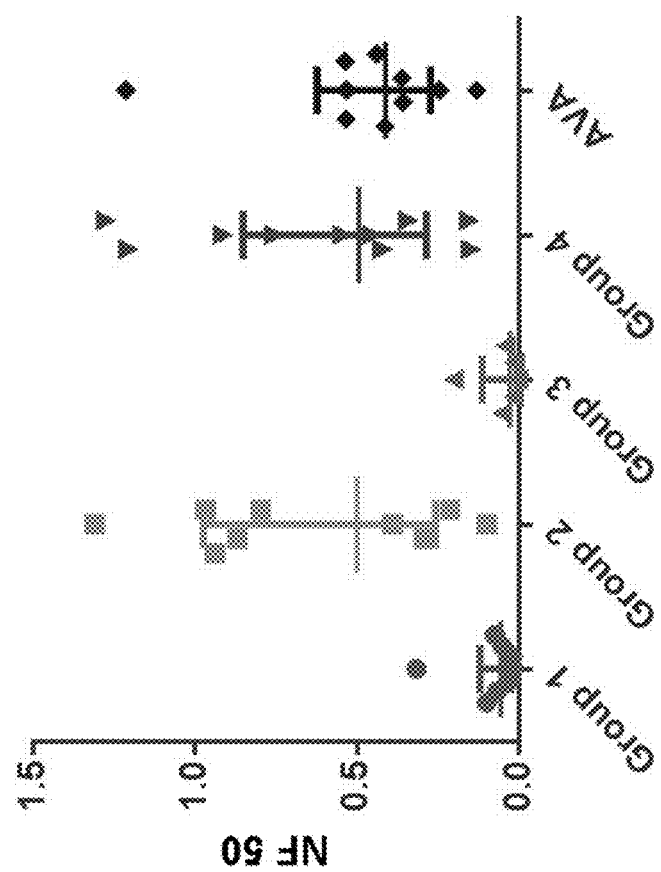
FIG. 49 shows Mouse Potency Assay NF50 (All data points, plus geomean).

Thus, a key issue for the vaccine formulation is choice of the buffer system. It was necessary to determine if the buffer has any impact on immunogenicity. From a physical stability perspective, the TRIS buffer is more favorable. A mouse potency/immunogenicity study was initiated to compare immunogenicity of vaccine formulation containing either phosphate buffer or TRIS (Table 40). Both the phosphate buffer and TRIS without additional excipients did not elicit immune responses while both the phosphate and the TRIS with additional excipients elicited immune responses comparable to the AVA positive control (FIG. 47-49 and Table 43).

TABLE 40

| | IM Mouse Potency Comparing Immunogenicity of Prototype FVFs containing either Phosphate Buffer or TRIS | | | |
|---|---|---|---|---|
| | Group | | | |
| Formulations | #1 | #2 | #3 | #4 |
| Formulation Description | rPA + 5% $W_{80}5EC$ in 25 mM phosphate buffer | rPA + 5% $W_{80}5EC$ in 10 mM phosphate buffer with 100 mM NaCl, 5% sucrose, and 20 mM histidine | rPA + 5% $W_{80}5EC$ in 10 mm TRIS buffer | rPA + 5% $W_{80}5EC$ in 10 mm TRIS buffer with 150 mM NaCl, 5% sucrose, and 20 mM histidine |
| | Composition: Components and Volume of Formulations | | | |
| 1) Volume (µL) of Stock rPA (5 mg/mL) | 12 | 12 | 12 | 12 |

TABLE 40-continued

IM Mouse Potency Comparing Immunogenicity of Prototype
FVFs containing either Phosphate Buffer or TRIS

| Formulations | Group #1 | #2 | #3 | #4 |
|---|---|---|---|---|
| 2) Volume (μL) of 60% $W_{80}5EC$ | 125 | 125 | 125 | 125 |
| 3) Volume (μL) of Buffer | 1363 | 1363 | 1363 | 1363 |
| Total Volume Prepared (1 + 2 + 3, μL) | 1500 | 1500 | 1500 | 1500 |
| Final rPA Concentration, Dosing and Schedule | | | | |
| Final rPA Antigen Concentration (w/v; μL/mL) | 40 μg/mL | 40 μg/mL | 40 μg/mL | 40 μg/mL |
| rPA Dose Amount per dose volume # of Doses/Day | 2 μg in 50 μL Two IM doses: Day 0 and 14; Sacrifice Day 28 | 2 μg in 50 μL Two IM doses: Day 0 and 14; Sacrifice Day 28 | 2 μg in 50 μL Two IM doses: Day 0 and 14; Sacrifice Day 28 | 2 μg in 50 μL Two IM doses: Day 0 and 14; Sacrifice Day 28 |

*AVA was used as the positive control in this study as Group #5. (FIG. 47)

TABLE 41

Summary of Formulations and Western Blots

| Formulations: 0.04 mg/mL rPA + 5% NE | rPA Band at 83 kDA | Higher weight molecular weight bands (110, 120, 220 kDa and above) |
|---|---|---|
| NE-rPA in 25 mM Phosphate Buffer, pH 8 | Yes | Yes (100, 120, 220 kDa) |
| NE-rPA in 10 mM Phosphate Buffer, 100 mM NaCl, 20 mM Histidine, 5% Sucrose, pH 8 | Yes | Yes (100 kDa) |
| NE-rPA in 10 mM TRIS, pH 8 | Yes | Yes (In Stock, 100 120, 220 kDa) |
| NE-rPA in 10 mM TRIS, 150 mM NaCl, 20 mM Histidine, 5% Sucrose, pH 8 | Yes | No |

The rPA+NE formulations were prepared by the following steps and were injected into mice via the intramuscular route of administration: (1) "Stock" formulation of 0.16 mg/mL rPA+20% NE was prepared; and (2) The "Stock" formulation was diluted with the desired buffer system to yield a 0.04 mg/ml rPA+5% NE formulation for IM injection.

The "Stock" Formulations (0.16 mg/mL+20% NE) and the diluted formulations (0.04 mg/mL+5% NE) used in the IM mouse potency study were tested for aggregates by Western Blot, as noted in Table 41.

A formulation containing 0.5 mg/mL rPA+20% NE was also run on the Western Blot as the comparitor as this preparation will be the high dose intranasal formulation in future human clinical studies. The results of testing various formulations are shown in FIGS. 43-46.

Mouse Immunogenicity Study Design and Results:

The design of the completed mouse potency study is presented in Table 42 and the results in FIG. 47-49 and Table 42. In this study, changes in excipients had highly significant effects upon immune responses in mice.

Groups 1 and 3, rPA (2 μg)+5% $W_{80}5EC$ in 25 mM phosphate buffer (PB) and rPA (2 μg)+5% $W_{80}5EC$ in 10 mM Tris showed only minimal responses in the toxin neutralization assay.

Groups 2 and 4, rPA (2 μg)+5% $W_{80}5EC$ in 10 mM phosphate buffer, 100 mM NaCl, 20 mM Histidine, 5% Sucrose and rPA (2 μg) rPA+5% $W_{80}5EC$ in 10 mm TRIS, 150 mM NaCl 20 mM Histidine, 5% Sucrose showed robust responses comparable in magnitude to those seen with the positive control, AVA.

Excipients, therefore, can have a major influence on immune response in this assay and although stability is an important factor in formulation selection, the epitopes responsible for immunogenicity have to be preserved and not interfered with by the addition of excipients. It is immunogenicity that will ultimately determine success of the vaccine.

From the Western Blot data, aggregates were present in the formulations showing only minimal responses in the toxin neutralization assay. While formulations without large aggregates (over 120 kDA) or no aggregates at all showed robust responses comparable in magnitude to those seen with the positive control, AVA. The formulations that had little of the large aggregates or aggregates had excipients to provide structural stability to the monomeric protein rPA.

TABLE 42

Mouse Study Design

| Group | Vaccine | Route | rPA (μg/dose)[1,2] | Volume (μl) | N |
|---|---|---|---|---|---|
| 1 | rPA + 5% $W_{80}5EC$ in phosphate buffer | IM | 2 | 50 | 10 |
| 2 | rPA + 5% $W_{80}5EC$ in phosphate buffer, NaCl, Histidine, Sucrose | IM | 2 | 50 | 10 |
| 4 | rPA + 5% $W_{80}5EC$ in TRIS | IM | 2 | 50 | 10 |
| 5 | rPA + 5% $W_{80}5EC$ in TRIS, NaCl Histidine, Sucrose | IM | 2 | 50 | 10 |
| 5 | AVA (Positive Control) | IM | — | 50 | 10 |

[1] Mice will be vaccinated at Week 0 and Week 2 (Day 14)
[2] rPA concentration: 0.04 mg/ml

TABLE 43

| Group Means Day 28 Terminal Bleed | | | |
|---|---|---|---|
| Group | Vaccine | Mean ± SD | Aggregate Bands (Large/Small) |
| #1 | rPA + 5% $W_{80}$5EC in 25 mM phosphate buffer | 0.09 ± 0.10 | Yes (Large) |
| #2 | rPA + 5% $W_{80}$5EC in 10 mM phosphate buffer with 100 mM NaCl, 5% sucrose, and 20 mM histidine | 0.63 ± 0.40 | Yes (Small) |
| #3 | rPA + 5% $W_{80}$5EC in 10 mm TRIS buffer | 0.06 ± 0.07 | Yes (Large) |
| #4 | rPA + 5% $W_{80}$5EC in 10 mm TRIS buffer with 150 mM NaCl, 5% sucrose, and 20 mM histidine | 0.62 ± 0.39 | No |
| #5 | AVA Positive Control | 0.46 ± 0.25 | — |

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed:

1. An aqueous composition consisting of:

(1) a recombinant protective antigen (rPA) of anthrax, wherein the rPA is present in a concentration of from about 50 μg/mL to about 750 μg/mL, (2) a nanoemulsion, and (3) a stabilizing system, wherein the stabilizing system consists of:

(a) tris(hydroxymethyl)aminomethane (TRIS) buffer;

(b) at least one salt;

(c) glycerol or at least one sugar selected from the group consisting of trehalose and sucrose;

(d) histidine; and (e) optionally, at least one antioxidant;

wherein the composition preserves the potency of the rPA antigen by protecting it from degradation over time as compared to a composition comprising rPA and a nanoemulsion but lacking the stabilizing system, and wherein the preserved potency is demonstrated by the formulation retaining at least about 80% rPA following storage at about 5° C. for at least 12 months as determined by RP-HPLC and/or SEC-HPLC.

2. The composition of claim 1, wherein the composition consists of rPA, the nanoemulsion, and the stabilizing system.

3. The composition of claim 1, wherein the rPA is in a concentration of from about 100 μg/ml to about 500 μg/ml.

4. The composition of claim 1, wherein the nanoemulsion is $W_{80}$5EC nanoemulsion adjuvant.

5. The composition of claim 4, wherein the $W_{80}$5EC nanoemulsion adjuvant is in a concentration of about 20%.

6. The composition of claim 1, wherein the TRIS buffer is in a concentration of about 5 to about 100 mM.

7. The composition of claim 6, wherein the TRIS buffer is in a concentration of about 10 mM.

8. The composition of claim 6, wherein the TRIS buffer is in a concentration of about 80 mM.

9. The composition of claim 1, wherein the salt is sodium chloride.

10. The composition of claim 9, wherein the sodium chloride is in a concentration of about 50 to about 150 mM.

11. The composition of claim 1, wherein the salt is calcium chloride.

12. The composition of claim 11, wherein the calcium chloride is in a concentration of about 50 to about 150 mM.

13. The composition of claim 1, wherein the sugar is trehalose.

14. The composition of claim 13, wherein the trehalose is in a concentration of about 5 to about 15%.

15. The composition of claim 1, wherein the histidine is in a concentration of about 20 to about 70 mM.

16. The composition of claim 15, wherein the histidine is in a concentration of about 60 mM.

17. A method of eliciting an immune response in a subject, comprising administering to a subject in need thereof an effective amount of the composition of claim 1.

18. The method of claim 17, wherein the subject is at risk of being exposed to anthrax.

19. The method of claim 17, wherein the composition is administered intranasally.

20. The composition of claim 1, wherein the sugar is sucrose.

21. The composition of claim 20, wherein the sucrose is in a concentration of about 5 to about 15%.

22. The composition of claim 1, wherein the sugar is sucrose at a concentration of about 5% to about 15%, and the amino acid is histidine at a concentration of about 20 mM to about 70 mM.

23. The composition of claim 1, wherein TRIS is at a concentration of about 10 mM, the sugar is sucrose at a concentration of about 5% to about 15%, and the amino acid is histidine at a concentration of about 20 mM to about 70 mM.

24. The composition of claim 1, wherein the rPA does not comprise a chemically modified thiol group.

25. The composition of claim 1, wherein the preserved potency is demonstrated by the formulation retaining at least about 80% rPA following storage at about 25° C. for at least 6 months as determined by RP-HPLC and/or SEC-HPLC.

26. The composition of claim 1, wherein the preserved potency is demonstrated by the formulation retaining at least about 80% rPA following storage at about −20° C. for at least 6 months as determined by RP-HPLC and/or SEC-HPLC.

27. The composition of claim 1, wherein the preserved potency is demonstrated by the formulation retaining at least about 80% rPA following storage at about −20° C. for at least 12 months as determined by RP-HPLC and/or SEC-HPLC.

* * * * *